(12) United States Patent
Kawai et al.

(10) Patent No.: US 9,321,747 B2
(45) Date of Patent: *Apr. 26, 2016

(54) ACID ADDITION SALT OF SUBSTITUTED PYRIDINE COMPOUND

(71) Applicants: DAIICHI SANKYO COMPANY, LIMITED, Tokyo (JP); UBE INDUSTRIES, LTD., Yamaguchi (JP)

(72) Inventors: Yukinori Kawai, Tokyo (JP); Noriaki Iwase, Yamaguchi (JP); Osamu Kikuchi, Yamaguchi (JP); Katsunori Takata, Yamaguchi (JP); Takahiro Motoyama, Yamaguchi (JP); Masahiko Hagihara, Yamaguchi (JP)

(73) Assignees: DAIICHI SANKYO COMPANY, LIMITED, Tokyo (JP); UBE INDUSTRIES, LTD., Yamaguchi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/370,634

(22) PCT Filed: Jan. 4, 2013

(86) PCT No.: PCT/JP2013/050005
§ 371 (c)(1),
(2) Date: Feb. 12, 2015

(87) PCT Pub. No.: WO2013/103150
PCT Pub. Date: Jul. 11, 2013

(65) Prior Publication Data
US 2015/0299169 A1    Oct. 22, 2015

(30) Foreign Application Priority Data
Jan. 6, 2012    (JP) .................. 2012-001134

(51) Int. Cl.
| | | |
|---|---|---|
| *C07D 401/14* | (2006.01) | |
| *C07C 55/24* | (2006.01) | |
| *C07C 55/08* | (2006.01) | |
| *C07C 309/04* | (2006.01) | |

(52) U.S. Cl.
CPC .............. *C07D 401/14* (2013.01); *C07C 55/08* (2013.01); *C07C 55/24* (2013.01); *C07C 309/04* (2013.01)

(58) Field of Classification Search
USPC ............................ 514/275, 569; 544/331, 298
See application file for complete search history.

(56) References Cited

U.S. PATENT DOCUMENTS

| | | | |
|---|---|---|---|
| 5,932,587 A | 8/1999 | Schmeck et al. | |
| 6,069,148 A | 5/2000 | Schmidt et al. | |
| 6,207,671 B1 | 3/2001 | Schmidt et al. | |
| 6,291,477 B1 | 9/2001 | Schmidt et al. | |
| 6,387,929 B1 | 5/2002 | Stoltefuss et al. | |
| 6,562,976 B2 | 5/2003 | Schmidt et al. | |
| 6,897,317 B2 | 5/2005 | Schmidt et al. | |
| 2005/0043341 A1 | 2/2005 | Gielen et al. | |
| 2007/0032485 A1 | 2/2007 | Kubota et al. | |
| 2008/0194609 A1 | 8/2008 | Bischoff et al. | |
| 2008/0255068 A1 | 10/2008 | Bischoff et al. | |
| 2009/0023729 A1 | 1/2009 | Nakamura et al. | |
| 2009/0264405 A1 | 10/2009 | Ali et al. | |
| 2009/0286790 A1 | 11/2009 | Imase et al. | |
| 2011/0039828 A1 | 2/2011 | Kubota et al. | |
| 2014/0213549 A9 | 7/2014 | Nakamura et al. | |

FOREIGN PATENT DOCUMENTS

| | | |
|---|---|---|
| JP | 10-067746 | 3/1998 |
| JP | 10-167967 | 6/1998 |
| JP | 2001-516757 | 10/2001 |
| JP | 2001-517655 | 10/2001 |

(Continued)

OTHER PUBLICATIONS

International Search Report, PCT Application No. PCT/JP2013/050005, issued on Jan. 29, 2013, 3 pages (English translation).

(Continued)

*Primary Examiner* — Kristin Vajda

(74) *Attorney, Agent, or Firm* — Dorsey & Whitney LLP

(57) ABSTRACT

The present invention provides a salt of a substituted pyridine compound which has excellent CETP inhibition activity and is useful as a medicament. The present invention provides a salt of a compound represented by general formula (I):

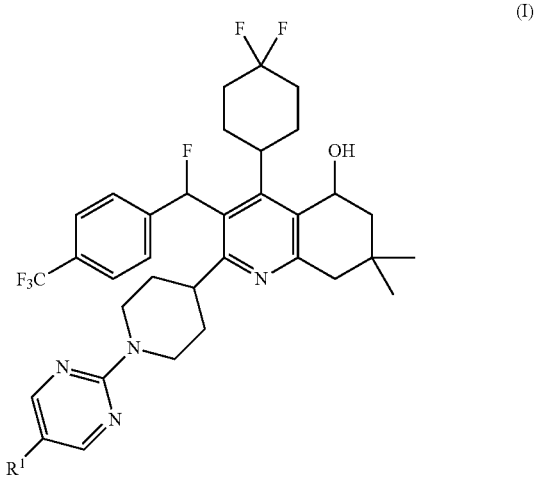

wherein $R^1$ is optionally substituted alkoxy or the like.

18 Claims, 21 Drawing Sheets

(56) References Cited

FOREIGN PATENT DOCUMENTS

| | | |
|---|---|---|
| JP | 2005-508341 | 3/2005 |
| JP | 2007-119450 A | 5/2007 |
| JP | 2007-119451 | 5/2007 |
| JP | 2007-530443 | 11/2007 |
| JP | 2007-530444 | 11/2007 |
| JP | 2008-524137 | 7/2008 |
| JP | 2008-524145 | 7/2008 |
| JP | 2009-516649 | 4/2009 |
| JP | 2009-524579 | 7/2009 |
| WO | WO 2006/072362 A1 | 7/2006 |
| WO | WO 2008/009435 A1 | 1/2008 |
| WO | WO 2008/156715 A1 | 12/2008 |
| WO | WO 2009/071509 A1 | 6/2009 |
| WO | WO 2009/109549 A1 | 9/2009 |
| WO | WO 2012/005343 A1 | 1/2012 |

OTHER PUBLICATIONS

Written Opinion of the International Searching Authority, PCT Application No. PCT/JP2013/050005, Jan. 29, 2013, 5 pages (English translation).

Supplementary European Search Report issued Mar. 17, 2015, in European Application No. EP 1 73 3708, 6 pages.

ered to as LDL) cho-
ACID ADDITION SALT OF SUBSTITUTED PYRIDINE COMPOUND

This application is a national stage application under 35 U.S.C. §371 of International Application No. PCT/JP2013/050005, filed Jan. 4, 2013, entitled "Acid Adduct Salt Of Substituted Pyridine Compound," which claims priority to Japanese Patent Application No. 2012-001134, filed Jan. 6, 2012.

TECHNICAL FIELD

The present invention relates to a novel salt of a substituted pyridine compound, which has excellent CETP inhibition activity and is useful as a medicament (particularly, a medicament for treatment or prophylaxis of dyslipidemia, low HDL cholesterolemia, arteriosclerosis or coronary heart disease).

BACKGROUND ART

It has been shown from the results of many epidemiological surveys that the concentration of serum lipoprotein is related to diseases such as dyslipidemia and arteriosclerosis (for example, Badimon, J. Clin. Invest., 1990, Vol. 85, pp. 1234-1241). Both an increase in the blood concentration of low density lipoprotein (hereinafter, referred to as LDL) cholesterol and a decrease in the blood concentration of high density lipoprotein (hereinafter, referred to as HDL) cholesterol are risk factors for coronary disease.

Cholesterol in the peripheral tissue is extracted by HDL and esterified in HDL to become cholesteryl ester (hereinafter, referred to as CE). Cholesteryl ester transfer protein (hereinafter, referred to as CETP) transfers the CE in HDL to LDL. Therefore, inhibition of CETP action increases the concentration of the CE in HDL and decreases the concentration of the CE in LDL. As described above, it is considered that a medicine which inhibits CETP activity is useful as a medicament for treatment or prophylaxis of diseases such as dyslipidemia and arteriosclerosis (for example, N. Engl. J. Med., 2004, Vol. 350, pp. 1505-1515).

Certain pyridine compounds that have CETP inhibition activity are known (for example, see Patent references 1 to 8). In addition, certain pyrimidinyl piperidine compounds that have CETP inhibition activity are known (for example, see Patent references 9 to 13).

PRIOR ART REFERENCES

Patent References

Patent reference 1: Japanese Patent Application Laid-Open (JP-A) No. Hei 10-067746 (corresponding US Patents: U.S. Pat. Nos. 6,069,148 and 6,207,671)
Patent reference 2: Japanese Patent Application National Publication No. 2001-516757 (corresponding US patent: U.S. Pat. No. 6,387,929)
Patent reference 3: Japanese Patent Application National Publication No. 2001-517655 (corresponding US patents: U.S. Pat. Nos. 6,291,477, 6,562,976 and 6,897,317)
Patent reference 4: Japanese Patent Application National Publication No. 2005-508341 (corresponding US patent application: U.S. Application Publication No. 2005/0043341)
Patent reference 5: Japanese Patent Application Laid-Open (JP-A) No. Hei 10-167967 (corresponding US patent: U.S. Pat. No. 5,932,587)
Patent reference 6: Japanese Patent Application National Publication No. 2008-524145 (corresponding US application: U.S. Application Publication No. 2008/0255068)
Patent reference 7: Japanese Patent Application National Publication No. 2008-524137 (corresponding US application: U.S. Application Publication No. 2008/0194609)
Patent reference 8: International Publication WO2009/109549
Patent reference 9: Japanese Patent Application National Publication No. 2009-516649 (corresponding US application: U.S. Application Publication No. 2009/0264405)
Patent reference 10: International Publication WO2008/156715
Patent reference 11: Japanese Patent Application National Publication No. 2009-524579 (corresponding US application: U.S. Application Publication No. 2009/0023729)
Patent reference 12: International Publication WO2008/009435 (corresponding US application: U.S. Application Publication No. 2009/0286790)
Patent reference 13: International Publication WO2009/071509

DISCLOSURE OF THE INVENTION

Object of the Invention

The inventors have researched novel salts of substituted pyridine compounds with the aim of developing an excellent CETP inhibitor and found that a salt of a substituted pyridine compound having a specific structure has excellent CETP inhibition activity and is useful as a medicament (particularly, a medicament for treatment or prophylaxis of dyslipidemia, low HDL cholesterolemia, arteriosclerosis or coronary heart disease). The invention has been accomplished on the basis of the findings described above.

Means for Achieving the Object

The present invention provides a novel salt of a substituted pyridine compound which has excellent CETP inhibition activity;

a pharmaceutical composition comprising a salt of a substituted pyridine compound as an active ingredient, and a pharmaceutical composition for treatment or prophylaxis of, preferably, dyslipidemia, hypercholesterolemia, low HDL cholesterolemia, high LDL cholesterolemia, hypertriglyceridemia, arteriosclerosis, arteriosclerotic heart disease, coronary heart disease (including heart failure, myocardial infarction, angina pectoris, cardiac ischemia, cardiovascular disorder and angioplasty-related restenosis), cerebrovascular disease (including stroke and cerebral infarction), peripheral vascular disease (including diabetic vascular complications) or obesity, more preferably dyslipidemia, low HDL cholesterolemia, high LDL cholesterolemia, arteriosclerosis, arteriosclerotic heart disease or coronary heart disease, further preferably dyslipidemia, low HDL cholesterolemia, arteriosclerosis or coronary heart disease, and even more preferably low HDL cholesterolemia or arteriosclerosis;

use of a salt of a substituted pyridine compound for preparing a pharmaceutical composition for treatment or prophylaxis (preferably treatment) of diseases (preferably the above-described diseases);

a method of treatment or prophylaxis (preferably treatment) of diseases (preferably the above-described diseases) comprising administering to a warm-blooded animal (preferably human) a pharmacologically effective amount of a salt of a substituted pyridine compound; and a method of preparing a salt of a substituted pyridine compound or an intermediate thereof.

In one aspect, the present invention provides the following.

(1) A salt formed from a compound represented by general formula (I):

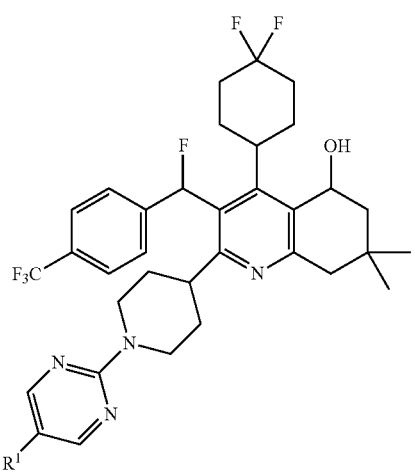

wherein R¹ represents a (2S)-2,3-dihydroxypropyloxy group, a (2R)-2,3-dihydroxypropyloxy group, a 3-hydroxy-3-methylbutoxy group, a 3-(methylsulfonyl)propoxy group, a 3-hydroxy-2-(hydroxymethyl)propoxy group, a 3-hydroxy-2-(hydroxymethyl)-2-methylpropoxy group or a 3-carboxyphenyl group, and an acid selected from the group consisting of hydrochloric acid, hydrobromic acid, methanesulfonic acid, benzenesulfonic acid, succinic acid, fumaric acid and maleic acid.

(2) The salt of the compound according to (1), which is formed from a compound represented by general formula (I-1):

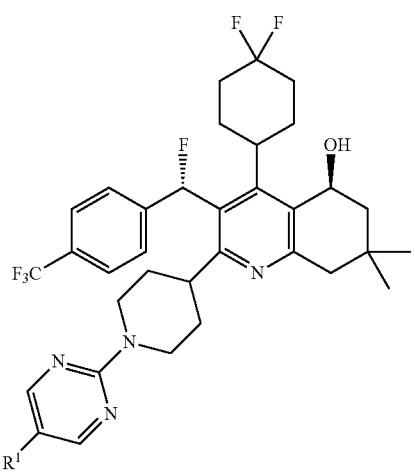

wherein R¹ represents a (2S)-2,3-dihydroxypropyloxy group, a (2R)-2,3-dihydroxypropyloxy group, a 3-hydroxy-3-methylbutoxy group, a 3-(methylsulfonyl)propoxy group, a 3-hydroxy-2-(hydroxymethyl)propoxy group, a 3-hydroxy-2-(hydroxymethyl)-2-methylpropoxy group or a 3-carboxyphenyl group, and an acid selected from the group consisting of hydrochloric acid, hydrobromic acid, methanesulfonic acid, benzenesulfonic acid, succinic acid, fumaric acid and maleic acid.

(3) The salt of the compound according to (2), wherein R¹ is a (2S)-2,3-dihydroxypropyloxy group.

(4) The salt of the compound according to (2), wherein R¹ is a (2R)-2,3-dihydroxypropyloxy group.

(5) The salt of the compound according to (2), wherein R¹ is a 3-hydroxy-3-methylbutoxy group.

(6) The salt of the compound according to (2), wherein R¹ is a 3-(methylsulfonyl)propoxy group.

(7) The salt of the compound according to (2), wherein R¹ is a 3-hydroxy-2-(hydroxymethyl)propoxy group.

(8) The salt of the compound according to (2), wherein R¹ is a 3-hydroxy-2-(hydroxymethyl)-2-methylpropoxy group.

(9) The salt of the compound according to (2), wherein R¹ is a 3-carboxyphenyl group.

(10) A pharmaceutical composition comprising the salt of the compound according to any one of (1) to (9) as an active ingredient.

(11) The pharmaceutical composition according to (10) for treatment or prophylaxis of dyslipidemia, hypercholesterolemia, low HDL cholesterolemia, high LDL cholesterolemia, hypertriglyceridemia, arteriosclerosis, arteriosclerotic heart disease, coronary heart disease, cerebrovascular disease, peripheral vascular disease or obesity.

(12) The pharmaceutical composition according to (10) for treatment or prophylaxis of dyslipidemia, low HDL cholesterolemia, arteriosclerosis or coronary heart disease.

(13) The pharmaceutical composition according to (10) for treatment or prophylaxis of low HDL cholesterolemia.

(14) The pharmaceutical composition according to (10) for treatment or prophylaxis of arteriosclerosis.

(15) The pharmaceutical composition according to (10) for treatment or prophylaxis of a disease caused by a decrease in the blood concentration of HDL cholesterol.

(16) The pharmaceutical composition according to (10) for treatment or prophylaxis of a disease caused by an increase in the blood concentration of LDL cholesterol.

(17) Use of the salt of the compound according to any one of (1) to (9) for preparing a pharmaceutical composition.

(18) The use according to (17) for preparing a pharmaceutical composition for treatment or prophylaxis of dyslipidemia, hypercholesterolemia, low HDL cholesterolemia, high LDL cholesterolemia, hypertriglyceridemia, arteriosclerosis, arteriosclerotic heart disease, coronary heart disease, cerebrovascular disease, peripheral vascular disease or obesity.

(19) The use according to (17) for preparing a pharmaceutical composition for treatment or prophylaxis of dyslipidemia, low HDL cholesterolemia, arteriosclerosis or coronary heart disease.

(20) The use according to (17) for preparing a pharmaceutical composition for treatment or prophylaxis of low HDL cholesterolemia.

(21) The use according to (17) for preparing a pharmaceutical composition for treatment or prophylaxis of arteriosclerosis.

(22) The salt of the compound according to any one of (1) to (9) for use in a method of treatment or prophylaxis of a disease.

(23) The salt of the compound according to (22), wherein the disease is dyslipidemia, hypercholesterolemia, low HDL cholesterolemia, high LDL cholesterolemia, hypertriglyceridemia, arteriosclerosis, arteriosclerotic heart disease, coronary heart disease, cerebrovascular disease, peripheral vascular disease or obesity.

(24) The salt of the compound according to (22), wherein the disease is dyslipidemia, low HDL cholesterolemia, arteriosclerosis or coronary heart disease.

(25) The salt of the compound according to (22), wherein the disease is low HDL cholesterolemia.

(26) The salt of the compound according to (22), wherein the disease is arteriosclerosis.

(27) A method of treatment or prophylaxis of a disease comprising administering to a warm-blooded animal a pharmacologically effective amount of the salt of the compound according to any one of (1) to (9).

(28) The method according to (27), wherein the disease is dyslipidemia, hypercholesterolemia, low HDL cholesterolemia, high LDL cholesterolemia, hypertriglyceridemia, arteriosclerosis, arteriosclerotic heart disease, coronary heart disease, cerebrovascular disease, peripheral vascular disease or obesity.

(29) The method according to (27), wherein the disease is dyslipidemia, low HDL cholesterolemia, arteriosclerosis or coronary heart disease.

(30) The method according to (27), wherein the disease is low HDL cholesterolemia.

(31) The method according to (27), wherein the disease is arteriosclerosis.

(32) The method according to any one of (27) to (31), wherein the warm-blooded animal is a human.

The compound represented by general formula (I) or (I-1) of the present invention encompasses compounds shown in (a-1) to (a-7) below:

(a-1) (5S)-4-(4,4-Difluorocyclohexyl)-2-[1-(5-{[(2S)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol

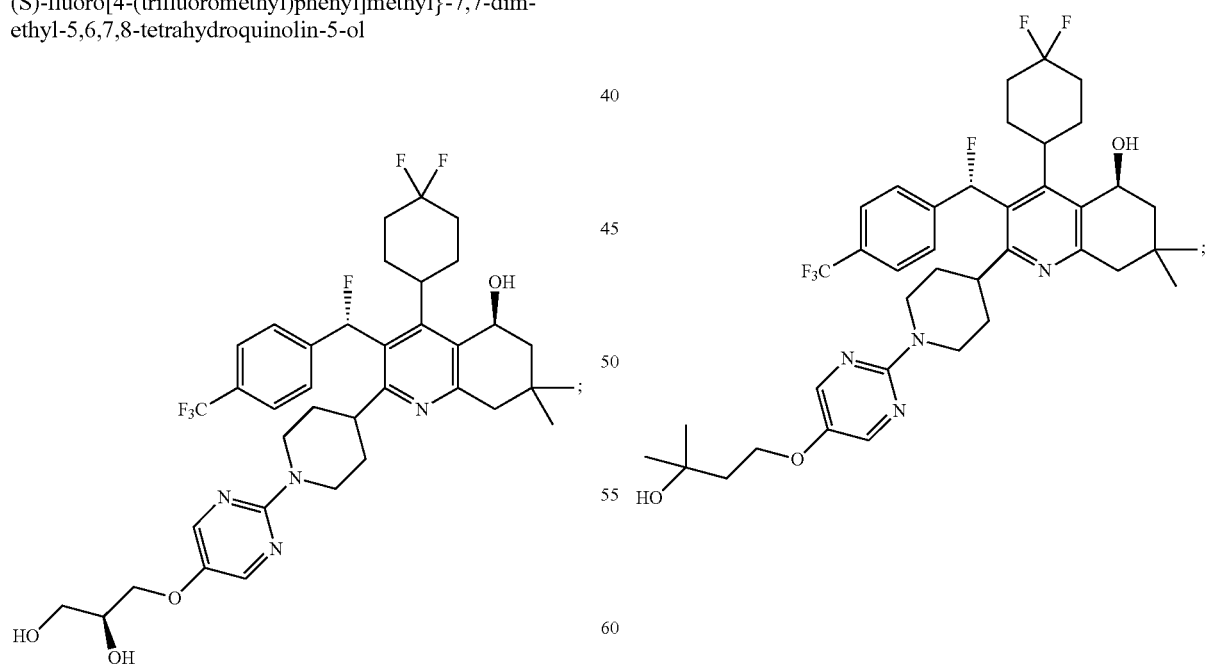

(a-2) (5S)-4-(4,4-Difluorocyclohexyl)-2-[1-(5-{[(2R)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol (a-3) (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol (a-4) (5S)-4-(4,4-Difluorocyclohexyl)-3-{(S)-fluoro[4-(trifluoromethyl)phenyl]methyl}-7,7-dimethyl-2-(1-{5-[3-(methylsulfonyl)propoxy]pyrimidin-2-yl}piperidin-4-yl)-5,6,7,8-tetrahydroquinolin-5-ol

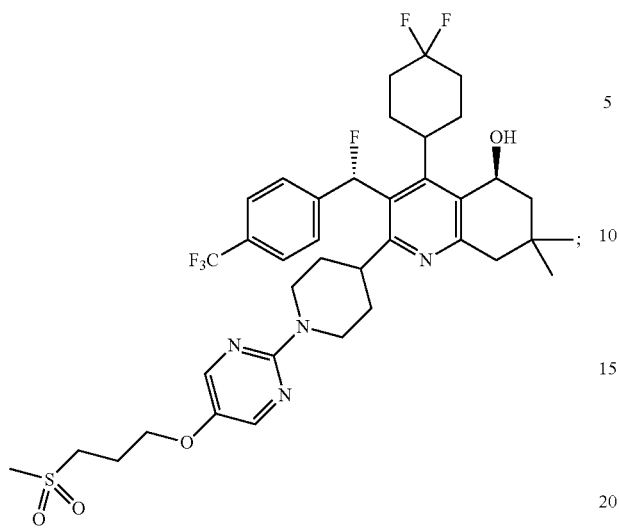

(a-5) (5S)-4-(4,4-Difluorocyclohexyl)-3-{(S)-fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol

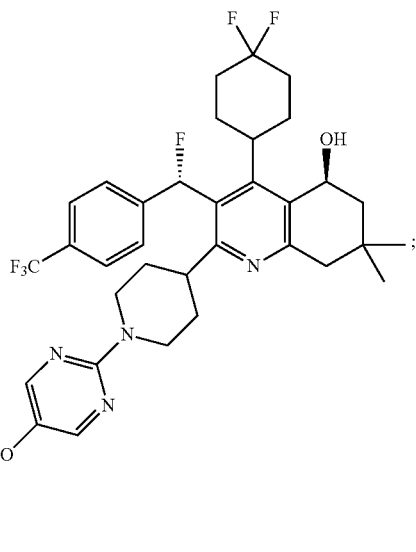

and (a-7) (5S)-2-{1-[5-(3-Carboxyphenyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol

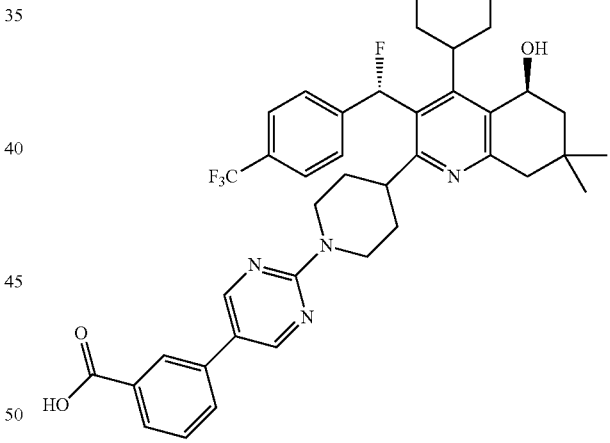

(a-6) (5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol The salt of the compound represented by general formula (I) or (I-1) of the present invention encompasses salts of compounds shown in (b-1) to (b-7) below:

(b-1) hydrochloric acid salt, hydrobromic acid salt, methanesulfonic acid salt, benzenesulfonic acid salt, succinic acid salt, fumaric acid salt or maleic acid salt of (5S)-4-(4,4-Difluorocyclohexyl)-2-[1-(5-{[(2S)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol;

(b-2) hydrochloric acid salt, hydrobromic acid salt, methanesulfonic acid salt, benzenesulfonic acid salt, succinic acid salt, fumaric acid salt or maleic acid salt of (5S)-4-(4,4-Difluorocyclohexyl)-2-[1-(5-{[(2R)-2,3-dihydroxypropyl]

oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol;

(b-3) hydrochloric acid salt, hydrobromic acid salt, methanesulfonic acid salt, benzenesulfonic acid salt, succinic acid salt, fumaric acid salt or maleic acid salt of (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol;

(b-4) hydrochloric acid salt, hydrobromic acid salt, methanesulfonic acid salt, benzenesulfonic acid salt, succinic acid salt, fumaric acid salt or maleic acid salt of (5S)-4-(4,4-Difluorocyclohexyl)-3-{(S)-fluoro[4-(trifluoromethyl)phenyl]methyl}-7,7-dimethyl-2-(1-{5-[3-(methylsulfonyl)propoxy]pyrimidin-2-yl}piperidin-4-yl)-5,6,7,8-tetrahydroquinolin-5-ol;

(b-5) hydrochloric acid salt, hydrobromic acid salt, methanesulfonic acid salt, benzenesulfonic acid salt, succinic acid salt, fumaric acid salt or maleic acid salt of (5S)-4-(4,4-Difluorocyclohexyl)-3-{(S)-fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol;

(b-6) hydrochloric acid salt, hydrobromic acid salt, methanesulfonic acid salt, benzenesulfonic acid salt, succinic acid salt, fumaric acid salt or maleic acid salt of (5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol; and (b-7) hydrochloric acid salt, hydrobromic acid salt, methanesulfonic acid salt, benzenesulfonic acid salt, succinic acid salt, fumaric acid salt or maleic acid salt of (5S)-2-{1-[5-(3-Carboxyphenyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol.

The salt of the compound represented by general formula (I) or (I-1) of the present invention encompasses each salt of each compound formed from a compound selected from the above-described (a-1) to (a-7) and an acid selected from the group consisting of hydrochloric acid, hydrobromic acid, methanesulfonic acid, benzenesulfonic acid, succinic acid, fumaric acid and maleic acid. The salt of the compound represented by general formula (I) or (I-1) of the present invention is preferably a particular salt (and a hydrate of the particular salt) described in each of Examples 1 to 21.

The salt of the compound represented by general formula (I) of the present invention may have optical isomers (including enantiomers and diastereomers) based on one or more asymmetric center(s), and these isomers and mixtures thereof are described by a single formula such as general formula (I). The present invention encompasses each of these isomers and mixtures thereof at any ratio (including racemates).

The compound represented by general formula (I) of the present invention encompasses a compound represented by general formula (I-1), (I-2), (I-3) or (I-4) or mixtures thereof (including racemates and diastereomer mixtures) and is preferably a compound represented by general formula (I-1) or (I-2) or mixtures thereof (including racemates), and more preferably a compound represented by general formula (I-1).

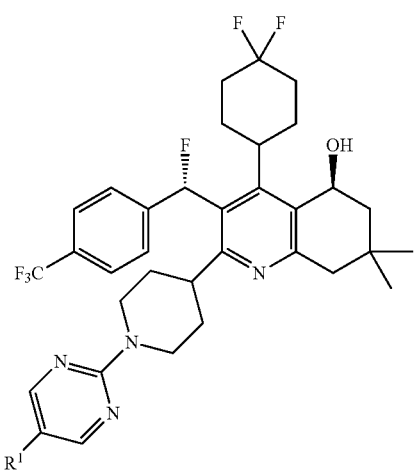

(I-1)

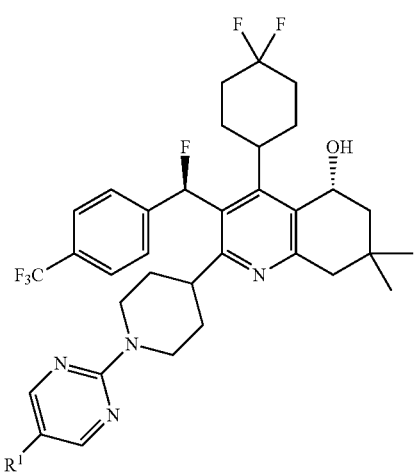

(I-2)

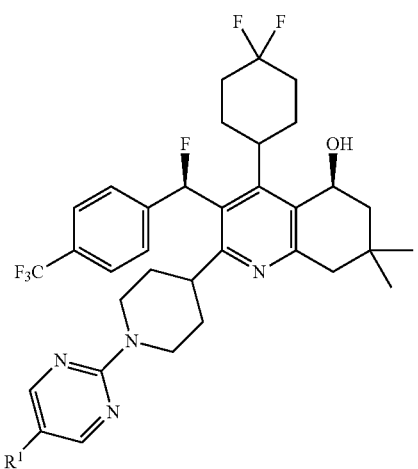

(I-3)

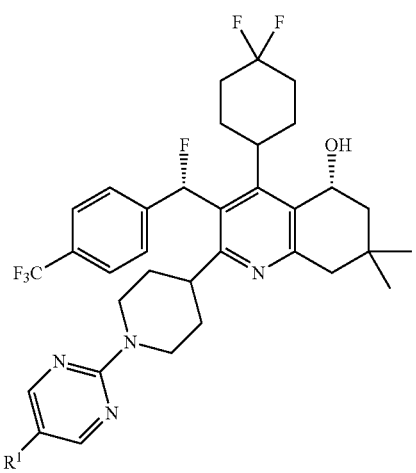

(I-4)

The compound represented by general formula (I-1) may contain a certain amount of a compound represented by general formula (I-2), (I-3) or (I-4). The "compound represented by general formula (I-1)" in the present invention encompasses "a compound represented by general formula (I-1) which contains a certain amount of a compound represented by general formula (I-2), (I-3) or (I-4)" and preferably encompasses "a compound represented by general formula (I-1) which contains a certain amount of a compound represented by general formula (I-2)", "a compound represented by general formula (I-1) which contains a certain amount of a compound represented by general formula (I-3)" and "a compound represented by general formula (I-1) which contains a certain amount of a compound represented by general formula (I-4)". In each case, the percentage content of each of the compounds represented by general formula (I-2), (I-3) or (I-4) in the compound represented by the general formula (I-1) may be for example, 5% or less, preferably 3% or less, more preferably 1% or less, further preferably 0.5% or less, further more preferably 0.3% or less, particularly preferably 0.1% or less, and most preferably 0.05% or less. The percentage content of each of the compounds represented by the general formulae (I-2), (I-3) or (I-4) may be calculated, for example, using the peak area ratio in high performance liquid chromatography (HPLC) or the weight ratio, and preferably the peak area ratio in HPLC.

The compound represented by general formula (I) or (I-1) of the present invention may form an acid addition salt in combination with an acid selected from the group consisting of hydrochloric acid, hydrobromic acid, methanesulfonic acid, benzenesulfonic acid, succinic acid, fumaric acid and maleic acid at any ratio. Each of the resulting salts or a mixture thereof is encompassed in the present invention. For example, hydrochloric acid salt encompasses salts that may be formed, such as monohydrochloride, dihydrochloride and trihydrochloride, and fumaric acid salt encompasses salts that may be formed, such as monofumarate and hemifumarate. In the compound names of the present invention, "mono acid salt" may be indicated as "acid salt" wherein "mono" in the name is omitted. For example, "monohydrochloride" may be indicated as "hydrochloride".

The salt of the compound represented by general formula (I) or (I-1) of the present invention encompasses any of (i) a salt formed from a compound represented by general formula (I) or (I-1) in which a basic group is protonated, and an acid from which a proton is dissociated; and (ii) an adduct formed from a compound represented by general formula (I) or (I-1) in which a basic group is not protonated, and an acid from which a proton is not dissociated. The "salt" of the present invention may mean any of the above-described (i) and (ii).

The salt of the compound represented by general formula (I) or (I-1) of the present invention may form a hydrate or a solvate. Each of these or a mixture thereof is encompassed in the present invention. The hydrate or the solvate formed by the salt of the compound represented by general formula (I) or (I-1) of the present invention in combination with water or a solvent at any ratio is encompassed in the present invention. For example, hydrates that may be formed, such as monohydrate, dihydrate and hemihydrate, and solvates that may be formed, such as monosolvate, disolvate and hemisolvate are encompassed in the present invention.

The salt of the compound represented by general formula (I) or (I-1) of the present invention may produce a plurality of crystals having different internal structures and physicochemical properties (crystal polymorphs) depending on reaction conditions and crystallization conditions. Each of these crystals or mixtures thereof at any ratio is encompassed in the present invention. In the case where a crystalline solid and an amorphous solid may coexist with each other, a mixture thereof at any ratio is encompassed in the present invention. Specifically, the crystal of the present invention having a particular crystalline form may contain a crystal having a different crystalline form or an amorphous solid. The percentage content of the particular crystalline form is preferably 50% or more, more preferably 80% or more, further preferably 90% or more, even more preferably 93% or more, particularly preferably 95% or more, and most preferably 97% or more.

In the present invention, the crystal refers to a solid having three-dimensional regular repeats of constituent atoms (or groups thereof) and is differentiated from an amorphous solid, which does not have such a regular internal structure. Whether a certain solid is crystalline or not can be examined by a well known crystallographic method (for example, powder X-ray crystallography, differential scanning calorimetry or the like). For example, the certain solid is subjected to powder X-ray crystallography using X-rays obtained by copper Kα radiation. The solid is determined to be crystalline when a distinctive peak is observed in its X-ray diffraction pattern, or determined to be amorphous when a distinctive peak is not observed therein. In the case where the peak can be read, but is not distinctive (for example, the peak is broad), the solid is determined to be a crystal having a low degree of crystallinity. Such crystals having a low degree of crystallinity are also encompassed in the crystal of the present invention.

In the powder X-ray crystallography using copper Kα rays, a sample is usually irradiated with copper Kα rays (in which Kα1 and Kα2 rays are not separated). The X-ray diffraction pattern can be obtained by analyzing diffraction derived from the Kα rays, and can also be obtained by analyzing only Kα1 ray-derived diffraction isolated from the diffraction derived from the Kα rays. In the present invention, the powder X-ray diffraction pattern obtained by Kα rays radiation encompasses an X-ray diffraction pattern obtained by analyzing diffraction derived from Kα rays, and an X-ray diffraction pattern obtained by analyzing diffraction derived from Kα1 rays and is preferably an X-ray diffraction pattern obtained by analyzing diffraction derived from Kα1 rays.

In the powder X-ray diffraction patterns of FIGS. 1 to 21 below, diffraction intensity [counts/sec (cps)] is shown on the vertical axis, and diffraction angle 2θ (degrees) is shown on the horizontal axis. The spacing d (Å) can be calculated according to the expression $2d \sin \theta = n\lambda$ wherein $n=1$. In this expression, the wavelength $\lambda$, of the $K\alpha$ rays is 1.54 Å, and the wavelength $\lambda$ of the $K\alpha 1$ rays is 1.541 Å. The positions (numeric values) and relative intensities of the spacing d may vary depending on measurement conditions, etc. Thus, the identity of a crystalline form can be recognized appropriately with reference to the whole pattern of a spectrum, even when the spacing d slightly differs.

The salt of the compound represented by general formula (I) or (I-1) of the present invention may be obtained as a crystal that exhibits, for example, a powder X-ray diffraction pattern as shown in any of FIGS. 1 to 21. These crystals may be identified on the basis of, for example, the spacing d corresponding to main peaks in each pattern. The main peaks in the powder X-ray diffraction pattern can be appropriately selected as characteristic peaks from, for example, peaks having relative intensity equal to or larger than an appropriately predetermined numeric value.

The salt of the compound represented by general formula (I) or (I-1) of the present invention may form an isotopic compound in which one or more atom(s) constituting the compound is substituted with an isotopic atom at non-natural ratio. The isotopic atom may be radioactive or non-radioactive, for example, deuterium ($^2$H; D), tritium ($^3$H; T), carbon-14 ($^{14}$C), iodine-125 ($^{125}$I) and the like. The radioactive or non-radioactive isotopic compound may be used as a medicament for treatment or prophylaxis of a disease, a reagent for research (for example, a reagent for assay), a diagnostic medicament (for example, an image diagnostic medicament) and the like. The present invention encompasses a radioactive or non-radioactive isotopic compound.

In the case where the compound represented by general formula (I) or (I-1) of the present invention has a group which may form an ester group such as a hydroxy group or a carboxy group, the compound may be converted to a pharmacologically acceptable ester and a salt thereof and the salt of this pharmacologically acceptable ester is encompassed in the present invention. The salt of the pharmacologically acceptable ester of the compound represented by general formula (I) or (I-1) may be a prodrug of the compound represented by general formula (I) or (I-1) and be decomposed in a metabolic process (for example, hydrolysis) when administered to a living body of a warm-blooded animal to produce the compound represented by general formula (I) or (I-1).

The group which may form an ester group with a hydroxy group may be, for example, aliphatic acyl [for example, ($C_1$-$C_{20}$ alkyl)carbonyl], aromatic acyl or alkoxycarbonyl [for example, ($C_1$-$C_6$ alkoxy)carbonyl]. The group which may form an ester group with a carboxy group may be, for example, aliphatic alkyl [for example, a $C_1$-$C_6$ alkyl], alkylcarbonyloxyalkyl [for example, ($C_1$-$C_6$ alkyl)carbonyloxy-($C_1$-$C_6$ alkyl)], cycloalkylcarbonyloxyalkyl [for example, ($C_3$-$C_8$ cycloalkyl)carbonyloxy-($C_1$-$C_6$ alkyl)], alkoxycarbonyloxyalkyl [for example, ($C_1$-$C_6$ alkoxy)carbonyloxy-($C_1$-$C_6$ alkyl)] or cycloalkyloxycarbonyloxyalkyl [for example, ($C_3$-$C_8$ cycloalkyl)oxycarbonyloxy-($C_1$-$C_6$ alkyl)].

The "dyslipidemia" in the present invention encompasses hyperlipidemia. The "arteriosclerosis" encompasses (i) arteriosclerosis due to various factors such as smoking and genetics (including multiple factors); and (ii) arteriosclerosis due to a disease which may cause arteriosclerosis such as dyslipidemia, low HDL cholesterolemia, high LDL cholesterolemia, a lipid-related disease, an inflammatory disease, diabetes, obesity or hypertension, and encompasses, for example, atherosclerosis, arteriolosclerosis, arteriosclerosis obliterans and atheromatous atherosclerosis. The "arteriosclerotic heart disease" represents a cardiovascular disease which develops due to arteriosclerosis as one of the causes. The "a coronary heart disease" represents a cardiovascular disease which develops due to arteriosclerosis or other diseases as one of the causes and encompasses, for example, heart failure, myocardial infarction, angina pectoris, cardiac ischemia, cardiovascular disorder or angioplasty-related restenosis. The "cerebrovascular disease" encompasses, for example, stroke or cerebral infarction. The "peripheral vascular disease" encompasses, for example, diabetic vascular complications.

The salt of the compound represented by general formula (I) or (I-1) of the present invention may be applied, without limitation, to treatment or prophylaxis of (i) a disease caused by a decrease in the blood concentration of HDL cholesterol, (ii) a disease caused by an increase in the blood concentration of LDL cholesterol, and (iii) a disease which can be treated or prevented by inhibition of CETP activity, besides the specific diseases as described above or described below.

In the case where the salt of the compound represented by general formula (I) or (I-1) of the present invention is used as a medicament, the salt may form a pharmaceutical composition in combination with other medicaments depending on the purpose. The pharmaceutical composition may be (i) a combination of a formulation which contains the salt of the compound represented by general formula (I) or (I-1) of the present invention as an active ingredient and a formulation which contains other medicaments as an active ingredient; or (ii) a single formulation (combination drug) which contains both the salt of the compound represented by general formula (I) or (I-1) of the present invention and other medicaments as an active ingredient, and is preferably the combination drug.

The pharmaceutical composition may be administered simultaneously or separately at an interval. In the case where the pharmaceutical composition is administered separately at an interval, the dosage form is not particularly limited as long as it is a dosage form in which the pharmaceutical composition may be administered separately at a different time. The time from administration of one active ingredient to administration of another active ingredient is not particularly limited and the other active ingredient is preferably administered within a time when the action of the previously administered active ingredient persists.

The other medicament which may be used in combination with the salt of the compound represented by general formula (I) or (I-1) of the present invention is not particularly limited as long as it has effects depending on the purpose thereof.

The nomenclature of the compound represented by general formula (I), (I-1), (I-2), (I-3) or (I-4) (including the compounds of the Examples) of the present invention and the intermediates for synthesizing them (including the intermediates in the Examples or the compounds of the Reference Examples) may be performed according to the nomenclature which is unified with the tetrahydroquinoline structure as a central scaffold or the nomenclature of IUPAC. Although compound names according to the two nomenclatures above may be different, each compound name correctly represents a compound specified by a described chemical structural formula.

The compound represented by general formula (I) of the present invention [hereinafter, also referred to as the compound (I); the same for other formulae] can be prepared according to Method A (Methods A-1, A-2, A-3 and A-4), Method B (Methods B-1 and B-2) or Method C described below.

Method A-1
Method A-2
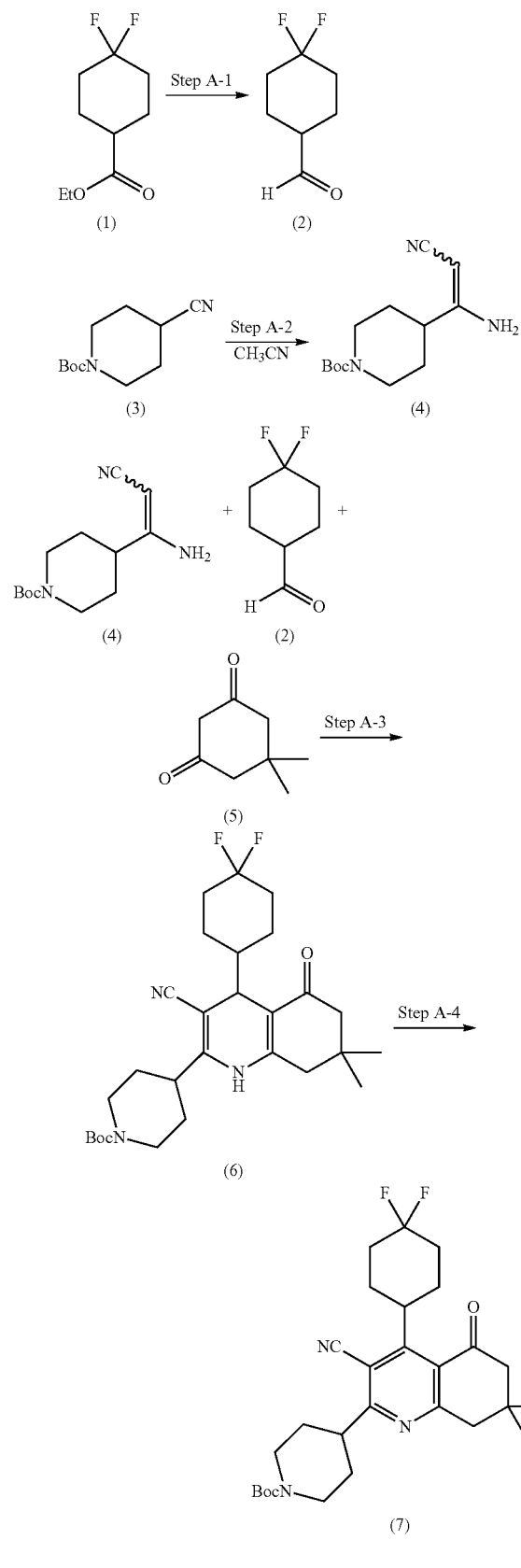
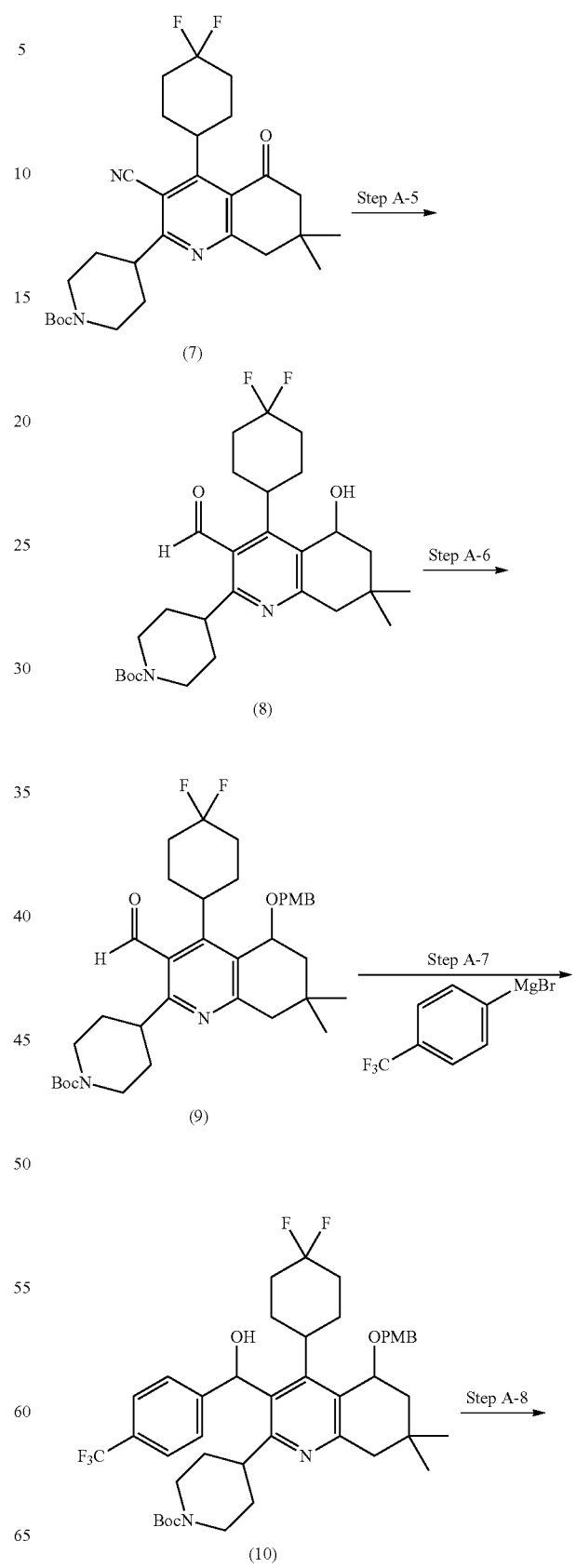

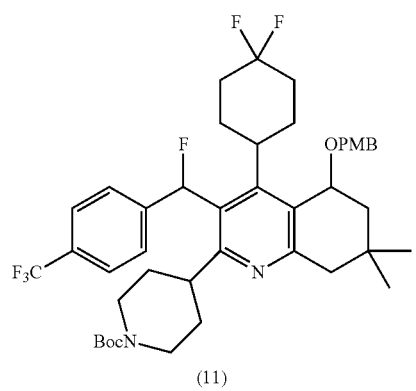
(11)
Method A-3
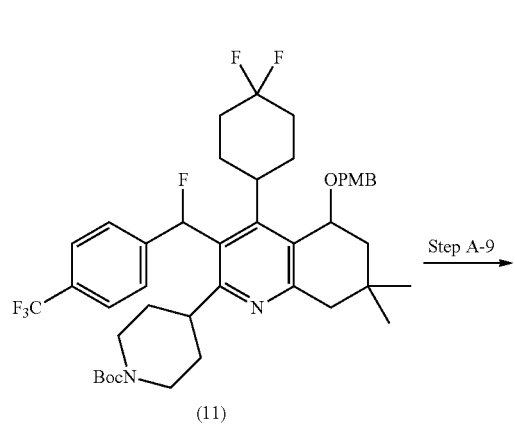
(11)
Step A-9
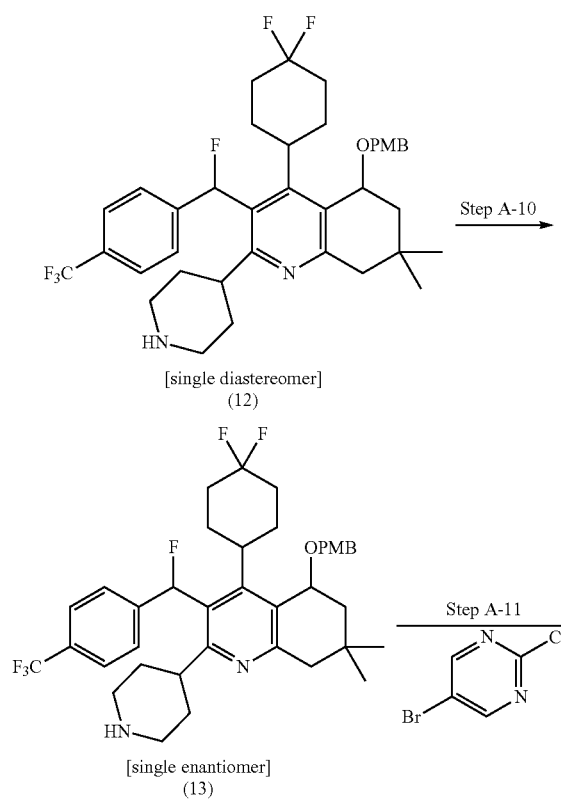
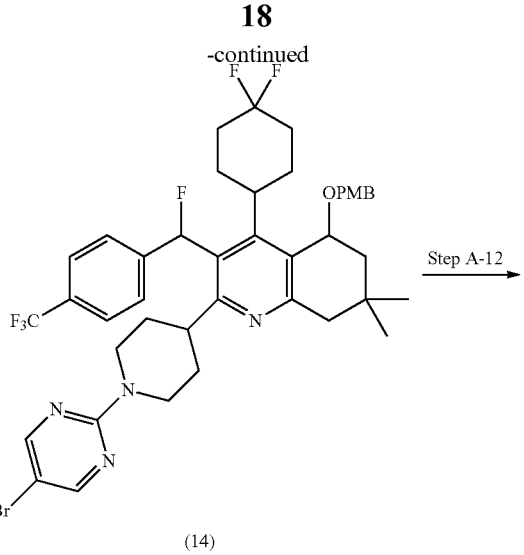
Step A-12
(14)
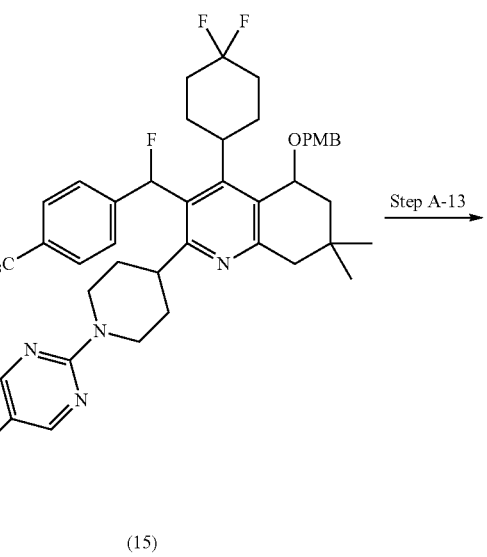
(15)
Method A-4
Step A-13
(15)

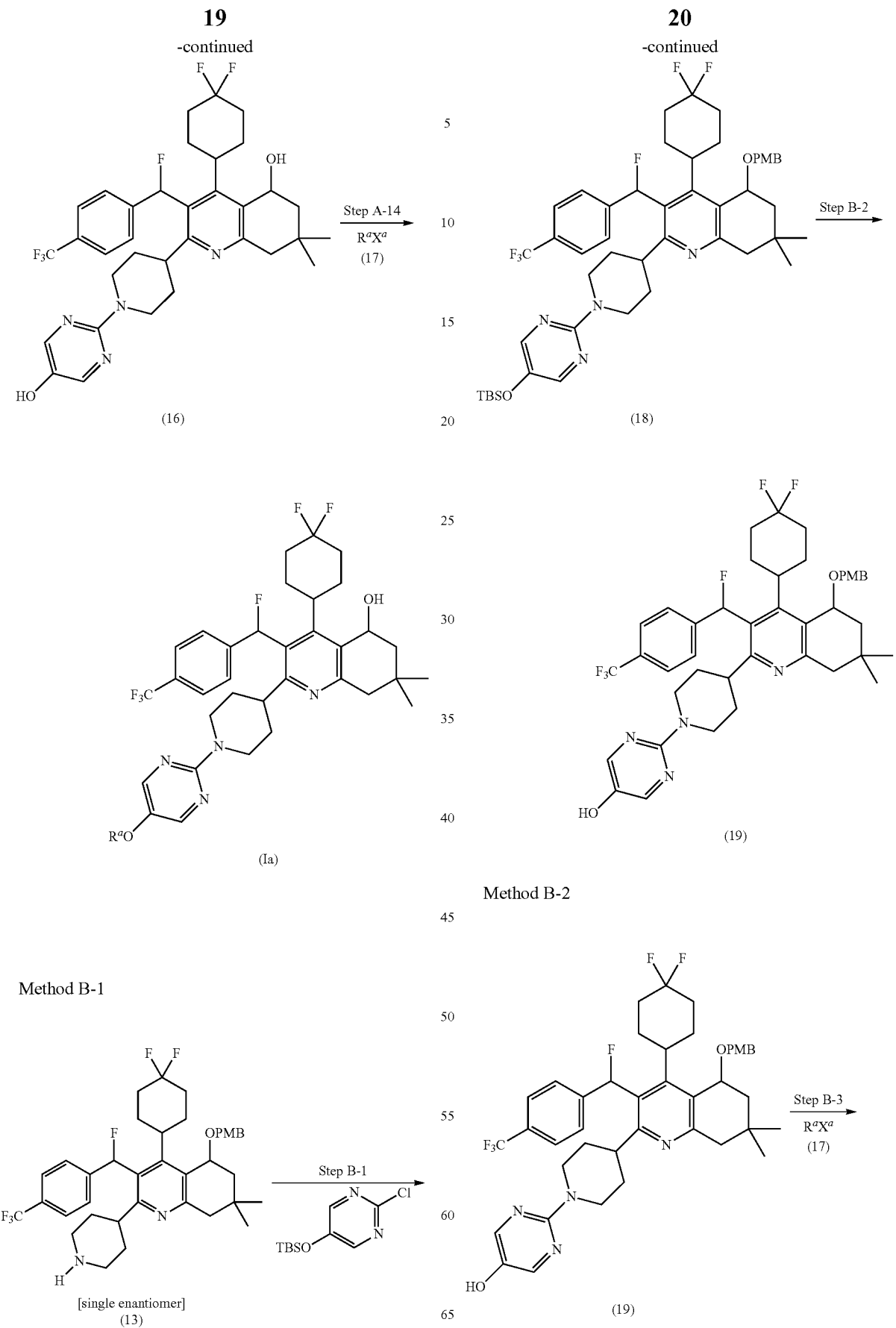

21
-continued

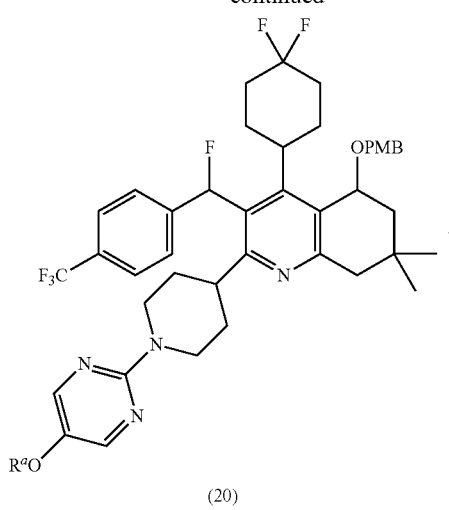
(20)

Step B-4 →

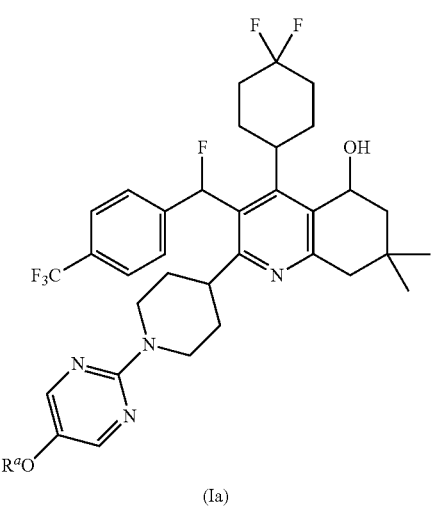
(Ia)

Method C

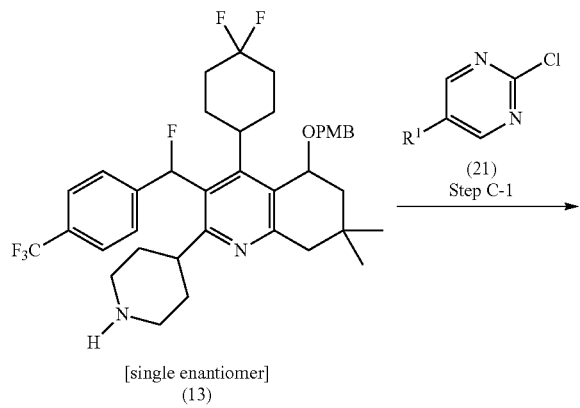
[single enantiomer]
(13)

22
-continued

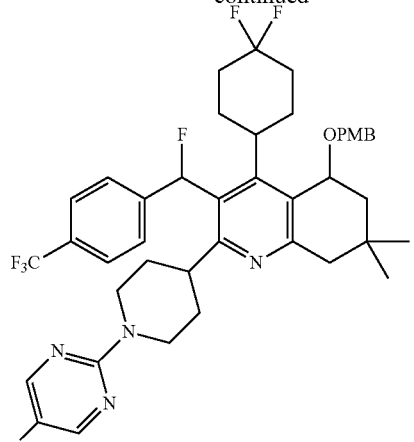
(22)

Step C-2 →

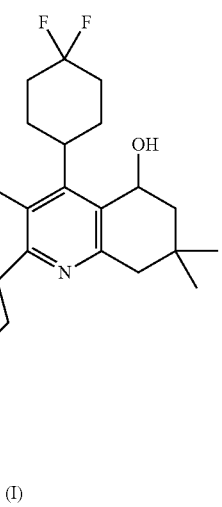
(I)

In the structural formulae of the compounds in the above-described Methods A to C, $R^1$ represents the same meanings as those in general formula (I); $R^a$ represents a (2S)-2,3-dihydroxypropyl group, a (2R)-2,3-dihydroxypropyl group, a 3-hydroxy-3-methylbutyl group, a 3-(methylsulfonyl)propyl group, a 3-hydroxy-2-(hydroxymethyl)propyl group or a 3-hydroxy-2-(hydroxymethyl)-2-methylpropyl group; the group represented by the formula $R^a$O-represents a (2S)-2,3-dihydroxypropyloxy group, a (2R)-2,3-dihydroxypropyloxy group, a 3-hydroxy-3-methylbutoxy group, a 3-(methylsulfonyl)propoxy group, a 3-hydroxy-2-(hydroxymethyl)propoxy group or a 3-hydroxy-2-(hydroxymethyl)-2-methylpropoxy group, which are defined in $R^1$; $X^a$ represents a chloro group, a bromo group, an iodo group, a methanesulfonyloxy group, a trifluoromethanesulfonyloxy group or a p-toluenesulfonyloxy group; Boc represents a tert-butoxycarbonyl group; PMB represents a p-methoxybenzyl group; and TBS represents a tert-butyldimethylsilyl group.

The acid used in the reaction of each step of Methods A to C described below is not particularly limited as long as it does not inhibit the reaction and is selected from the group of acids described below. The group of acids consists of organic acids such as acetic acid, propionic acid, trifluoroacetic acid or pentafluoropropionic acid; organic sulfonic acids such as p-toluenesulfonic acid, camphorsulfonic acid or trifluoromethanesulfonic acid; and inorganic acids such as hydrochloric acid, hydrobromic acid, hydroiodic acid, phosphoric acid, sulfuric acid or nitric acid.

The base used in the reaction of each step of Methods A to C described below is not particularly limited as long as it does not inhibit the reaction and is selected from the group of bases described below. The group of bases consists of alkali metal carbonates such as lithium carbonate, sodium carbonate, potassium carbonate or cesium carbonate; alkali metal hydrogencarbonates such as lithium hydrogencarbonate, sodium hydrogencarbonate or potassium hydrogencarbonate; alkali metal hydroxides such as lithium hydroxide, sodium hydroxide or potassium hydroxide; alkaline earth metal hydroxides such as calcium hydroxide or barium hydroxide; alkali metal hydrides such as lithium hydride, sodium hydride or potassium hydride; alkali metal amides such as lithium amide, sodium amide or potassium amide; alkali metal alkoxides such as lithium methoxide, sodium methoxide, sodium ethoxide, sodium tert-butoxide or potassium tert-butoxide; lithium alkyl amides such as lithium diisopropylamide; alkali metal silyl amides such as lithium bistrimethylsilyl amide or sodium bistrimethylsilyl amide; alkyl lithiums such as n-butyl lithium, sec-butyl lithium or tert-butyl lithium; and organic amines such as triethylamine, tributylamine, diisopropylethylamine, N-methylmorpholine, pyridine, picoline, lutidine, 4-(N,N-dimethylamino)pyridine, 4-pyrrolidinopyridine, quinoline, N,N-dimethylaniline, 1,5-diazabicyclo[4,3,0]non-5-ene (DBN), 1,4-diazabicyclo[2,2,2]octane (DABCO) or 1,8-diazabicyclo[5,4,0]undec-7-ene (DBU).

The solvent used in the reaction of each step of Methods A to C described below is not particularly limited as long as it does not inhibit the reaction and dissolves starting raw materials in part and, for example, is selected from the group of solvents described below. The group of solvents consists of aliphatic hydrocarbons such as hexane (for example, n-hexane), pentane (for example, n-pentane), heptane (for example, n-heptane), petroleum ether or cyclohexane; aromatic hydrocarbons such as benzene, toluene, xylene or ethyl benzene; halogenated hydrocarbons such as dichloromethane, chloroform, carbon tetrachloride, dichloroethane, chlorobenzene or dichlorobenzene; ethers such as diethyl ether, diisopropyl ether, tetrahydrofuran, 2-methyltetrahydrofuran, 1,4-dioxane, dimethoxyethane or diethylene glycol dimethyl ether; ketones such as acetone, methylethyl ketone, methylisobutyl ketone or cyclohexanone; esters such as methyl acetate, ethyl acetate, propyl acetate, isopropyl acetate or butyl acetate; nitriles such as acetonitrile, propionitrile, butyronitrile or isobutyronitrile; carboxylic acids such as acetic acid or propionic acid; alcohols such as methanol, ethanol, 1-propanol, 2-propanol, 1-butanol, 2-butanol, 2-methyl-1-propanol, 2-methyl-2-propanol (tert-butanol) or 1,2-propanediol; amides such as formamide, N,N-dimethylformamide, N,N-dimethylacetamide, 1-methyl-2-pyrrolidone, dimethylimidazolone or hexamethylphosphorotriamide; sulfoxides such as dimethyl sulfoxide; sulfones such as sulfolane; water; and a mixture thereof.

In the reaction of each step of Methods A to C described below, the reaction temperature varies depending on the solvent, starting raw materials, reagents or the like, and the reaction time varies depending on the solvent, starting raw materials, reagents, reaction temperature or the like.

In the reaction of each step of Methods A to C described below, the desired compound of each step may be isolated from the reaction mixture after the reaction completion according to a method which is well known in the field of organic chemistry. The desired compound is obtained, for example, by (i) filtering off insoluble materials such as a catalyst as necessary, (ii) adding water and a solvent which is immiscible with water (for example, dichloromethane, diethyl ether, ethyl acetate or the like) to the reaction mixture and extracting the desired compound, (iii) washing the organic layer with water and drying it with a desiccant such as anhydrous magnesium sulfate, and (iv) distilling off the solvent. The obtained desired compound may be further purified by a method which is well known in the field of organic chemistry (for example, recrystallization, reprecipitation, silica gel column chromatography or the like) as necessary. In addition, the desired compound of each step may be also used in the next reaction as it is without purification.

In the case where the compound as a starting raw material in the reaction of each step of Methods A to C described below has a group which inhibits the desired reactions such as an amino group, a hydroxy group and a carboxyl group, introduction of a protective group for such groups and removal of the introduced protective group may be performed suitably as necessary. Such a protective group is not particularly limited as long as it is a protective group usually used and may be, for example, a protective group described in T. W. Greene, P. G. Wuts, Greene's Protective Groups in Organic Synthesis, Fourth Edition, 2007, John Wiley & Sons, Inc. and the like. The introduction reaction of such a protective group and the removal reaction of the protective group may be performed according to a method which is well known in the field of organic chemistry (for example, a method as described in the above-described literature).

For example, in Method B, a compound (17) in which $R^a$ is a ((4R)-2,2-dimethyl-1,3-dioxolan-4-yl)methyl group, a ((4S)-2,2-dimethyl-1,3-dioxolan-4-yl)methyl group, a (2,2-dimethyl-1,3-dioxan-5-yl)methyl group or a (2,2,5-trimethyl-1,3-dioxan-5-yl)methyl group is used to obtain a compound (Ia) having the corresponding group $R^a$. This compound may be subjected to the removal reaction of the protective group to prepare a compound (Ia) in which the group represented by the formula $R^aO$— is a (2S)-2,3-dihydroxypropyloxy group, a (2R)-2,3-dihydroxypropyloxy group, a 3-hydroxy-2-(hydroxymethyl)propoxy group or a 3-hydroxy-2-(hydroxymethyl)-2-methylpropoxy group. For example, in Method C, a compound (21) in which $R^1$ is a ((4R)-2,2-dimethyl-1,3-dioxolan-4-yl)methoxy group, a ((4S)-2,2-dimethyl-1,3-dioxolan-4-yl)methoxy group, a (2,2-dimethyl-1,3-dioxan-5-yl)methoxy group, a (2,2,5-trimethyl-1,3-dioxan-5-yl)methoxy group or a 3-(methoxycarbonyl)phenyl group is used to obtain a compound (I) having the corresponding group $R^1$. This compound may be subjected to the removal reaction of the protective group to prepare a compound (I) in which $R^1$ is a (2S)-2,3-dihydroxypropyloxy group, a (2R)-2,3-dihydroxypropyloxy group, a 3-hydroxy-2-(hydroxymethyl)propoxy group, a 3-hydroxy-2-(hydroxymethyl)-2-methylpropoxy group or a 3-carboxyphenyl group.

In each step of Methods A to C described below (Steps A-5 to A-14 in Method A), isolation of a single diastereomer (a racemate) from a mixture of two kinds of diastereomers (a mixture of four kinds of enantiomers) may be performed by column chromatography, a crystallization method or the like and isolation of a single enantiomer from a single diastereomer (a racemate) may be performed by optically active column chromatography, a fractional crystallization method using an optically active compound (for example, an optically active carboxylic acid compound or an optically active amine compound) or the like. Isolation of a single enantiomer from a mixture of two kinds of diastereomers (a mixture of four kinds of enantiomers) may be performed by optically active column chromatography in any step.

In the examples shown in Methods A to C described below, isolation of a single diastereomer (a racemate) from a mixture of two kinds of diastereomers is performed in Step A-7 and isolation of a single enantiomer from a single diastereomer (a racemate) is performed in Step A-10. The compounds (10), (11) and (12) are the single diastereomers (racemates) described in Reference Examples 7, 8 and 9, respectively and the compound (13) is the single enantiomer described in Reference Example 10. The compounds (14), (15), (16), (18), (19), (20), (22), (Ia) and (I) which are prepared from the compound (13) are single enantiomers.

Isolation of a single diastereomer (a racemate) and isolation of a single enantiomer are not limited to the above-described examples and may be performed in any step (the same or different step) of Methods A to C, respectively. For example, in the case where isolation of a single diastereomer (a racemate) is not performed in Step A-7, Steps A-8 to A-9, Steps A-11 to A-14, Steps B-1 to B-4 or Steps C-1 to C-2 may be performed respectively using a mixture of two kinds of diastereomers as a raw material. In the case where isolation of a single diastereomer (a racemate) is performed in any one of the above-described steps, the steps following those may be performed respectively using the single diastereomer (a racemate) as a raw material. In the case where isolation of a single enantiomer is further performed in any one of the above-described steps, the step following those may be performed respectively using the single enantiomer as a raw material and the compound (I) [preferably the compound (I-1)] as a single enantiomer is obtained. In the case where only isolation of a single diastereomer (a racemate) is performed in any one of the above-described steps, the compound (I) as a single diastereomer (a racemate) is obtained and the compound (I) [preferably, the compound (I-1)] as a single enantiomer is obtained by further performing isolation of a single enantiomer. In the case where isolation of a single diastereomer (a racemate) and isolation of a single enantiomer are not performed in any one of the above-described steps, the compound (I) as a mixture of two kinds of diastereomers is obtained and the compound (I) [preferably, the compound (I-1)] as a single enantiomer is obtained by performing isolation of a single diastereomer (a racemate) and isolation of a single enantiomer.

Hereinafter, the reaction of each step of Methods A to C is described.
(Method A)

Method A is a method of preparing the compound (Ia) which is encompassed in the compound (I).
(Step A-1)

Step A-1 is a step of preparing the compound (2) by reducing the compound (1). The compound (1) is known.

The reduction reagent to be used is not limited as long as it may be used in the reduction reaction of an alkoxycarbonyl group to a formyl group and is preferably diisobutyl aluminum hydride.

The solvent to be used is preferably an aromatic hydrocarbon, and more preferably toluene.

The reaction temperature is preferably −100° C. to 0° C.
The reaction time is preferably 30 minutes to 12 hours.
(Step A-2)

Step A-2 is a step of preparing the compound (4) by reacting the compound (3) with acetonitrile in the presence of a base. The compound (3) is known.

A protective group which is well known in the field of organic chemistry may be used as the protective group of the amino group in the compound (3) instead of the tert-butoxycarbonyl group (for example, T. W. Greene, P. G. Wuts, Greene's Protective Groups in Organic Synthesis, Fourth Edition, 2007, John Wiley & Sons, Inc.).

The base to be used is preferably a lithium alkyl amide, and more preferably lithium diisopropylamide.

The solvent to be used is preferably an aliphatic hydrocarbon, an aromatic hydrocarbon, an ether or a mixture thereof, and more preferably n-heptane, ethylbenzene, tetrahydrofuran or a mixture thereof.

The reaction temperature is preferably −78° C. to 50° C.
The reaction time is preferably 30 minutes to 48 hours.
(Step A-3)

Step A-3 is a step of preparing the compound (6) by reacting the compounds (2) and (4) and then reacting the compound (5). The compound (5) is known. An excess amount of the compound (5) may be used in Step A-3.

The solvent to be used is preferably an aromatic hydrocarbon, and more preferably toluene.

The reaction temperature is preferably 50° C. to 150° C.
The reaction time is preferably 30 minutes to 48 hours.
(Step A-4)

Step A-4 is a step of preparing the compound (7) by oxidizing the compound (6).

The oxidation reagent to be used is not limited as long as it may be used in the oxidation reaction of a dihydropyridyl group to a pyridyl group, and is preferably 2,3-dichloro-5,6-dicyano-p-benzoquinone (DDQ).

The solvent to be used is preferably a halogenated hydrocarbon, and more preferably dichloromethane.

The reaction temperature is preferably 0° C. to 50° C.
The reaction time is preferably 30 minutes to 12 hours.
(Step A-5)

Step A-5 is a step of preparing the compound (8) by reducing the compound (7).

The reduction reagent to be used is not limited as long as it may be used in the reduction reaction of a cyano group to a formyl group and is preferably diisobutyl aluminum hydride.

The solvent to be used is preferably an aromatic hydrocarbon, and more preferably toluene.

The reaction temperature is preferably −100° C. to 0° C.
The reaction time is preferably 30 minutes to 12 hours.
(Step A-6)

Step A-6 is a step of preparing the compound (9) by reacting the compound (8) with p-methoxybenzyl bromide in the presence of a base.

The base to be used is not limited as long as it may be used in the alkylation reaction of a hydroxy group and is preferably an alkali metal hydride, and more preferably sodium hydride.

The solvent to be used is preferably an amide, and more preferably N,N-dimethylformamide.

The reaction temperature is preferably −50° C. to 50° C.
The reaction time is preferably 30 minutes to 12 hours.

In Step A-6, a protective group which is well known in the field of organic chemistry may be used as the protective group of the hydroxy group instead of the p-methoxybenzyl group (for example, T. W. Greene, P. G. Wuts, Greene's Protective Groups in Organic Synthesis, Fourth Edition, 2007, John Wiley & Sons, Inc.).
(Step A-7)

Step A-7 is a step of preparing the compound (10) by reacting the compound (9) with 4-trifluoromethylphenyl magnesium bromide. 4-Trifluoromethylphenyl magnesium bromide can be prepared from 4-trifluoromethylphenyl bromide and magnesium by a method which is well known in the field of organic chemistry.

The solvent to be used is preferably an ether, and more preferably tetrahydrofuran.

The reaction temperature is preferably −20° C. to 50° C.
The reaction time is preferably 30 minutes to 12 hours.

In Step A-7, the compound (10) has two asymmetric carbon atoms (the carbon atoms to which a hydroxy group or a p-methoxybenzyloxy group is bonded) and may be obtained as a mixture of stereoisomers (a mixture of four kinds of optical isomers, namely, a mixture of diastereomers). The diastereomer mixture obtained in Step A-7 may be isolated into single diastereomer compounds depending on the properties of the mixture. This isolation may be performed by a method which is well known in the field of organic chemistry (for example, separation by column chromatography or fractional crystallization of a diastereomer mixture). Each of the isolated diastereomer compounds (a mixture of enantiomers) may be isolated into single enantiomer compounds depending on the properties of the compound. This isolation may be performed by a method which is well known in the field of organic chemistry (for example, optical resolution by column chromatography or fractional crystallization with formation of diastereomer salt). In Step A-7, this is the same in the case of the compound which is obtained using a protective group other than the p-methoxybenzyloxy group and the tert-butoxycarbonyl group as the two protective groups in the compound (9). This is the same in the case of the compound (11) which is obtained in Step A-8.

(Step A-8)

Step A-8 is a step of preparing the compound (11) by reacting the compound (10) with a fluorination reagent.

The fluorination reagent to be used is not limited as long as it may be used in the fluorination reaction of a hydroxy group and is preferably bis(methoxyethyl)aminosulfur trifluoride [Deoxo-Fluor (trade name)].

The solvent to be used is preferably a halogenated hydrocarbon, and more preferably dichloromethane.

The reaction temperature is preferably −100° C. to 0° C.

The reaction time is preferably 30 minutes to 24 hours.

(Step A-9)

Step A-9 is a step of preparing the compound (12) by reacting the compound (11) with zinc bromide.

The solvent to be used is preferably a halogenated hydrocarbon, and more preferably dichloromethane.

The reaction temperature is preferably 0° C. to 50° C.

The reaction time is preferably 1 hour to 5 days.

The diastereomer mixture obtained in Step A-9 may be isolated into single diastereomer compounds and the compound (12) may be obtained as a single diastereomer compound.

The removal reaction of the tert-butoxycarbonyl group in Step A-9 may be also performed by a method which is well known in the field of organic chemistry (for example, T. W. Greene, P. G. Wuts, Greene's Protective Groups in Organic Synthesis, Fourth Edition, 2007, John Wiley & Sons, Inc.).

(Step A-10)

Step A-10 is a step of obtaining the compound (13) as a single enantiomer by subjecting the compound (12) to optical resolution by optically active column chromatography.

The optically active column and the resolution conditions to be used are not limited as long as they can achieve optical resolution of the compound (12) and are preferably those described in Reference Example 10.

(Step A-11)

Step A-11 is a step of preparing the compound (14) by reacting the compound (13) with 5-bromo-2-chloropyrimidine in the presence of a base.

The base to be used is preferably an organic amine, and more preferably diisopropylethylamine or 1,8-diazabicyclo[5,4,0]undeca-7-ene (DBU).

The solvent to be used is preferably an ether or an amide, and more preferably 1,4-dioxane.

The reaction temperature is preferably 20° C. to 150° C.

The reaction time is preferably 30 minutes to 12 hours.

(Step A-12)

Step A-12 is a step of preparing the compound (15) by reacting the compound (14) with morpholine in the presence of a palladium catalyst, a phosphorus reagent and a base.

The palladium catalyst to be used is not limited as long as it may be used in the amination reaction on the aromatic ring and may be, for example, a palladium catalyst described in J. Tsuji, Palladium Reagents and Catalysis: New Perspectives for the 21st Century, 2004, John Wiley & Sons, Inc and the like. The palladium catalyst to be used is preferably tetrakis(triphenyl phosphine) palladium (0), tris(dibenzylidene acetone) dipalladium (0), palladium (II) chloride, palladium (II) acetate or palladium (II) dichlorobis(triphenyl phosphine), and more preferably palladium (II) acetate.

The phosphorus reagent to be used is not limited as long as it may be used in the amination reaction on the aromatic ring and is preferably 2-(di-tert-butylphosphino)biphenyl, 2-(dicyclohexylphosphino)biphenyl, 2-dicyclohexylphosphino-2',4',6'-triisopropylbiphenyl, 5-(di-tert-butylphosphino)-1',3',5'-triphenyl-1'H-[1,4']bipyrazole, cyclohexyl phosphine, 1,2,3,4,5-pentaphenyl-1'-(di-tert-butylphosphino)ferrocene or 2-(diphenylphosphino)-2'-(N,N-dimethylamino)biphenyl, and more preferably 2-dicyclohexylphosphino-2',4',6'-triisopropylbiphenyl.

The base to be used is preferably an alkali metal alkoxide, and more preferably sodium tert-butoxide.

The solvent to be used is preferably an aromatic hydrocarbon, an alcohol or a mixture thereof, and more preferably toluene, 2-methyl-2-propanol or a mixture thereof.

The reaction temperature is preferably 20° C. to 150° C.

The reaction time is preferably 30 minutes to 12 hours.

(Step A-13)

Step A-13 is a step of preparing the compound (16) by treating the compound (15) with an acid.

The acid to be used is preferably an inorganic acid, and more preferably hydrochloric acid.

The solvent to be used is preferably an ether, an alcohol or a mixture thereof, and more preferably 1,4-dioxane, methanol or a mixture thereof.

The reaction temperature is preferably 20° C. to 150° C.

The reaction time is preferably 30 minutes to 6 hours.

(Step A-14)

Step A-14 is a step of preparing the compound (Ia) by reacting the compound (16) with the compound (17) in the presence of a base. The compound (17) is known or may be easily prepared from a known compound.

The base to be used is preferably an alkali metal carbonate, and more preferably cesium carbonate or potassium carbonate.

The solvent to be used is preferably an ether or an amide, and more preferably tetrahydrofuran, N,N-dimethylformamide or 1-methyl-2-pyrrolidone.

The reaction temperature is preferably 0° C. to 100° C.

The reaction time is preferably 30 minutes to 50 hours.

(Method B)

Method B is a method of preparing the compound (Ia) which is encompassed in the compound (I).

(Step B-1)

Step B-1 is a step of preparing the compound (18) by reacting the compound (13) with 2-chloro-5-(tert-butyldimethylsilyloxy)pyrimidine in the presence of a base.

The base to be used is preferably an alkali metal carbonate or an organic amine, and more preferably potassium carbonate.

The solvent to be used is preferably an aromatic hydrocarbon, an ether, an alcohol or an amide, and more preferably 1,4-dioxane.

The reaction temperature is preferably 80° C. to 160° C.

The reaction time is preferably 1 hour to 96 hours.

(Step B-2)

Step B-2 is a step of preparing the compound (19) by removing the tert-butyldimethylsilyl group in the compound (18) in the presence of a desilylation reagent.

The desilylation reagent to be used is not limited as long as it may be used in a desilylation reaction and may be preferably an inorganic acid such as hydrochloric acid-dioxane, an organic acid such as acetic acid or trifluoroacetic acid, a fluorine compound such as sodium fluoride or potassium fluoride, or a fluorine-containing ammonium salt such as tetrabutylammonium fluoride, and more preferably tetrabutylammonium fluoride.

The solvent to be used is preferably a halogenated hydrocarbon, an ether, water or a mixture thereof, and more preferably tetrahydrofuran.

The reaction temperature is preferably 0° C. to 60° C.

The reaction time is preferably 5 minutes to 6 hours.

(Step B-3)

Step B-3 is a step of preparing the compound (20) by reacting the compound (19) with the compound (17) in the presence of a base. The compound (17) is known or may be easily prepared from a known compound.

Step B-3 may be performed according to a method similar to that of Step A-14.

(Step B-4)

Step B-4 is a step of preparing the compound (Ia) by removing the p-methoxybenzyl group in the compound (20) in the presence of an acid.

The acid to be used is preferably an organic acid or an inorganic acid, and more preferably hydrochloric acid.

The solvent to be used is preferably a halogenated hydrocarbon, an ether or an alcohol, and more preferably 1,4-dioxane.

The reaction temperature is preferably 0° C. to 100° C.

The reaction time is preferably 30 minutes to 48 hours.

The removal reaction of the p-methoxybenzyl group in Step B-4 may be also performed by a method which is well known in the field of organic chemistry (for example, T. W. Greene, P. G. Wuts, Greene's Protective Groups in Organic Synthesis, Fourth Edition, 2007, John Wiley & Sons, Inc.).

(Method C)

Method C is a method of preparing the compound (I).

(Step C-1)

Step C-1 is a step of preparing the compound (22) by reacting the compound (13) with the compound (21) in the presence of a base. The compound (21) is known, may be easily prepared from a known compound or may be prepared according to the Reference Examples. Step C-1 may be also performed using a palladium catalyst, a phosphorus reagent and a base which are similar to those in Step A-12.

The base to be used is preferably an alkali metal carbonate or an organic amine, and more preferably potassium carbonate, diisopropylethylamine, 1,8-diazabicyclo[5,4,0]undec-7-ene (DBU) or a mixture thereof.

The solvent to be used is preferably an ether, an alcohol or an amide, and more preferably 1,4-dioxane, 2-propanol, 2-methyl-2-propanol, N,N-dimethylformamide or 1-methyl-2-pyrrolidone.

The reaction temperature is preferably 20 to 160° C.

The reaction time is preferably 30 minutes to 96 hours.

Step C-1 may be performed under microwave irradiation.

(Step C-2)

Step C-2 is a step of preparing the compound (I) by removing the p-methoxybenzyl group in the compound (22) in the presence of an acid.

Step C-2 may be performed according to a method similar to that of Step B-4.

The salt of the compound represented by general formula (I) of the present invention may be prepared by the method described below, for example:

(i) dissolving the compound represented by general formula (I) of the present invention in a solvent (for example, dichloromethane, acetone, ethyl acetate or the like);

(ii) adding an acid to the reaction solution and stirring the reaction mixture;

(iii) performing heating and cooling of the reaction mixture, distillation of the solvent, addition of a poor solvent or addition of a seed crystal of a desired salt compound as necessary; and (iv) obtaining precipitated solid by filtration.

When the salt of the compound represented by general formula (I) or (I-1) of the present invention is used as a medicament, it may be administered (i) as a bulk powder as it is; (ii) orally as a formulation such as a tablet, a capsule, granules, a powder or a syrup, which is prepared by mixing with a suitable pharmacologically acceptable excipient, diluent or the like; or (iii) parenterally as a formulation such as an injection or a suppository, which is prepared as described above. It is preferably orally administered.

These formulations are prepared by well-known methods using additives such as an excipient, a binder, a disintegrant, a lubricant, an emulsifier, a stabilizer, a flavoring agent, a diluent or a solvent for injection.

The excipient may be, for example, an organic excipient or an inorganic excipient. The organic excipient may be, for example, a sugar derivative such as lactose, sucrose, glucose, mannitol or sorbitol; a starch derivative such as corn starch; a cellulose derivative such as crystalline cellulose; gum arabic; dextran; pullulan; or the like. The inorganic excipient may be, for example, a silicic acid salt derivative such as light anhydrous silicic acid, synthesized aluminum silicate; a sulfuric acid salt such as calcium sulfate; or the like.

The binder may be, for example, the compounds shown in the above-described excipient; gelatin; polyvinyl pyrrolidone; polyethylene glycol; or the like.

The disintegrant may be, for example, the compounds shown in the above-described excipient; a chemically modified starch or cellulose derivative such as sodium croscarmellose or sodium carboxymethyl starch; cross-linked polyvinyl pyrrolidone; or the like.

The lubricant may be, for example, talc; colloidal silica; waxes such as beeswax or sperm whale; glycol; D, L-leucine; a sulfuric acid salt such as sodium sulfate; the starch derivatives in the above-described excipient; or the like.

The emulsifier may be, for example, a colloidal clay such as bentonite or begum; an anionic surfactant such as lauryl sodium sulfate; a cationic surfactant such as benzalkonium chloride; a non-ionic surfactant such as polyoxyethylene alkyl ether; or the like.

The stabilizer may be, for example, a parahydroxybenzoic acid ester such as methyl paraben; an alcohol such as chlorobutanol; benzalkonium chloride; phenol; thimerosal; or the like.

The flavoring agent may be, for example, a sweetener, an acidulant, a fragrance or the like, which are usually used.

The diluent may be, for example, water, ethanol, propylene glycol or the like.

The solvent for injection may be, for example, water, ethanol, glycerin or the like.

The dosage amount of the salt of the compound represented by general formula (I) or (I-1) which is an active ingredient of the invention varies depending on symptoms, age and the like of a patient. The salt of the compound represented by general formula (I) or (I-1) may be administered depending on symptoms, 1 to 6 times per one day for an adult human, at 0.01 mg/kg (preferably 0.05 mg/kg) as lower limit and at 500 mg/kg (preferably 50 mg/kg) as upper limit per dose when orally administered, or at 0.001 mg/kg (preferably 0.005 mg/kg) as lower limit and at 50 mg/kg (preferably 5 mg/kg) as upper limit per dose when parenterally administered.

Effect of the Invention

The salt of the compound represented by general formula (I) or (I-1) of the present invention has excellent properties in terms of CETP inhibition activity, increasing action on the concentration of HDL cholesterol, decreasing action on the concentration of LDL cholesterol, rapid onset of pharmacological effect, prolonged pharmacological effect, physical stability, solubility, oral absorbability, blood concentration, cell membrane permeability, metabolic stability, tissue migration, bioavailability (BA), drug-drug interaction, toxicity or the like, and is useful as a medicament for a warm-blooded animal (particularly, for a human). The above-described medicament is a medicament for treatment or prophylaxis of, preferably, dyslipidemia, hypercholesterolemia, low HDL cholesterolemia, high LDL cholesterolemia, hypertriglyceridemia, arteriosclerosis, arteriosclerotic heart disease, coronary heart disease (including heart failure, myocardial infarction, angina pectoris, cardiac ischemia, cardiovascular disorder and angioplasty-related restenosis), cerebrovascular disease (including stroke and cerebral infarction), peripheral vascular disease (including diabetic vascular complications) or obesity, more preferably dyslipidemia, low HDL cholesterolemia, high LDL cholesterolemia, arteriosclerosis, arteriosclerotic heart disease or coronary heart disease, further preferably dyslipidemia, low HDL cholesterolemia, arteriosclerosis or coronary heart disease, and even more preferably low HDL cholesterolemia or arteriosclerosis.

BEST MODE FOR CARRYING OUT THE INVENTION

Figure 1:
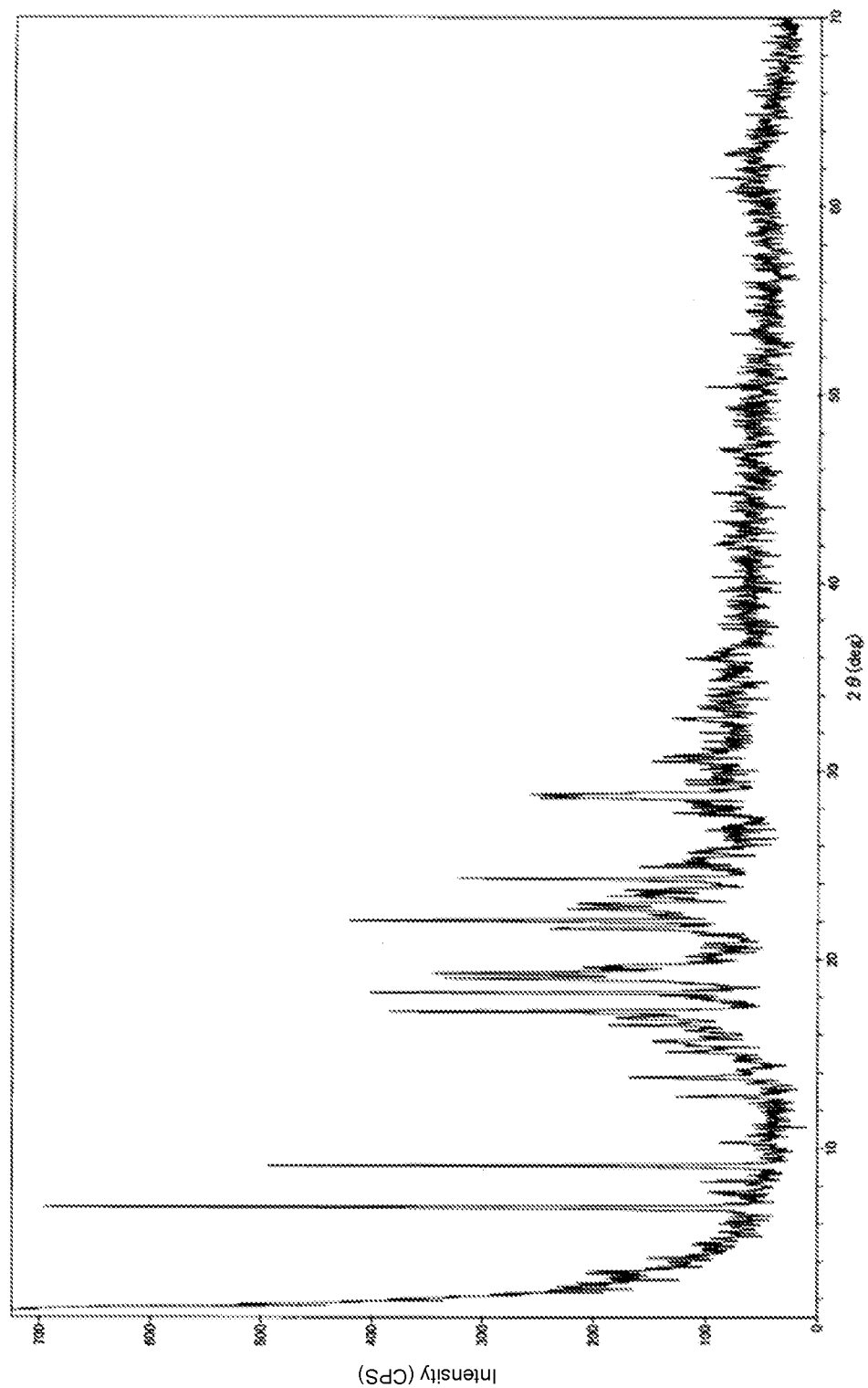
FIG. 1 shows an X-ray diffraction pattern exhibited by a crystal of a salt of a compound obtained in Example 1.

Hereinafter, the present invention is further explained in detail with Examples, Reference Examples, Test Examples and Formulation Examples. However, the scope of the present invention is not limited thereto.

The abbreviations described below are used in the Examples and Reference Examples.
Boc: tert-butoxycarbonyl;
PMB: p-methoxybenzyl;
TBS: tert-butyldimethylsilyl.

EXAMPLES

Example 1

(5S)-4-(4,4-Difluorocyclohexyl)-3-{(S)-fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol dihydrochloride To a solution of 0.70 g (0.95 mmol) of (5S)-4-(4,4-Difluorocyclohexyl)-3-{(S)-fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol, which was prepared by a method similar to that of Reference Example 22, in 4.8 ml of ethyl acetate, 0.17 ml (2.0 mmol) of 35% hydrochloric acid was added dropwise with stirring at 60° C. Then, the reaction mixture was cooled to 20° C. and stirred for 3 hours. The precipitated solid was obtained by filtration, washed with 5 ml of ethyl acetate twice and then dried under reduced pressure at 60° C. to provide 659 mg of the title compound as a white powder (yield: 86%).

$^1$H-NMR spectrum (300 MHz, CD$_3$OD) δ: 8.34 (2H, s), 7.88-7.80 (2H, m), 7.60-7.38 (3H, m), 5.35-5.25 (1H, m), 4.73-4.62 (1H, m), 4.44-4.32 (1H, m), 4.13 (2H, d, J=5.6 Hz), 4.02-3.88 (1H, m), 3.73 (2H, dd, J=11.0, 5.9 Hz), 3.68 (2H, dd, J=11.0, 6.3 Hz), 3.42-3.29 (1H, m), 3.20-2.95 (3H, m), 2.54-1.65 (15H, m), 1.21 (3H, s), 1.08 (3H, s), 0.98-0.84 (1H, m).

Mass spectrum (FAB+, m/z): 737 [(M+1)$^+$].
Mass spectrum (FAB−, m/z): 35, 37 [Cl$^−$].
Anal. Calcd for C$_{38}$H$_{48}$N$_4$O$_4$F$_6$Cl$_2$: Cl, 8.76. Found: Cl, 8.62.

Example 2

(5S)-4-(4,4-Difluorocyclohexyl)-3-{(S)-fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol dihydrobromide

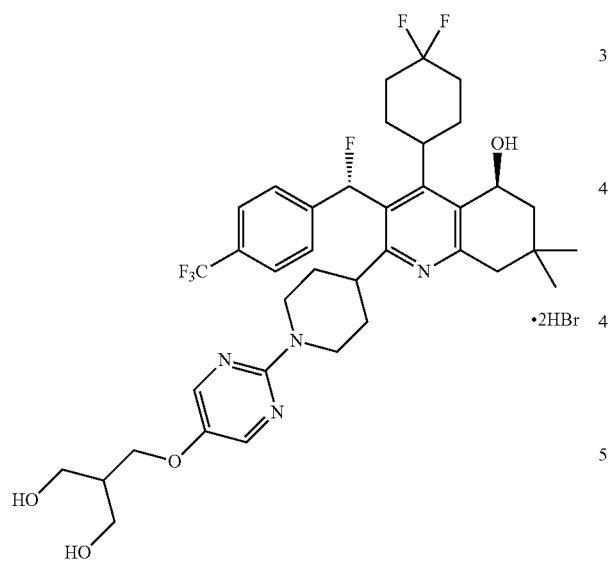

Reactions similar to those of Example 1 were performed except for using 0.22 ml of 47% hydrobromic acid instead of 35% hydrochloric acid, and from 0.70 g (0.95 mmol) of (5S)-4-(4,4-Difluorocyclohexyl)-3-{(S)-fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol, which was prepared by a method similar to that of Reference Example 22, 741 mg of the title compound was obtained as a white powder (yield: 88%).

$^1$H-NMR spectrum (300 MHz, CD$_3$OD) δ: 8.32 (2H, s), 7.87-7.80 (2H, m), 7.60-7.39 (3H, m), 5.34-5.26 (1H, m), 4.74-4.63 (1H, m), 4.44-4.32 (1H, m), 4.13 (2H, d, J=5.6 Hz), 4.03-3.87 (1H, m), 3.73 (2H, dd, J=11.0, 5.9 Hz), 3.68 (2H, dd, J=11.0, 6.3 Hz), 3.41-3.25 (1H, m), 3.24-2.92 (3H, m), 2.51-1.67 (15H, m), 1.22 (3H, s), 1.08 (3H, s), 0.98-0.85 (1H, m).

Mass spectrum (FAB+, m/z): 737 [(M+1)$^+$].
Mass spectrum (FAB−, m/z): 79, 81 [Br$^−$].
Anal. Calcd for C$_{38}$H$_{48}$N$_4$O$_4$F$_6$Br$_2$: Br, 17.78. Found: Br, 17.49.

Example 3

(5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol dihydrobromide

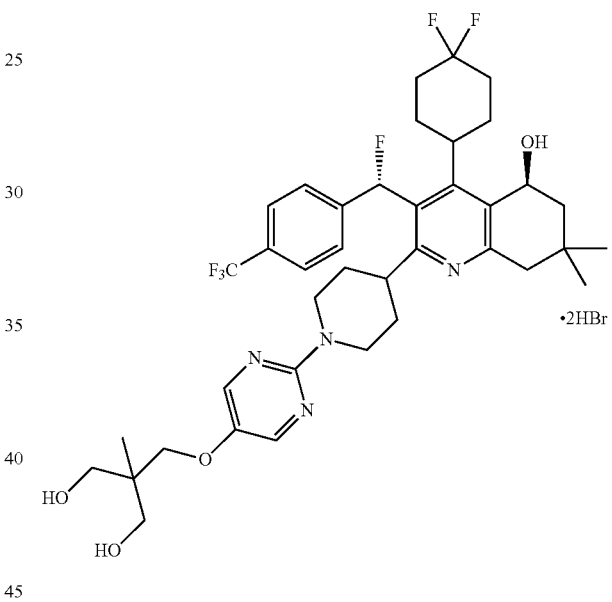

To a solution of 50.7 mg (0.0675 mmol) of (5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol, which was prepared by a method similar to that of Reference Example 19, in 0.5 ml of methyl ethyl ketone, 15 μl (0.13 mmol) of 47% hydrobromic acid was added dropwise with stirring at 40° C. Then, the reaction mixture was cooled to 20° C. and stirred for 30 minutes. The precipitated solid was obtained by filtration, washed with methyl ethyl ketone and then dried under reduced pressure at 60° C. to provide 57 mg of the title compound as a white powder (yield: 93%).

$^1$H-NMR spectrum (400 MHz, CD$_3$OD) δ: 8.34 (2H, s), 7.86-7.81 (2H, m), 7.60-7.41 (3H, m), 5.34-5.26 (1H, m), 4.71-4.63 (1H, m), 4.43-4.32 (1H, m), 4.02-3.91 (1H, m), 3.93 (2H, s), 3.56 (2H, d, J=10.9 Hz), 3.51 (2H, d, J=10.9 Hz), 3.42-3.32 (1H, m), 3.20-2.96 (3H, m), 2.55-1.67 (14H, m), 1.22 (3H, s), 1.08 (3H, s), 1.00 (3H, s), 0.97-0.84 (1H, m).

Mass spectrum (FAB+, m/z): 751 [(M+1)$^+$].
Mass spectrum (FAB−, m/z): 79, 81 [Br$^−$].

Anal. Calcd for $C_{39}H_{50}N_4O_4F_6Br_2$: Br, 17.51. Found: Br, 17.47.

Example 4

(5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol dihydrochloride Anal. Calcd for $C_{39}H_{50}N_4O_4F_6Cl_2$: Cl, 8.61. Found: Cl, 7.82.

Example 5

(5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol methanesulfonate

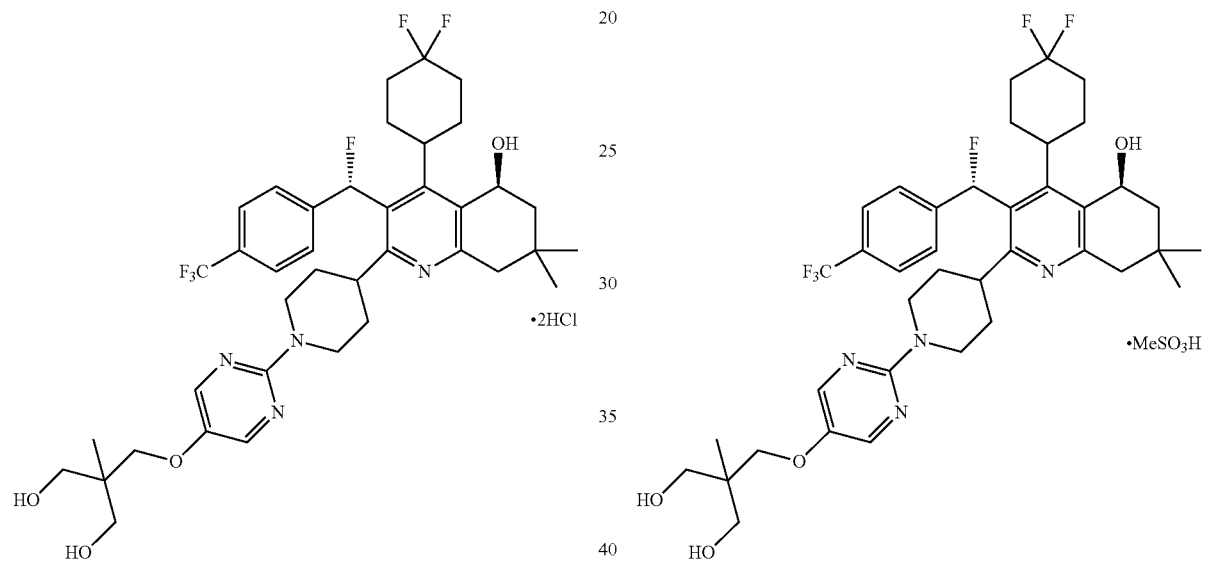

Reactions similar to those of Example 3 were performed except for using 12 µl (0.14 mmol) of 35% hydrochloric acid instead of 47% hydrobromic acid and using a mixed solution of 0.5 ml of ethyl acetate and 35 µl of ethanol instead of methyl ethyl ketone, and from 51.2 mg (0.0682 mmol) of (5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol, which was prepared by a method similar to that of Reference Example 19, 43 mg of the title compound was obtained as a white powder (yield: 77%).

$^1$H-NMR spectrum (400 MHz, $CD_3OD$) δ: 8.33 (2H, s), 7.86-7.82 (2H, m), 7.59-7.40 (3H, m), 5.34-5.25 (1H, m), 4.72-4.64 (1H, m), 4.43-4.33 (1H, m), 4.02-3.91 (1H, m), 3.92 (2H, s), 3.56 (2H, d, J=11.0 Hz), 3.51 (2H, d, J=10.9 Hz), 3.40-3.32 (1H, m), 3.18-2.94 (3H, m), 2.50-1.68 (14H, m), 1.21 (3H, s), 1.08 (3H, s), 1.00 (3H, s), 0.96-0.85 (1H, m).

Mass spectrum (FAB+, m/z): 751 [(M+1)$^+$].

Mass spectrum (FAB−, m/z): 35, 37 [Cl$^-$].

Reactions similar to those of Example 3 were performed except for using 4.5 µl (0.069 mmol) of methanesulfonic acid instead of 47% hydrobromic acid salt and using 2.5 ml of tert-butyl methyl ether instead of methyl ethyl ketone, and from 51.8 mg (0.069 mmol) of (5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol, which was prepared by a method similar to that of Reference Example 19, 29 mg of the title compound was obtained as a white powder (yield: 50%).

$^1$H-NMR spectrum (400 MHz, $CD_3OD$) δ: 8.22 (2H, s), 7.85-7.80 (2H, m), 7.57-7.39 (3H, m), 5.33-5.25 (1H, m), 4.77-4.69 (1H, m), 4.48-4.36 (1H, m), 3.99-3.89 (1H, m), 3.88 (2H, s), 3.56 (2H, d, J=11.0 Hz), 3.51 (2H, d, J=10.9 Hz), 3.28-3.22 (1H, m), 3.08-2.82 (3H, m), 2.68 (3H, s), 2.41-1.68 (14H, m), 1.21 (3H, s), 1.07 (3H, s), 0.99 (3H, s), 0.90-0.80 (1H, m).

Mass spectrum (FAB+, m/z): 751 [M$^+$].

Mass spectrum (FAB−, m/z): 95 [methanesulfonate ion].

Example 6

Example 6-1

(5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol hydrochloride

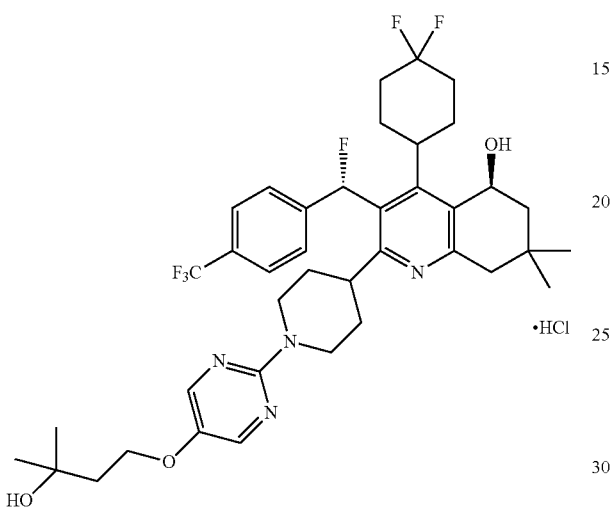

To a solution of 48.6 mg (0.066 mmol) of (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, which was prepared by a method similar to that of Reference Example 16, in 0.1 ml of acetone, 0.0058 ml (0.067 mmol) of 35% hydrochloric acid was added at room temperature. Subsequently, a small amount of a seed crystal was added thereto, and the reaction mixture was stirred for 50 minutes. The precipitated solid was obtained by filtration, washed with 0.1 ml of acetone five times and then dried under reduced pressure at 40° C. to provide 26.4 mg of the title compound as a white powder (yield: 52%).

$^1$H-NMR spectrum (400 MHz, CD$_3$OD) δ: 8.14 (2H, s), 7.84-7.79 (2H, m), 7.55-7.36 (3H, m), 5.31-5.23 (1H, m), 4.77-4.70 (1H, m), 4.47-4.38 (1H, m), 4.12 (2H, t, J=6.9 Hz), 3.97-3.84 (1H, m), 3.27-3.12 (1H, m), 3.05-2.75 (3H, m), 2.40-1.68 (14H, m), 1.93 (2H, t, J=6.8 Hz), 1.26 (6H, s), 1.20 (3H, s), 1.06 (3H, s), 0.86-0.72 (1H, m).

Mass spectrum (FAB+, m/z): 735 [(M+1)$^+$].
Mass spectrum (FAB−, m/z): 35, 37 [Cl$^-$].
Anal. Calcd for C$_{39}$H$_{49}$N$_4$O$_3$F$_6$Cl: Cl, 4.60. Found: Cl, 4.27.

Example 6-2

(5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol hydrochloride To a solution of 270 mg (0.367 mmol) of (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, which was prepared by a method similar to that of Reference Example 16, in 0.54 ml of acetone, 0.0322 ml (0.386 mmol) of 35% hydrochloric acid was added at room temperature, and the mixture was stirred. This solution was left standing overnight at −20° C. After precipitation of a solid, the reaction solution was further stirred at room temperature for 1 hour. The solid was obtained by filtration, washed with a 1:1 mixed solvent of acetone and tert-butyl methyl ether and then dried under reduced pressure at 40° C. to provide 179 mg of the title compound as a white powder (yield: 63%).

The $^1$H-NMR spectrum was substantially the same as that of the compound obtained in Example 6-1.

Water content [Karl Fischer Method; AQ-7 manufactured by Hiranuma Sangyo Corp.]:
Found: 2.8% (Measurement condition: humidity: 30-34% RH).
Reference calculation (as C$_{39}$H$_{49}$N$_4$O$_3$F$_6$Cl.H$_2$O): 2.3%.

Example 7

Example 7-1

(5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol hydrobromide

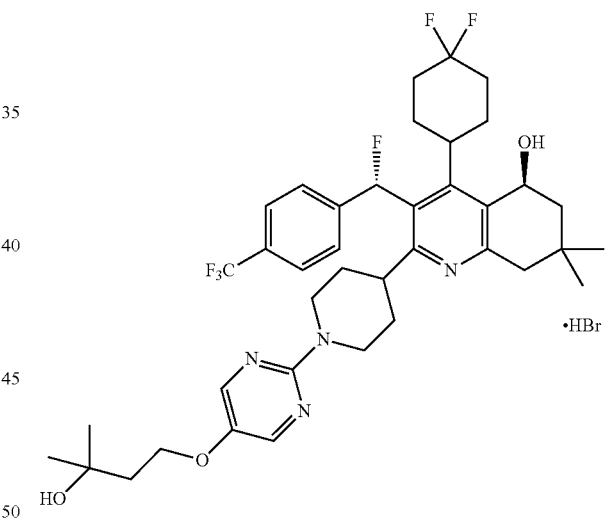

To a solution of 50.0 mg (0.068 mmol) of (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, which was prepared by a method similar to that of Reference Example 16, in 0.1 ml of acetone, 0.008 ml (0.069 mmol) of 47% hydrobromic acid was added at room temperature. Subsequently, a small amount of a seed crystal was added thereto, and the reaction mixture was stirred for 50 minutes. The precipitated solid was obtained by filtration, washed with 0.1 ml of acetone five times and then dried under reduced pressure at 40° C. to provide 38.1 mg of the title compound as a white powder (yield: 69%).

$^1$H-NMR spectrum (400 MHz, CD$_3$OD) δ: 8.15 (2H, s), 7.85-7.78 (2H, m), 7.58-7.37 (3H, m), 5.33-5.21 (1H, m), 4.78-4.70 (1H, m), 4.49-4.38 (1H, m), 4.12 (2H, t, J=6.9 Hz), 3.98-3.84 (1H, m), 3.27-3.15 (1H, m), 3.06-2.77 (3H, m), 2.42-1.67 (14H, m), 1.94 (2H, t, J=6.9 Hz), 1.26 (6H, s), 1.20 (3H, s), 1.06 (3H, s), 0.89-0.75 (1H, m).
Mass spectrum (FAB+, m/z): 735 [(M+1)$^+$].
Mass spectrum (FAB−, m/z): 79, 81 [Br$^-$].
Anal. Calcd for $C_{39}H_{49}N_4O_3F_6Br$: Br, 9.80. Found: Br, 9.43.

Example 7-2

(5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol hydrobromide Reactions similar to those of Example 6-2 were performed except for using 0.0308 ml (0.271 mmol) of 47% hydrobromic acid instead of 35% hydrochloric acid and using 0.38 ml of acetone, and from 190 mg (0.259 mmol) of (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, which was prepared by a method similar to that of Reference Example 16, 136 mg of the title compound was obtained as a white powder (yield: 64%).
The $^1$H-NMR spectrum was substantially the same as that of the compound obtained in Example 7-1.
Water content [Karl Fischer Method; MKC-510 manufactured by Kyoto Electronics Manufacturing Co., Ltd.]:
Found: 2.0% (Measurement condition: humidity: 15-18% RH).
Reference calculation (as $C_{39}H_{49}N_4O_3F_6Br \cdot H_2O$): 2.2%.

Example 8

(5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol disuccinate

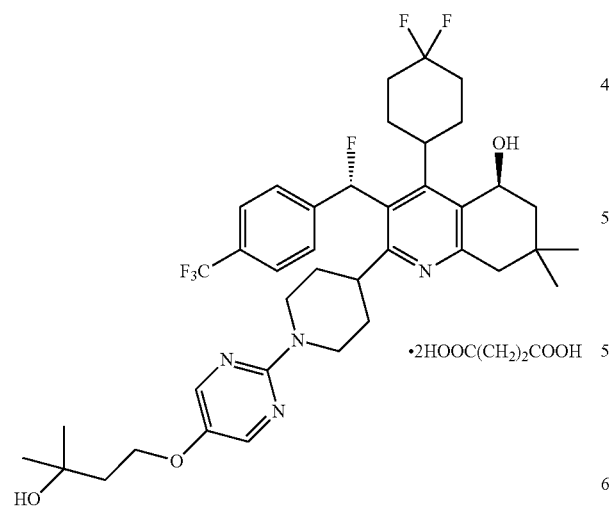

To 40.8 mg (0.056 mmol) of (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, which was prepared by a method similar to that of Reference Example 16, and 13.1 mg (0.11 mmol) of succinic acid, 0.08 ml of acetone and 0.008 ml of ultrapure water were added, and the reaction mixture was stirred at room temperature to obtain a homogeneous solution. A small amount of a seed crystal was added thereto, then 0.02 ml of acetone was added, and the reaction mixture was stirred for 30 minutes. The precipitated solid was obtained by filtration, washed with 0.4 ml of acetone and then dried under reduced pressure at 40° C. to provide 18.7 mg of the title compound as a white powder (yield: 39%).
$^1$H-NMR spectrum (400 MHz, $CD_3OD$) δ: 8.07 (2H, s), 7.77-7.70 (2H, m), 7.50-7.43 (2H, m), 7.28 (1H, d, J=47.1 Hz), 5.20-5.12 (1H, m), 4.66-4.59 (1H, m), 4.34-4.27 (1H, m), 4.10 (2H, t, J=6.9 Hz), 3.78-3.66 (1H, m), 2.93-2.53 (4H, m), 2.56 (8H, s), 2.34-1.56 (14H, m), 1.93 (2H, t, J=6.9 Hz), 1.26 (6H, s), 1.13 (3H, s), 0.97 (3H, s), 0.64-0.53 (1H, m).
Mass spectrum (FAB+, m/z): 735 [(M+1)$^+$].
Mass spectrum (FAB−, m/z): 117 [succinate ion].

Example 9

Example 9-1

(5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol benzenesulfonate

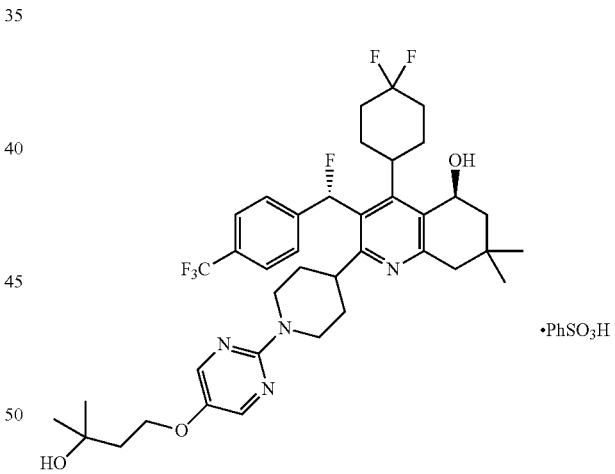

To a solution of 30.0 mg (0.0408 mmol) of (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, which was prepared by a method similar to that of Reference Example 16, in 0.4 ml of tert-butyl methyl ether, 0.013 ml (0.041 mmol) of 3.16 M benzenesulfonic acid aqueous solution was added dropwise with stirring at 40° C. Then, the reaction mixture was cooled to room temperature and stirred for 30 minutes. The precipitated solid was obtained by filtration, washed with tert-butyl methyl ether and then dried under reduced pressure at 60° C. to provide 29.8 mg of the title compound as a white powder (yield: 82%).

$^1$H-NMR spectrum (400 MHz, CD$_3$OD) δ: 8.14 (2H, s), 7.84-7.78 (4H, m), 7.56-7.38 (6H, m), 5.31-5.23 (1H, m), 4.77-4.69 (1H, m), 4.48-4.37 (1H, m), 4.12 (2H, t, J=6.9 Hz), 3.97-3.84 (1H, m), 3.25-3.16 (1H, m), 3.04-2.77 (3H, m), 2.39-1.69 (14H, m), 1.93 (2H, t, J=6.9 Hz), 1.26 (6H, s), 1.19 (3H, s), 1.05 (3H, s), 0.86-0.76 (1H, m).

Mass spectrum (FAB+, m/z): 735 [(M+1)$^+$].

Mass spectrum (FAB−, m/z): 157 [benzenesulfonate ion].

Example 9-2

(5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol benzenesulfonate Reactions similar to those of Example 9-1 were performed, and from 140 mg (0.191 mmol) of (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, which was prepared by a method similar to that of Reference Example 16, 137 mg of the title compound was obtained as a white powder (yield: 81%).

The compound obtained in Example 9-2 exhibited substantially the same $^1$H-NMR spectrum and powder X-ray diffraction pattern as those of the compound obtained in Example 9-1.

Water content of the compound obtained in Example 9-2 [Karl Fischer Method; AQ-7 manufactured by Hiranuma Sangyo Corp.]:

Found: 2.2% (Measurement condition: humidity: 30-34% RH).

Calcd (C$_{45}$H$_{54}$N$_4$O$_6$SF$_6$·H$_2$O): 2.0%.

Compound obtained in Example 9-1: Anal. Calcd for C$_{45}$H$_{54}$N$_4$O$_6$SF$_6$·H$_2$O:

C, 59.32; H, 6.20; N, 6.15.

Found: C, 59.02; H, 6.21; N, 5.94.

From each analytical data described above, the salts of the compounds obtained in Examples 9-1 and 9-2 were both shown to be monohydrates in the same crystal form, i.e., (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl] piperidin-4-yl}-7,7-dimethyl-5,6,7,8-tetrahydroquinolin-5-ol benzenesulfonate monohydrate.

Example 10

(5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol maleate

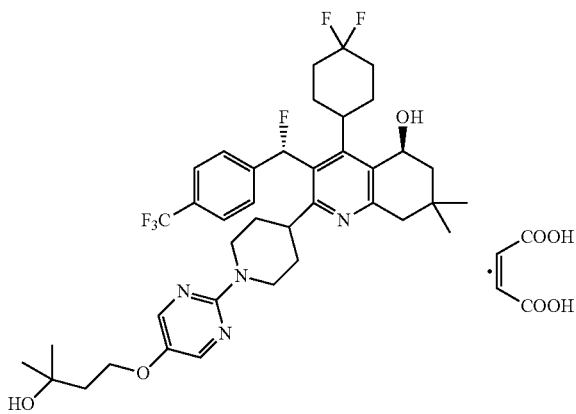

To a solution of 6.4 mg (0.055 mmol) of maleic acid in 0.2 ml of ethyl acetate, a solution of 40.7 mg (0.055 mmol) of (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, which was prepared by a method similar to that of Reference Example 16, in 0.2 ml of ethyl acetate was added with stirring at 60° C. Then, the reaction mixture was cooled to 10° C. and stirred for 30 minutes. The precipitated solid was obtained by filtration, washed with 0.04 ml of ethyl acetate three times and then dried under reduced pressure at 40° C. to provide 35.3 mg of the title compound as a white powder (yield: 75%).

$^1$H-NMR spectrum (400 MHz, CD$_3$OD) δ: 8.08 (2H, s), 7.78-7.72 (2H, m), 7.51-7.45 (2H, m), 7.33 (1H, d, J=47.1 Hz), 6.29 (2H, s), 5.22-5.15 (1H, m), 4.70-4.61 (1H, m), 4.39-4.29 (1H, m), 4.10 (2H, t, J=6.9 Hz), 3.82-3.70 (1H, m), 3.01-2.61 (4H, m), 2.36-1.59 (14H, m), 1.93 (2H, t, J=6.9 Hz), 1.26 (6H, s), 1.15 (3H, s), 1.00 (3H, s), 0.70-0.59 (1H, m).

Mass spectrum (FAB+, m/z): 735 [(M+1)$^+$].

Mass spectrum (FAB−, m/z): 115 [maleate ion].

Example 11

(5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol hemifumarate

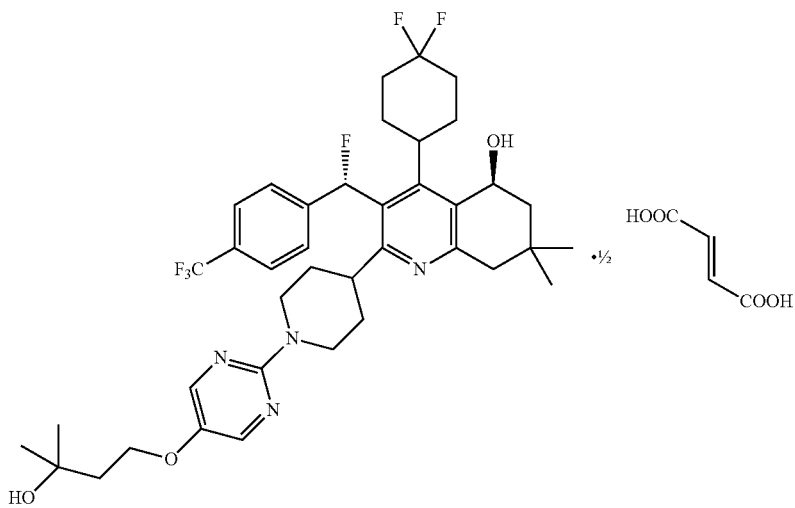

To 40.0 mg (0.054 mmol) of (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, which was prepared by a method similar to that of Reference Example 16, and 3.3 mg (0.028 mmol) of fumaric acid, 0.08 ml of acetone and 0.008 ml of ultrapure water were added, and the reaction mixture was stirred at room temperature to obtain a homogeneous solution. Subsequently, a small amount of a seed crystal was added thereto, and then the reaction mixture was stirred for 30 minutes under ice cooling. The precipitated solid was obtained by filtration, washed with 0.04 ml of acetone and then dried under reduced pressure at 40° C. to provide 35.6 mg of the title compound as a white powder (yield: 77%).

$^1$H-NMR spectrum (400 MHz, $CD_3OD$) δ: 8.07 (2H, s), 7.77-7.71 (2H, m), 7.50-7.43 (2H, m), 7.28 (1H, d, J=47.3 Hz), 6.75 (1H, s), 5.21-5.10 (1H, m), 4.68-4.57 (1H, m), 4.37-4.26 (1H, m), 4.10 (2H, t, J=6.9 Hz), 3.79-3.66 (1H, m), 2.94-2.55 (4H, m), 2.33-1.56 (14H, m), 1.93 (2H, t, J=6.9 Hz), 1.26 (6H, s), 1.13 (3H, s), 0.97 (3H, s), 0.65-0.54 (1H, m).

Mass spectrum (FAB+, m/z): 735 [(M+1)$^+$].
Mass spectrum (FAB−, m/z): 115 [fumarate ion].

Example 12

(5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol methanesulfonate

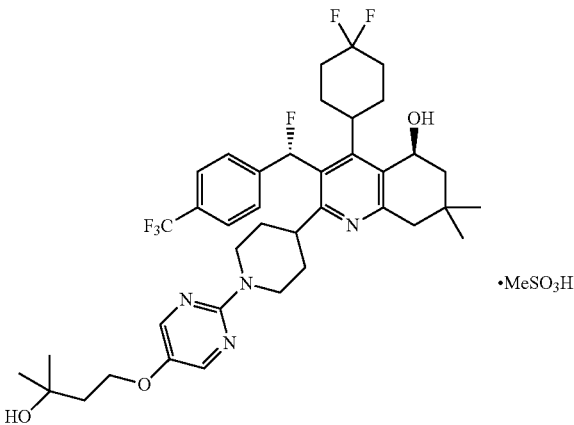 [SMILES: "·MeSO3H" ; CC(C)(O)CCOc1cnc(N2CCC(c3nc4c(c(C5CCC(F)(F)CC5)c3[C@@H](F)c3ccc(C(F)(F)F)cc3)[C@@H](O)CC(C)(C)C4)CC2)nc1]

To 40.7 mg (0.055 mmol) of (5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol, which was prepared by a method similar to that of Reference Example 16, 0.28 ml of isopropyl acetate and 0.008 ml of ultrapure water were added, and the reaction mixture was stirred at room temperature to obtain a homogeneous solution. Then, 0.004 ml (0.062 mmol) of methanesulfonic acid was added thereto, and the reaction mixture was stirred at the same temperature for 90 minutes. The precipitated solid was obtained by filtration, washed with 0.04 ml of isopropyl acetate three times and then dried under reduced pressure at 40° C. to provide 38.7 mg of the title compound as a white powder (yield: 85%).

$^1$H-NMR spectrum (400 MHz, CD$_3$OD) δ: 8.15 (2H, s), 7.85-7.79 (2H, m), 7.57-7.37 (3H, m), 5.31-5.23 (1H, m), 4.77-4.70 (1H, m), 4.48-4.38 (1H, m), 4.12 (2H, t, J=6.9 Hz), 3.97-3.84 (1H, m), 3.27-3.15 (1H, m), 3.05-2.76 (3H, m), 2.68 (3H, s), 2.40-1.68 (14H, m), 1.94 (2H, t, J=6.9 Hz), 1.26 (6H, s), 1.20 (3H, s), 1.06 (3H, s), 0.87-0.75 (1H, m).

Mass spectrum (FAB+, m/z): 735 [(M+1)$^+$].

Mass spectrum (FAB−, m/z): 95 [methanesulfonate ion].

Example 13

(5S)-4-(4,4-Difluorocyclohexyl)-2-[1-(5-{[(2S)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol dihydrochloride

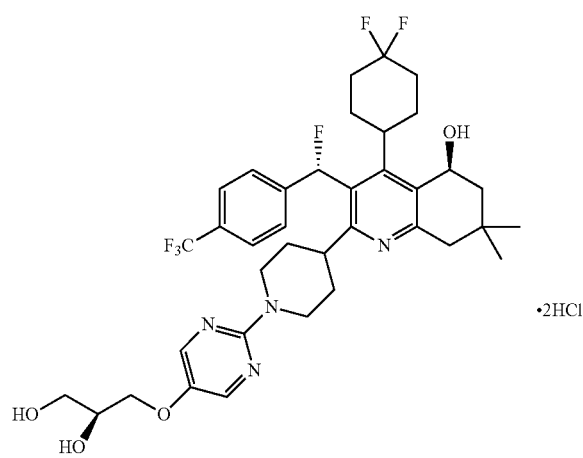 [SMILES: CC1(C)Cc2nc(C3CCN(c4ncc(OC[C@@H](O)CO)cn4)CC3)c([C@@H](F)c3ccc(C(F)(F)F)cc3)c(C3CCC(F)(F)CC3)c2[C@@H](O)C1 ; "·2HCl"]

To a solution of 36.2 mg (50.1 μmol) of (5S)-4-(4,4-Difluorocyclohexyl)-2-[1-(5-{[(2S)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol, which was prepared by a method similar to that of Reference Example 25, in 0.36 ml of acetone, 9.2 μl (110 μmol) of 35% hydrochloric acid was added dropwise with stirring at 45° C., and the mixture was stirred for 10 minutes. Then, stirring was continued at room temperature for 30 minutes, and the precipitated solid was obtained by filtration, washed with acetone and then dried under reduced pressure at 40° C. to provide 26.3 mg of the title compound as a white powder (yield: 66%).

$^1$H-NMR spectrum (400 MHz, CD$_3$OD) δ: 8.29 (2H, s), 7.86-7.80 (2H, m), 7.61-7.37 (3H, m), 5.32-5.25 (1H, m), 4.75-4.67 (1H, m), 4.46-4.37 (1H, m), 4.12 (1H, dd, J=10, 4 Hz), 4.02 (1H, dd, J=10, 6 Hz), 3.97-3.91 (2H, m), 3.63 (2H, d, J=6 Hz), 3.36-3.32 (1H, m), 3.12-2.88 (3H, m), 2.43-1.68 (14H, m), 1.21 (3H, s), 1.08 (3H, s), 0.95-0.82 (1H, m).

Mass spectrum (FAB+, m/z): 723 [(M+1)$^+$].

Anal. Calcd for C$_{37}$H$_{46}$N$_4$O$_4$F$_6$Cl$_2$: Cl, 8.91. Found: Cl, 8.67.

Example 14

(5S)-4-(4,4-Difluorocyclohexyl)-2-[1-(5-{[(2S)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol dihydrobromide

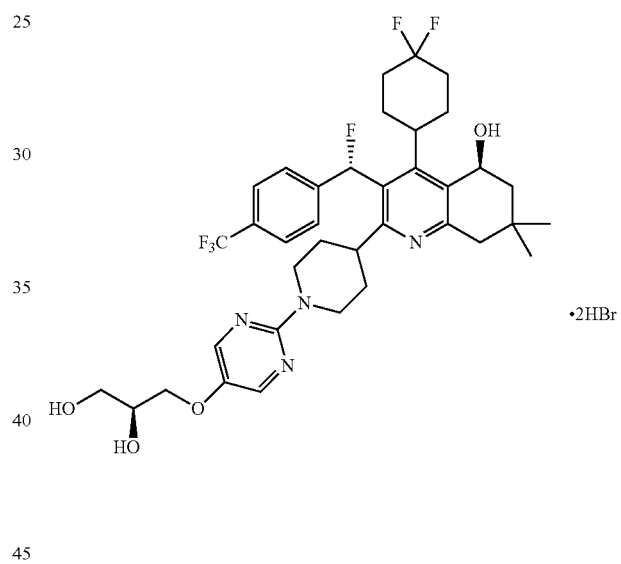

Reactions similar to those of Example 13 were performed except for using 13.0 μl (114 μmol) of 47% hydrobromic acid instead of 35% hydrochloric acid and using 0.37 ml of a 1:1 mixed solvent of acetone and tert-butyl methyl ether instead of acetone, and from 37.0 mg (51.2 μmol) of (5S)-4-(4,4-Difluorocyclohexyl)-2-[1-(5-{[(2S)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol, which was prepared by a method similar to that of Reference Example 25, 34.1 mg of the title compound was obtained as a white powder (yield: 75%).

$^1$H-NMR spectrum (400 MHz, CD$_3$OD) δ: 8.29 (2H, s), 7.87-7.79 (2H, m), 7.61-7.39 (3H, m), 5.35-5.24 (1H, m), 4.77-4.66 (1H, m), 4.48-4.35 (1H, m), 4.12 (1H, dd, J=10, 4 Hz), 4.02 (1H, dd, J=10, 6 Hz), 3.98-3.91 (2H, m), 3.63 (2H, d, J=6 Hz), 3.37-3.32 (1H, m), 3.14-2.88 (3H, m), 2.42-1.69 (14H, m), 1.21 (3H, s), 1.08 (3H, s), 0.95-0.83 (1H, m).

Mass spectrum (FAB+, m/z): 723 [(M+1)$^+$].

Anal. Calcd for C$_{37}$H$_{46}$N$_4$O$_4$F$_6$Br$_2$: Br, 18.07. Found: Br, 17.95.

Example 15

(5S)-4-(4,4-Difluorocyclohexyl)-2-[1-(5-{[(2R)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol dihydrochloride

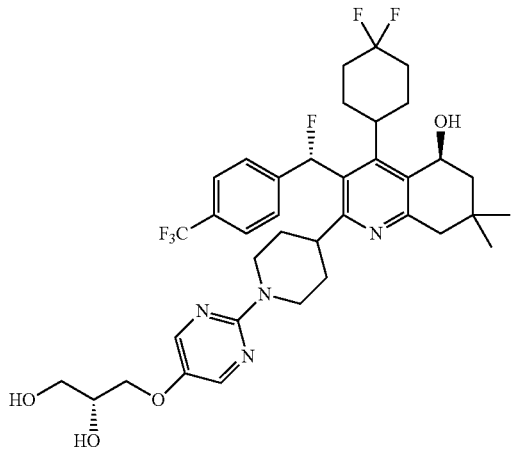

Reactions similar to those of Example 13 were performed except for using 10.8 μl (130 μmol) of 35% hydrochloric acid and using a mixed solvent of 0.43 ml of acetone and 0.43 ml of tert-butyl methyl ether instead of acetone, and from 43.3 mg (59.9 μmol) of (5S)-4-(4,4-Difluorocyclohexyl)-2-[1-(5-{[(2R)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol, which was prepared by a method similar to that of Reference Example 27, 24.0 mg of the title compound was obtained as a white powder (yield: 50%).

$^1$H-NMR spectrum (400 MHz, CD$_3$OD) δ: 8.30 (2H, s), 7.86-7.81 (2H, m), 7.60-7.39 (3H, m), 5.34-5.25 (1H, m), 4.75-4.66 (1H, m), 4.46-4.35 (1H, m), 4.12 (1H, dd, J=10, 4 Hz), 4.02 (1H, dd, J=10, 6 Hz), 3.98-3.91 (2H, m), 3.64 (2H, d, J=6 Hz), 3.33-3.31 (1H, m), 3.15-2.89 (3H, m), 2.43-1.69 (14H, m), 1.21 (3H, s), 1.08 (3H, s), 0.95-0.83 (1H, m).

Mass spectrum (FAB+, m/z): 723 [(M+1)$^+$].

Anal. Calcd for C$_{37}$H$_{46}$N$_4$O$_4$F$_6$Cl$_2$: Cl, 8.91. Found: Cl, 8.48.

Example 16

(5S)-4-(4,4-Difluorocyclohexyl)-2-[1-(5-{[(2R)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol dihydrobromide

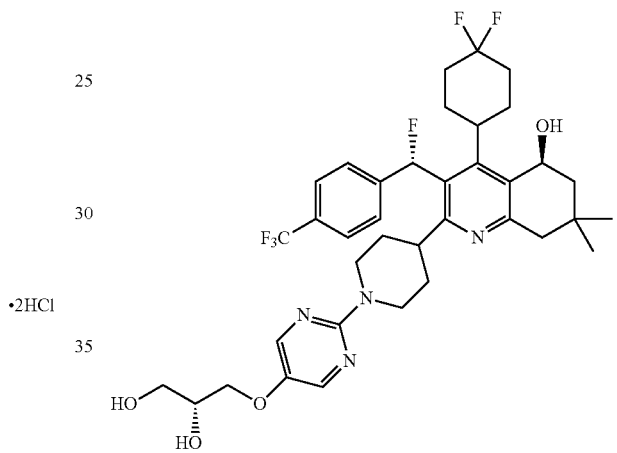

Reactions similar to those of Example 13 were performed except for using 17.3 μl (152 μmol) of 47% hydrobromic acid instead of 35% hydrochloric acid and using 0.50 ml of a 1:1 mixed solvent of acetone and tert-butyl methyl ether instead of acetone, and from 49.5 mg (68.5 μmol) of (5S)-4-(4,4-Difluorocyclohexyl)-2-[1-(5-{[(2R)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol, which was prepared by a method similar to that of Reference Example 27, 36.6 mg of the title compound was obtained as a white powder (yield: 60%).

$^1$H-NMR spectrum (400 MHz, CD$_3$OD) δ: 8.30 (2H, s), 7.87-7.79 (2H, m), 7.62-7.40 (3H, m), 5.34-5.22 (1H, m), 4.76-4.65 (1H, m), 4.48-4.35 (1H, m), 4.12 (1H, dd, J=10, 4 Hz), 4.02 (1H, dd, J=10, 6 Hz), 3.98-3.91 (2H, m), 3.64 (2H, d, J=6 Hz), 3.37-3.31 (1H, m), 3.15-2.88 (3H, m), 2.44-1.68 (14H, m), 1.21 (3H, s), 1.08 (3H, s), 0.95-0.84 (1H, m).

Mass spectrum (FAB+, m/z): 723 [(M+1)$^+$].

Anal. Calcd for $C_{37}H_{46}N_4O_4F_6Br_2$: Br, 18.07. Found: Br, 17.92.

Anal. Calcd for $C_{38}H_{48}N_4O_4F_6SCl_2$: Cl, 8.42. Found: Cl, 8.30.

Example 17

(5S)-4-(4,4-Difluorocyclohexyl)-3-{(S)-fluoro[4-(trifluoromethyl)phenyl]methyl}-7,7-dimethyl-2-(1-{5-[3-(methylsulfonyl)propoxy]pyrimidin-2-yl}piperidin-4-yl)-5,6,7,8-tetrahydroquinolin-5-ol dihydrochloride

Example 18

(5S)-4-(4,4-Difluorocyclohexyl)-3-{(S)-fluoro[4-(trifluoromethyl)phenyl]methyl}-7,7-dimethyl-2-(1-{5-[3-(methylsulfonyl)propoxy]pyrimidin-2-yl}piperidin-4-yl)-5,6,7,8-tetrahydroquinolin-5-ol dihydrobromide

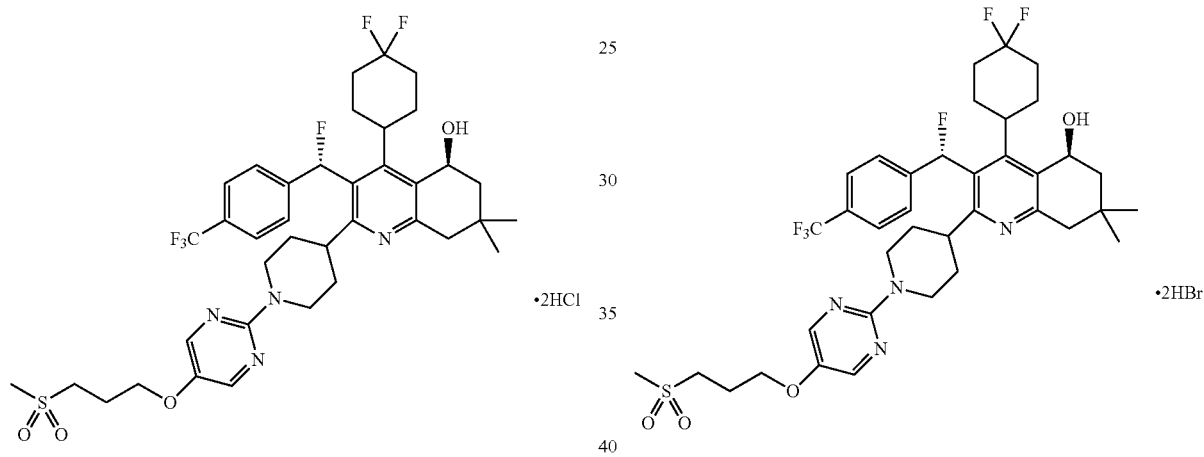

Reactions similar to those of Example 13 were performed except for using 9.6 μl (115 μmol) of 35% hydrochloric acid and using 0.40 ml of acetone, and from 40.1 mg (52.2 μmol) of (5S)-4-(4,4-Difluorocyclohexyl)-3-{(S)-fluoro[4-(trifluoromethyl)phenyl]methyl}-7,7-dimethyl-2-(1-{5-[3-(methylsulfonyl)propoxy]pyrimidin-2-yl}piperidin-4-yl)-5,6,7,8-tetrahydroquinolin-5-ol, which was prepared by a method similar to that of Reference Example 28, 28.6 mg of the title compound was obtained as a white powder (yield: 65%).

$^1$H-NMR spectrum (400 MHz, $CD_3OD$) δ: 8.26 (2H, s), 7.86-7.80 (2H, m), 7.59-7.40 (3H, m), 5.34-5.25 (1H, m), 4.77-4.68 (1H, m), 4.48-4.38 (1H, m), 4.17 (2H, t, J=6 Hz), 4.01-3.88 (1H, m), 3.36-3.30 (3H, m), 3.12-2.88 (3H, m), 3.01 (3H, s), 2.40-1.68 (16H, m), 1.21 (3H, s), 1.08 (3H, s), 0.93-0.81 (1H, m).

Mass spectrum (FAB+, m/z): 769 [(M+1)$^+$].

Reactions similar to those of Example 13 were performed except for using 13.2 μl (116 μmol) of 47% hydrobromic acid instead of 35% hydrochloric acid and using 0.40 ml of acetone, and from 40.0 mg (52.0 μmol) of (5S)-4-(4,4-Difluorocyclohexyl)-3-{(S)-fluoro[4-(trifluoromethyl)phenyl]methyl}-7,7-dimethyl-2-(1-{5-[3-(methylsulfonyl)propoxy]pyrimidin-2-yl}piperidin-4-yl)-5,6,7,8-tetrahydroquinolin-5-ol, which was prepared by a method similar to that of Reference Example 28, 27.2 mg of the title compound was obtained as a white powder (yield: 56%).

$^1$H-NMR spectrum (400 MHz, $CD_3OD$) δ: 8.27 (2H, s), 7.86-7.81 (2H, m), 7.59-7.40 (3H, m), 5.33-5.26 (1H, m), 4.76-4.68 (1H, m), 4.46-4.38 (1H, m), 4.17 (2H, t, J=6 Hz), 4.01-3.89 (1H, m), 3.37-3.31 (3H, m), 3.14-2.89 (3H, m), 3.01 (3H, s), 2.41-1.62 (16H, m), 1.21 (3H, s), 1.08 (3H, s), 0.93-0.84 (1H, m).

Mass spectrum (FAB+, m/z): 769 [(M+1)$^+$].

Anal. Calcd for $C_{38}H_{48}N_4O_4F_6SBr_2$: Br, 17.17. Found: Br, 17.45.

Example 19

(5S)-4-(4,4-Difluorocyclohexyl)-3-{(S)-fluoro[4-(trifluoromethyl)phenyl]methyl}-7,7-dimethyl-2-(1-{5-[3-(methylsulfonyl)propoxy]pyrimidin-2-yl}piperidin-4-yl)-5,6,7,8-tetrahydroquinolin-5-ol methanesulfonate

Example 20

(5S)-2-{1-[5-(3-Carboxyphenyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol dihydrochloride

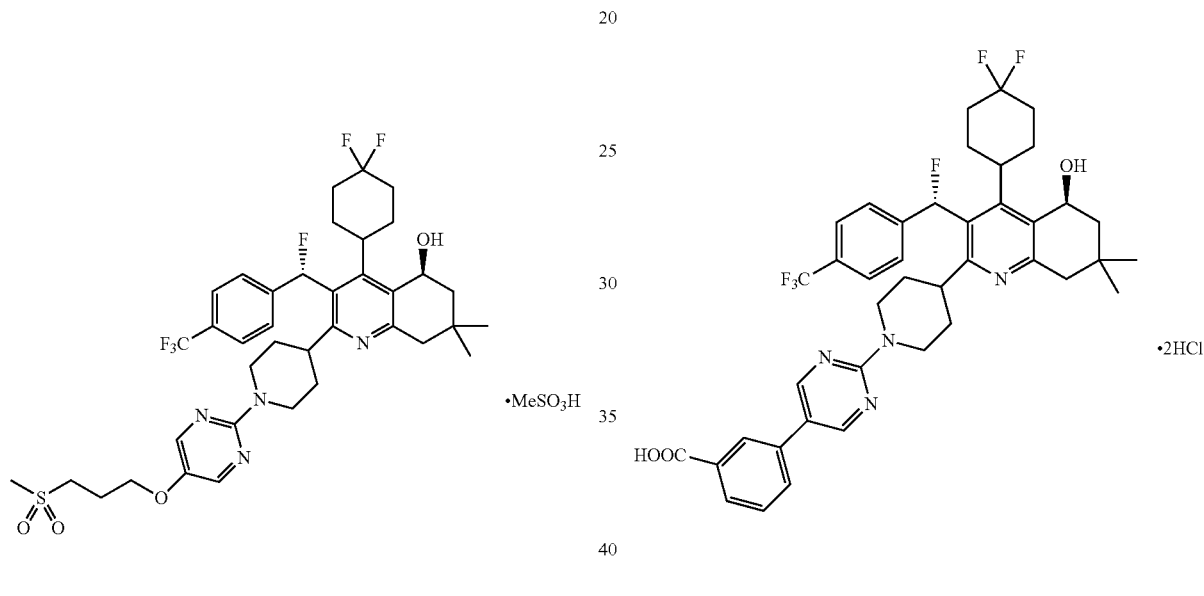

Reactions similar to those of Example 13 were performed except for using 3.8 μl (57 μmol) of methanesulfonic acid instead of 35% hydrochloric acid and using 1.5 ml of isopropyl acetate instead of acetone, and from 40.0 mg (52.0 μmol) of (5S)-4-(4,4-Difluorocyclohexyl)-3-{(S)-fluoro[4-(trifluoromethyl)phenyl]methyl}-7,7-dimethyl-2-(1-{5-[3-(methylsulfonyl)propoxy]pyrimidin-2-yl}piperidin-4-yl)-5,6,7,8-tetrahydroquinolin-5-ol, which was prepared by a method similar to that of Reference Example 28, 35.3 mg of the title compound was obtained as a white powder (yield: 78%).

$^1$H-NMR spectrum (400 MHz, $CD_3OD$) δ: 8.20-8.11 (2H, m), 7.86-7.77 (2H, m), 7.59-7.36 (3H, m), 5.31-5.23 (1H, m), 4.81-4.71 (1H, m), 4.52-4.40 (1H, m), 4.12 (2H, t, J=6 Hz), 3.98-3.85 (1H, m), 3.38-3.31 (2H, m), 3.25-3.14 (1H, m), 3.05-2.93 (1H, m), 3.00 (3H, s), 2.89-2.75 (2H, m), 2.69 (3H, s), 2.41-1.67 (16H, m), 1.20 (3H, s), 1.06 (3H, s), 0.85-0.73 (1H, m).

Mass spectrum (FAB+, m/z): 769 [(M+1)$^+$].

Reactions similar to those of Example 13 were performed except for using 7.4 μl (89 μmol) of 35% hydrochloric acid and using 0.30 ml of acetone, and from 30.5 mg (40.5 μmol) of (5S)-2-{1-[5-(3-Carboxyphenyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol, which was prepared by a method similar to that of Reference Example 30, 28.0 mg of the title compound was obtained as a white powder (yield: 84%).

$^1$H-NMR spectrum (400 MHz, $CD_3OD$) δ: 8.75 (2H, s), 8.25-8.22 (1H, m), 8.06-8.03 (1H, m), 7.88-7.82 (3H, m), 7.63-7.42 (4H, m), 5.33-5.26 (1H, m), 4.96-4.87 (1H, m), 4.68-4.57 (1H, m), 4.02-3.90 (1H, m), 3.41-3.32 (1H, m), 3.12-2.86 (3H, m), 2.46-1.70 (14H, m), 1.21 (3H, s), 1.08 (3H, s), 0.97-0.87 (1H, m).

Mass spectrum (FAB+, m/z): 753 [(M+1)$^+$].

Anal. Calcd for $C_{41}H_{44}N_4O_3F_6Cl_2$: Cl, 8.59. Found: Cl, 8.14.

Example 21

(5S)-2-{1-[5-(3-Carboxyphenyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol dihydrobromide

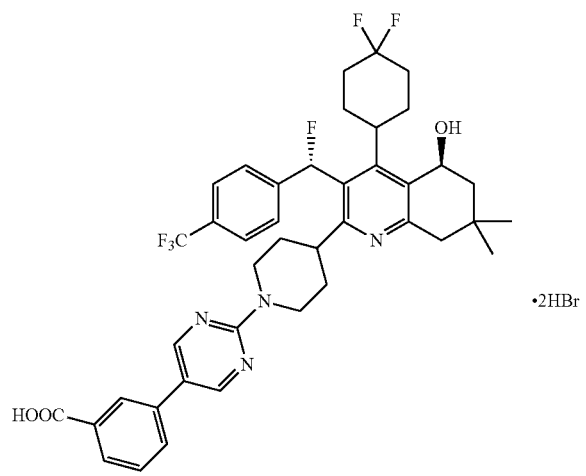 [SMILES: CC1(C)Cc2nc(C3CCN(c4ncc(-c5cccc(C(=O)O)c5)cn4)CC3)c([C@@H](F)c3ccc(C(F)(F)F)cc3)c(C3CCC(F)(F)CC3)c2[C@@H](O)C1 ; "·2HBr"]

Reactions similar to those of Example 13 were performed except for using 15.2 μl (134 μmol) of 47% hydrobromic acid instead of 35% hydrochloric acid and using 0.45 ml of acetone, and from 45.7 mg (60.7 μmol) of (5S)-2-{1-[5-(3-Carboxyphenyl)pyrimidin-2-yl]piperidin-4-yl}-4-(4,4-difluorocyclohexyl)-3-{(S)-fluoro[4-(trifluoromethyl)phenyl] methyl}-7,7-dimethyl-5,6,7,8-tetrahydroquinolin-5-ol, which was prepared by a method similar to that of Reference Example 30, 27.2 mg of the title compound was obtained as a white powder (yield: 49%).

$^1$H-NMR spectrum (400 MHz, $CD_3OD$) δ: 8.76 (2H, s), 8.25-8.22 (1H, m), 8.07-8.03 (1H, m), 7.88-7.82 (3H, m), 7.63-7.41 (4H, m), 5.35-5.27 (1H, m), 4.96-4.88 (1H, m), 4.67-4.55 (1H, m), 4.04-3.89 (1H, m), 3.44-3.35 (1H, m), 3.15-2.88 (3H, m), 2.47-1.68 (14H, m), 1.21 (3H, s), 1.08 (3H, s), 0.97-0.87 (1H, m).

Mass spectrum (FAB+, m/z): 753 [(M+1)$^+$].

Anal. Calcd for $C_{41}H_{44}N_4O_3F_6Br_2$: Br, 17.47. Found: Br, 17.43.

Reference Example 1

4,4-Difluorocyclohexanecarboaldehyde

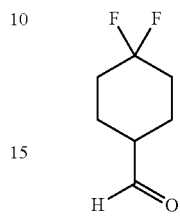

To a solution of 173 g (0.900 mol) of 4,4-difluorocyclohexanecarboxylic acid ethyl ester in 1.0 L toluene, 945 ml (0.945 mol) of 1.0 M diisobutyl aluminum hydride-toluene solution was added dropwise at −55° C. or lower temperatures and then the reaction solution was stirred at −65° C. for 30 minutes. After completion of the reaction, saturated ammonium chloride aqueous solution was added at −40° C. or lower temperatures to the reaction solution and then 1.0 L of 4 N hydrochloric acid was added at 0° C. or lower temperatures. The organic layer was separated and then the aqueous layer was extracted with toluene, and the combined organic layers were washed with 1 N hydrochloric acid, saturated sodium hydrogencarbonate aqueous solution and saturated sodium chloride aqueous solution in order and dried with anhydrous magnesium sulfate. The solvent was distilled off under reduced pressure and the obtained oily residue was subjected to distillation under reduced pressure (55-57° C./6 mmHg) to provide 75.3 g of the title compound as a colorless oil (yield: 57%).

$^1$H-NMR spectrum (300 MHz, $CDCl_3$) δ ppm: 9.68 (1H, d, J=1 Hz), 2.42-2.28 (1H, m), 2.16-1.70 (8H, m).

Reference Example 2

4-(1-Amino-2-cyanoethenyl)piperidin-1-carboxylic acid tert-butyl ester

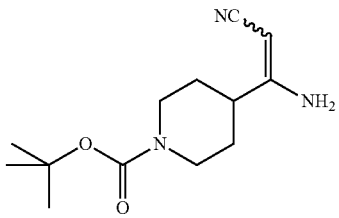 [SMILES: CC(C)(C)OC(=O)N1CCC(C(N)=CC#N)CC1]

47.7 ml (85.9 mmol) of 1.8 M lithium diisopropylamide-n-heptane/tetrahydrofuran/ethylbenzene solution was added to 50 ml of tetrahydrofuran and 4.14 ml (79.3 mmol) of acetonitrile was added dropwise under cooling with a dry ice-acetone bath, and the reaction solution was stirred for 3.0 hours. Under the same conditions, a solution of 13.9 g (66.1 mmol) of 4-cyanopiperidine-1-carboxylic acid tert-butyl ester in 30 ml of tetrahydrofuran was further added dropwise and then the reaction solution was stirred for 24 hours while the temperature of the reaction solution was slowly raised to room temperature. After completion of the reaction, ice water was added to the reaction solution and the reaction solution was extracted with ethyl acetate. The organic layer was washed with saturated sodium chloride aqueous solution and then dried with anhydrous magnesium sulfate. The solvent was distilled off under reduced pressure and the obtained residue was subjected to silica gel column chromatography [n-hexane/ethyl acetate=90/10-50/50 (V/V)], and the fraction including the desired compound was concentrated under reduced pressure to provide 10.7 g of the title compound as a yellow oil (yield: 64%).

$^1$H-NMR spectrum (300 MHz, CDCl$_3$) δ ppm: 4.65 (2H, br s), 4.34-4.15 (2H, m), 3.87 (1H, s), 2.77-2.59 (2H, m), 2.16 (1H, tt, J=12, 4 Hz), 1.84-1.73 (2H, m), 1.53-1.40 (2H, m), 1.46 (9H, s).

Mass spectrum (EI, m/z): 251 [M$^+$].

Reference Example 3

2-[(1-tert-Butyloxycarbonyl)piperidin-4-yl]-3-cyano-4-(4,4-difluorocyclohexyl)-7,7-dimethyl-5-oxo-1,4,5,6,7,8-hexahydroquinoline

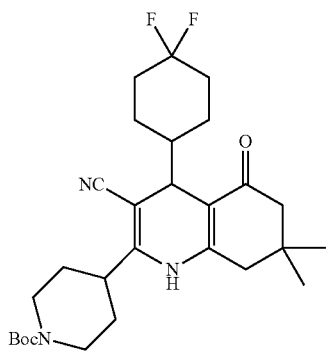 [SMILES: CC1(C)CC(=O)C2=C(C1)NC(C1CCN(C(=O)OC(C)(C)C)CC1)=C(C#N)C2C1CCC(F)(F)CC1]

To a solution of 14.6 g (57.9 mmol) of 4,4-difluorocyclohexanecarboaldehyde, which was prepared by a method similar to that of Reference Example 1, in 174 ml of toluene, 12.8 g (69.7 mmol) of 4-(1-amino-2-cyanovinyl)-piperidin-1-carboxylic acid tert-butyl ester, which was prepared by a method similar to that of Reference Example 2, was added. After stirring with heating at 100° C. for 10 minutes, 9.74 g (69.5 mmol) of dimedone was added thereto and the reaction solution was stirred under heating-to-reflux conditions for 5 hours. Furthermore, 2.43 g (17.3 mmol) of dimedone was added thereto and the reaction solution was stirred under heating-to-reflux conditions for 10 hours. After completion of the reaction, the precipitate was obtained by filtration to provide 17.9 g of the title compound as a white solid (yield: 60%).

$^1$H-NMR spectrum (300 MHz, CDCl$_3$) δ ppm: 6.27 (1H, s), 4.36-4.13 (2H, m), 3.70 (1H, d, J=2 Hz), 3.03 (1H, tt, J=12, 3 Hz), 2.91-2.73 (2H, m), 2.40-2.19 (5H, m), 2.17-1.98 (2H, m), 1.84-1.40 (9H, m), 1.48 (9H, s), 1.35-1.20 (1H, m), 1.10 (3H, s), 1.09 (3H, s).

Mass spectrum (CI, m/z): 504 [(M+1)$^+$].

Reference Example 4

2-[(1-tert-Butyloxycarbonyl)piperidin-4-yl]-3-cyano-4-(4,4-difluorocyclohexyl)-7,7-dimethyl-5-oxo-5,6,7,8-tetrahydroquinoline

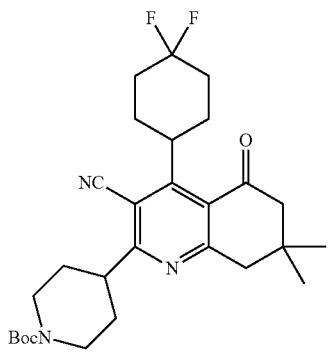 [SMILES: CC1(C)CC(=O)c2c(nc(C3CCN(C(=O)OC(C)(C)C)CC3)c(C#N)c2C2CCC(F)(F)CC2)C1]

To a solution of 26.9 g (53.4 mmol) of 2-[(1-tert-Butyloxycarbonyl)piperidin-4-yl]-3-cyano-4-(4,4-difluorocyclohexyl)-7,7-dimethyl-5-oxo-1,4,5,6,7,8-hexahydroquinoline, which was prepared by a method similar to that of Reference Example 3 in 150 ml of dichloromethane, 18.2 g (80.0 mmol) of 2,3-dichloro-5,6-dicyano-p-benzoquinone was added, and the reaction solution was stirred at room temperature for 4 hours. After completion of the reaction, the reaction solution was filtered through Celite (trade name) and the filtrate was washed with saturated sodium hydrogencarbonate aqueous solution. The obtained organic layer was washed with saturated sodium hydrogencarbonate aqueous solution and saturated sodium chloride aqueous solution in order and dried with anhydrous magnesium sulfate, and then the solvent was distilled off under reduced pressure. Methanol was added to the obtained residue and the precipitate was obtained by filtration to provide 20.7 g of the title compound as a white solid (yield: 87%).

$^1$H-NMR spectrum (300 MHz, CDCl$_3$) δ ppm: 4.38-4.15 (2H, m), 4.13-3.97 (1H, m), 3.38 (1H, tt, J=11, 4 Hz), 3.06 (2H, s), 2.97-2.80 (2H, m), 2.69-2.52 (2H, m), 2.61 (2H, s), 2.33-2.17 (2H, m), 2.01-1.72 (8H, m), 1.48 (9H, s), 1.11 (6H, s).

Mass spectrum (EI, m/z): 501 [M$^+$].

Reference Example 5

2-[(1-tert-Butyloxycarbonyl)piperidin-4-yl]-4-(4,4-difluorocyclohexyl)-3-formyl-7,7-dimethyl-5,6,7,8-tetrahydroquinolin-5-ol

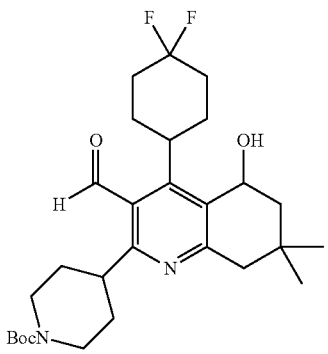 [SMILES: CC1(C)Cc2nc(C3CCN(C(=O)OC(C)(C)C)CC3)c(C=O)c(C3CCC(F)(F)CC3)c2C(O)C1]

To a solution of 20.1 g (40.0 mmol) of 2-[(1-tert-Butyloxycarbonyl)piperidin-4-yl]-3-cyano-4-(4,4-difluorocyclohexyl)-7,7-dimethyl-5-oxo-5,6,7,8-tetrahydroquinoline, which was prepared by a method similar to that of Reference Example 4, in 300 ml of toluene, 100 ml (100 mmol) of 1.0 M diisobutyl aluminum hydride-toluene solution was added dropwise at −50° C., and the reaction solution was stirred at the same temperature for 2 hours. Furthermore, 100 ml (100 mmol) of 1.0 M diisobutyl aluminum hydride-toluene solution was added dropwise at the same temperature, and the temperature of the reaction solution was raised to −21° C. and the reaction solution was stirred for 2 hours. After completion of the reaction, the reaction solution was poured into a mixed solution of 6 N hydrochloric acid, ice and ethyl acetate and the mixture was stirred vigorously. After separation, the obtained organic layer was filtered to remove the gelled substance therefrom and washed with saturated sodium hydrogencarbonate aqueous solution and saturated sodium chloride aqueous solution in order and dried with anhydrous magnesium sulfate, and then the solvent was distilled off under reduced pressure. Methanol was added to the obtained residue and the precipitate was obtained by filtration to provide 10.6 g of the title compound as a white solid (yield: 52%).

$^1$H-NMR spectrum (300 MHz, CDCl$_3$) δ ppm: 10.81 (1H, s), 5.09 (1H, q, J=6 Hz), 4.32-4.09 (2H, m), 3.53-3.37 (1H, m), 3.11 (1H, tt, J=11, 4 Hz), 2.97-2.56 (2H, m), 2.88 (1H, d, J=17 Hz), 2.65 (1H, d, J=17 Hz), 2.31-1.50 (15H, m), 1.47 (9H, s), 1.15 (3H, s), 1.00 (3H, s).

Mass spectrum (CI, m/z): 507 [(M+1)$^+$].

Reference Example 6

2-[(1-tert-Butyloxycarbonyl)piperidin-4-yl]-4-(4,4-difluorocyclohexyl)-3-formyl-5-[(4-methoxybenzyl)oxy]-7,7-dimethyl-5,6,7,8-tetrahydroquinoline

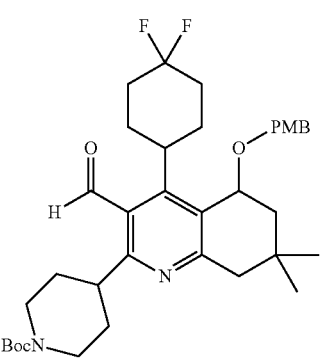

To a solution of 0.846 g (19.4 mmol) of sodium hydride (55% dispersion in mineral oil) in 19 ml of N,N-dimethylformamide, a solution of 9.63 g (19.0 mmol) of 2-[(1-tert-Butyloxycarbonyl)piperidin-4-yl]-4-(4,4-difluorocyclohexyl)-3-formyl-7,7-dimethyl-5,6,7,8-tetrahydroquinolin-5-ol, which was prepared by a method similar to that of Reference Example 5, in 50 ml N,N-dimethylformamide was added under ice cooling, and the reaction solution was stirred for 0.5 hours. Then, 2.7 ml (19 mmol) of p-methoxybenzyl bromide was added thereto and the reaction solution was stirred under ice cooling for 2 hours and then at room temperature for 1.5 hours. After completion of the reaction, the reaction solution was poured into saturated sodium hydrogencarbonate aqueous solution and extracted with ethyl acetate. The obtained organic layer was washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=90/10-70/30 (V/V)] and the fraction including the desired compound was concentrated under reduced pressure to provide 6.97 g of the title compound as a white solid (yield: 49%).

$^1$H-NMR spectrum (300 MHz, CDCl$_3$) δ ppm: 10.76 (1H, s), 7.23 (2H, d, J=9 Hz), 6.86 (2H, d, J=9 Hz), 4.80 (1H, dd, J=9, 5 Hz), 4.77 (1H, d, J=11 Hz), 4.36 (1H, d, J=11 Hz), 4.29-4.08 (2H, m), 3.79 (3H, s), 3.14-2.67 (3H, m), 3.08 (1H, tt, J=11, 3 Hz), 2.92 (1H, d, J=17 Hz), 2.67 (1H, d, J=17 Hz), 2.26-1.50 (14H, m), 1.47 (9H, s), 1.19 (3H, s), 1.04 (3H, s).

Mass spectrum (CI, m/z): 627 [(M+1)$^+$].

Reference Example 7

2-[(1-tert-Butyloxycarbonyl)piperidin-4-yl]-4-(4,4-difluorocyclohexyl)-3-{hydroxy[4-(trifluoromethyl)phenyl]methyl}-5-[(4-methoxybenzyl)oxy]-7,7-dimethyl-5,6,7,8-tetrahydroquinoline

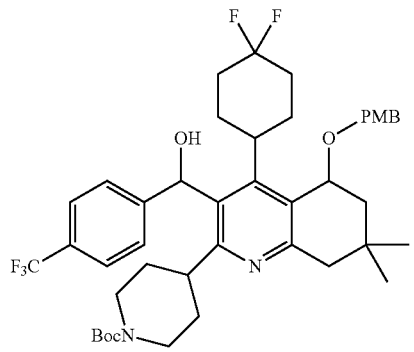

To a solution of 7.52 g (12.0 mmol) of 2-[(1-tert-Butyloxycarbonyl)piperidin-4-yl]-4-(4,4-difluorocyclohexyl)-3-formyl-5-[(4-methoxybenzyl)oxy]-7,7-dimethyl-5,6,7,8-tetrahydroquinoline, which was prepared by a method similar to that of Reference Example 6, in 60 ml of tetrahydrofuran, 48 ml (corresponding to 24.0 mmol) of tetrahydrofuran solution of 4-trifluoromethylphenyl magnesium bromide, which was prepared from 16.5 g (73.5 mmol) of 4-trifluoromethylphenyl bromide, 1.70 g (70.0 mmol) of magnesium and 140 ml of tetrahydrofuran, was added dropwise under ice cooling. After completion of the dropwise addition above, the reaction solution was stirred at room temperature for 2.3 hours. After completion of the reaction, the reaction solution was added to saturated ammonium chloride aqueous solution and extracted with ethyl acetate. The obtained organic layer was washed with saturated sodium hydrogencarbonate aqueous solution and saturated sodium chloride aqueous solution in order and dried with anhydrous magnesium sulfate, and then the solvent was distilled off under reduced pressure. The obtained residue was subjected to silica gel column chromatography [n-hexane/ethyl acetate=90/10-70/30 (V/V)] three times to provide Diastereomer 1 eluting earlier as a foam and 3.18 g (yield: 34%) of Diastereomer 2 eluting later as a foam for the title compound.

[Diastereomer 1]

Rf value: 0.29 [n-hexane/ethyl acetate=7/3 (V/V)].

$^1$H-NMR spectrum (300 MHz, CDCl$_3$) δ ppm: 7.57 (2H, d, J=8 Hz), 7.37 (2H, d, J=8 Hz), 7.25 (2H, d, J=9 Hz), 6.87 (2H, d, J=9 Hz), 6.43 (1H, s), 4.83 (1H, d, J=11 Hz), 4.81 (1H, t, J=5 Hz), 4.38 (1H, d, J=11 Hz), 4.25-4.02 (1H, m), 3.83-3.75 (1H, m), 3.80 (3H, s), 3.24-2.42 (3H, m), 2.86 (1H, d, J=17 Hz), 2.65 (1H, d, J=17 Hz), 2.29-1.52 (15H, m), 1.41 (9H, s), 1.20 (3H, s), 1.09 (3H, s), 0.50-0.40 (1H, m).

Mass spectrum (CI, m/z): 773 [(M+1)$^+$].

[Diastereomer 2]

Rf value: 0.21 [n-hexane/ethyl acetate=7/3 (V/V)].

$^1$H-NMR spectrum (300 MHz, CDCl$_3$) δ ppm: 7.56 (2H, d, J=8 Hz), 7.39 (2H, d, J=8 Hz), 7.26 (2H, d, J=9 Hz), 6.88 (2H, d, J=9 Hz), 6.43 (1H, s), 4.83 (1H, t, J=5 Hz), 4.81 (1H, d, J=11 Hz), 4.39 (1H, d, J=11 Hz), 4.27-4.02 (1H, m), 3.84-3.70 (1H, m), 3.80 (3H, s), 3.23-2.47 (3H, m), 2.86 (1H, d, J=17 Hz), 2.65 (1H, d, J=17 Hz), 2.32-2.06 (4H, m), 2.03-1.50 (11H, m), 1.41 (9H, s), 1.21 (3H, s), 1.04 (3H, s), 0.47-0.37 (1H, m).

Mass spectrum (CI, m/z): 773 [(M+1)$^+$].

Reference Example 8

2-[(1-tert-Butyloxycarbonyl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline (diastereomer 2)

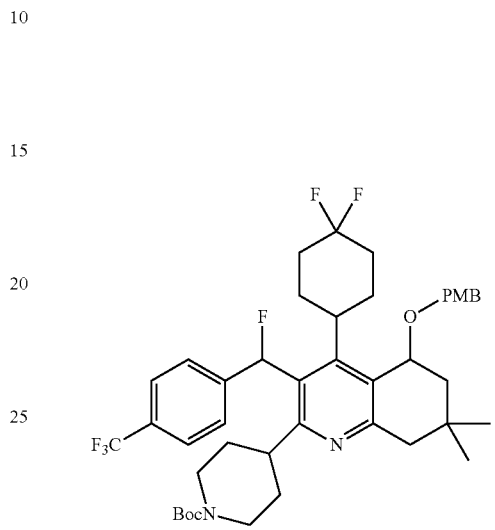

To a solution of 3.09 g (4.00 mmol) of 2-[(1-tert-Butyloxycarbonyl)piperidin-4-yl]-4-(4,4-difluorocyclohexyl)-3-{hydroxy[4-(trifluoromethyl)phenyl]methyl}-5-[(4-methoxybenzyl)oxy]-7,7-dimethyl-5,6,7,8-tetrahydroquinoline (Diastereomer 2), which was prepared by a method similar to that of Reference Example 7, in 12 ml of dichloromethane, 1.47 ml (8.00 mmol) of bis(methoxyethyl)aminosulfur trifluoride was added under cooling with a dry ice-acetone bath, and the reaction solution was stirred under the same conditions for 5.3 hours. Furthermore, 0.15 ml (0.800 mmol) of bis(methoxyethyl)aminosulfur trifluoride was added thereto and the reaction solution was stirred under the same conditions for 1 hour. After completion of the reaction, the reaction solution was added to a mixed solution of ice and saturated sodium hydrogencarbonate aqueous solution and extracted with chloroform. The obtained organic layer was washed with saturated sodium chloride aqueous solution and dried with anhydrous magnesium sulfate, and then the solvent was distilled off under reduced pressure. Cyclohexane was added to the obtained residue and the precipitate was obtained by filtration to provide 2.55 g of the title compound as a white solid (yield: 82%).

$^1$H-NMR spectrum (300 MHz, CDCl$_3$) δ ppm: 7.60 (2H, d, J=8 Hz), 7.33 (2H, d, J=8 Hz), 7.25 (2H, d, J=9 Hz), 7.12 (1H, d, J=49 Hz), 6.87 (2H, d, J=9 Hz), 4.83 (1H, t, J=5 Hz), 4.81 (1H, d, J=11 Hz), 4.39 (1H, d, J=11 Hz), 4.20-4.01 (1H, m), 3.90-3.74 (1H, m), 3.79 (3H, s), 3.24-3.08 (1H, m), 2.88 (1H, d, J=17 Hz), 2.68 (1H, d, J=17 Hz), 2.68-2.46 (2H, m), 2.32-2.08 (3H, m), 2.00-1.37 (11H, m), 1.41 (9H, s), 1.21 (3H, s), 1.05 (3H, s), 0.63-0.51 (1H, m).

Mass spectrum (CI, m/z): 775 [(M+1)$^+$].

Reference Example 9

4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline (diastereomer 2)

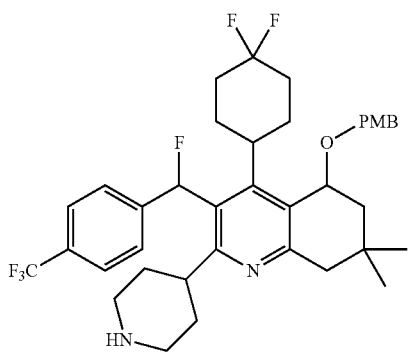

To a solution of 387 mg (0.500 mmol) of 2-[(1-tert-Butyloxycarbonyl)piperidin-4-yl]-4-(4,4-difluorocyclohexyl)-3-{fluoro[4-(trifluoromethyl)phenyl]methyl}-5-[(4-methoxybenzyl)oxy]-7,7-dimethyl-5,6,7,8-tetrahydroquinoline (Diastereomer 2), which was prepared by a method similar to that of Reference Example 8, in 2.5 ml of dichloromethane, 236 mg (1.05 mmol) of zinc bromide was added, and then the reaction solution was stirred at 30° C. for 68.5 hours. After completion of the reaction, the reaction solution was subjected to aminopropyl group-modified silica gel column chromatography [n-hexane/ethyl acetate/methanol=50/50/0-0/100/0-0/90/10 (V/V/V)] and the fraction including the desired compound was concentrated under reduced pressure to provide 320 mg of the title compound as a foam (yield: 95%).

$^1$H-NMR spectrum (300 MHz, CDCl$_3$) δ ppm: 7.60 (2H, d, J=8 Hz), 7.33 (2H, d, J=8 Hz), 7.25 (2H, d, J=9 Hz), 7.11 (1H, d, J=47 Hz), 6.87 (2H, d, J=9 Hz), 4.83 (1H, t, J=5 Hz), 4.81 (1H, d, J=11 Hz), 4.39 (1H, d, J=11 Hz), 3.79 (3H, s), 3.23-2.98 (2H, m), 2.95-2.55 (4H, m), 2.48 (1H, td, J=12, 2 Hz), 2.33-2.08 (3H, m), 2.01-1.47 (11H, m), 1.22 (3H, s), 1.06 (3H, s), 0.62-0.51 (1H, m).

Mass spectrum (CI, m/z): 675 [(M+1)$^+$].

Reference Example 10

(−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline 10 g of 4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline (Diastereomer 2), which was prepared by a method similar to that of Reference Example 9, was optically resolved by high performance liquid chromatography [CHIRALPAK (trade name) AD-H 5cmID×25cmL (manufactured by Daicel Chemical Industries, Ltd.), eluent: n-hexane/2-propanol/isopropylamine=80/20/0.1 (V/V/V)] to provide 4.2 g of the title compound eluting later as a white solid.

[Title compound]

Specific optical rotation: $[α]_D^{24}$=−101° (C=0.25, methanol).

$^1$H-NMR spectrum (300 MHz, CD$_2$Cl$_2$) δ ppm: 7.61 (2H, d, J=8 Hz), 7.35 (2H, d, J=8 Hz), 7.26 (2H, d, J=9 Hz), 7.14 (1H, d, J=47 Hz), 6.86 (2H, d, J=9 Hz), 4.85 (1H, t, J=5 Hz), 4.80 (1H, d, J=11 Hz), 4.39 (1H, d, J=11 Hz), 3.77 (3H, s), 3.25-3.09 (1H, m), 3.03-2.93 (1H, m), 2.92-2.80 (1H, m), 2.75-2.53 (3H, m), 2.45 (1H, td, J=12, 3 Hz), 2.30-2.11 (3H, m), 2.00-1.39 (11H, m), 1.20 (3H, s), 1.07 (3H, s), 0.61-0.51 (1H, m).

Mass spectrum (CI, m/z): 675 [(M+1)$^+$].

Analysis conditions of the high performance liquid chromatography:

Column: CHIRALPAK (trade name) AD-H (0.46 cm ID×25 cm, manufactured by Daicel Chemical Industries, Ltd.)

Eluent: n-hexane/2-propanol/isopropylamine=80/20/0.1 (V/V/V)

Flow rate: 1.0 ml/min

Column temperature: 40° C.

Detection wavelength: 271 nm

Retention time: 5.5 minutes

From the results of Reference Example 11, the name of a compound including the absolute configuration of the compound of Reference Example 10 was shown to be (5S)-4-(4,4-Difluorocyclohexyl)-3-{(S)-fluoro[4-(trifluoromethyl)

phenyl]methyl}-5-[(4-methoxybenzyl)oxy]-7,7-dimethyl-2-(piperidin-4-yl)-5,6,7,8-tetrahydroquinoline.

Reference Example 11

(5S)-4-(4,4-Difluorocyclohexyl)-3-{(S)-fluoro[4-(trifluoromethyl)phenyl]methyl}-2-[1-((R)-2-hydroxy-2-phenylacetyl)piperidin-4-yl]-5-[(4-methoxybenzyl)oxy]-7,7-dimethyl-5,6,7,8-tetrahydroquinoline

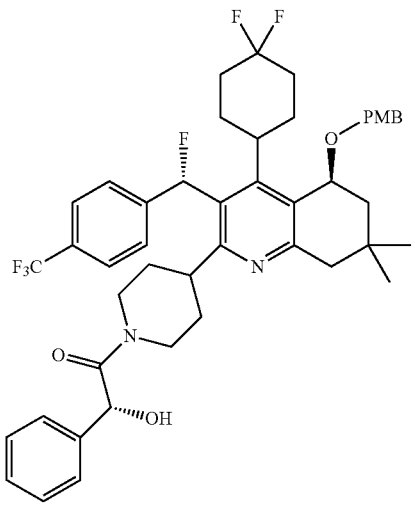

(11-1) Preparation of title compound

To 501 mg (0.742 mmol) of (−)-4-(4,4-Difluorocyclohexyl)-3-{fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was obtained by a method similar to that of Reference Example 10, 113 mg (0.743 mmol) of (R)-D-(−)-mandelic acid, 255 μl (1.46 mmol) of diisopropylethylamine and 5 ml of methylene chloride were added. Then, 143 mg (0.746 mmol) of 1-(3-dimethylaminopropyl)-3-ethylcarbodiimide hydrochloride was added to the reaction solution and the reaction solution was stirred at room temperature for 20 hours. Furthermore, 143 mg (0.746 mmol) of 1-(3-dimethylaminopropyl)-3-ethylcarbodiimide hydrochloride and 133 mg (1.09 mmol) of 4-dimethylaminopyridine were added to the reaction solution and the reaction solution was stirred at room temperature for 4 days. Water was added to the reaction solution and the reaction solution was extracted with methylene chloride three times. After drying with anhydrous magnesium sulfate, the solvent was distilled off under reduced pressure. The obtained residue was subjected to silica gel column chromatography [n-hexane/ethyl acetate=80/20 (V/V)] to provide 156 mg of the title compound as a white solid (yield: 26%).

$^1$H-NMR spectrum (300 MHz, $CD_2Cl_2$) δ ppm: 7.61, 7.54 (total 2H, each d, J=8 Hz), 7.42-6.98 (10H, m), 6.85 (2H, d, J=8 Hz), 5.11 (1H, d, J=6 Hz), 4.88-4.28 (2H, m), 4.80, 4.78 (total 1H, each d, J=10, 11 Hz), 4.71, 4.66 (total 1H, each d, J=6, 7 Hz), 4.38, 4.37 (total 1H, each d, J=11 Hz), 3.76 (3H, s), 3.63-3.53, 3.45-3.34 (total 1H, each m), 3.24-3.05 (1H, m), 2.91-2.39 (4H, m), 2.29-2.06 (3H, m), 2.01-1.43 (11H, m), 1.19 (3H, s), 1.06, 1.05 (total 3H, each s), 0.76-0.58 (1H, m).

Mass spectrum (APCI POSITIVE, m/z): 809 [(M+1)$^+$].

(11-2) Determination of absolute configuration of title compound

800 μl of methanol was added to 3.5 mg of the title compound obtained in Reference Example (11-1) and it was dissolved and then methanol was slowly and naturally evaporated to provide a needle-shaped monocrystal. X ray crystalline structure analysis was performed for the obtained monocrystal.

The diffraction intensity data were collected under an extremely low temperature air current (−150° C.) using an apparatus for analyzing monocrystalline X ray structure, Rigaku R-AXIS RAPID. After determination of the structure with the direct method using software CrystalStructure, structure refinement was performed with full-matrix least-squares method, wherein the temperature factor of non-hydrogen atoms was anisotropic and the temperature factor of a hydrogen atom was isotropic. The obtained crystallographic data were $C_{46}H_{50}F_6N_2O_4$, $M_w$=808.90, monoclinic system, space group $P2_1$, a=6.24540 (19) Å, b=22.2621 (7) Å, c=14.9460 (4) Å, β=90.3970 (19)°, V=2077.97 (11) Å$^3$, Z=2 and $D_{calc}$=1.293 g/cm$^3$. Final R value 0.0599 was obtained for 24045 reflections.

From the fact that the absolute configuration of the asymmetric carbon of the mandelic acid part introduced into the compound was the configuration R, the absolute configurations of the other asymmetric carbons of the title compound were determined. The absolute configuration of the carbon at the 5-position of 5,6,7,8-tetrahydroquinoline was the configuration S and the absolute configuration of the carbon at the 1-position of the fluoro[4-(trifluoromethyl)phenyl]methyl group was the configuration S, and the chemical structural formula including the absolute configurations of the title compound was as shown above.

Reference Example 12

5-[(tert-Butyldimethylsilyl)oxy]-2-chloropyrimidine

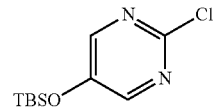 [SMILES: CC(C)(C)[Si](C)(C)Oc1cnc(Cl)nc1]

To a solution of 20.2 g (0.154 mol) of 2-chloro-5-hydroxypyrimidine in 150 ml of N,N-dimethylformamide, 15.8 g (0.232 mol) of imidazole and 26.8 g (0.178 mol) of tert-butyldimethylsilyl chloride were added, and the reaction mixture was stirred at room temperature for 2.5 hours. After completion of the reaction, the reaction solution was poured into water and extracted with n-heptane three times. The obtained organic phases were combined, washed with 0.01 N sodium hydroxide aqueous solution, water and saturated sodium chloride aqueous solution in order and dried with anhydrous magnesium sulfate, and then the solvent was distilled off under reduced pressure to provide 39.5 g of the title compound as a white solid (yield: 100%).

$^1$H-NMR spectrum (300 MHz, $CD_2Cl_2$) δ: 8.21 (2H, s), 1.00 (9H, s), 0.25 (6H, s).

Mass spectrum (EI, m/z): 244 [M$^+$].

Reference Example 13

(5S)-2-(1-{5-[(tert-Butyldimethylsilyl)oxy]pyrimidin-2-yl}piperidin-4-yl)-4-(4,4-difluorocyclohexyl)-3-{(S)-fluoro[4-(trifluoromethyl)phenyl]methyl}-5-[(4-methoxybenzyl)oxy]-7,7-dimethyl-5,6,7,8-tetrahydroquinoline

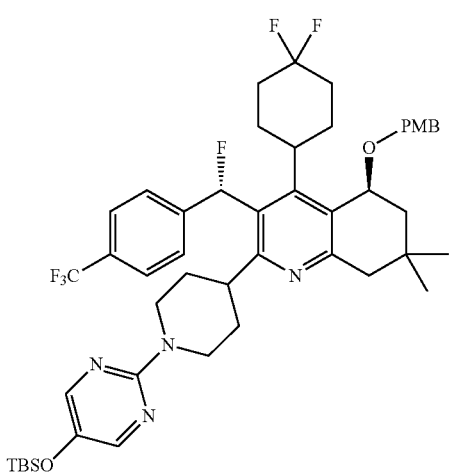

To a solution of 2.00 g (2.96 mmol) of (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, in 4 ml of 1,4-dioxane, 1.45 g (5.92 mmol) of 5-[(tert-butyldimethylsilyl)oxy]-2-chloropyrimidine, which was prepared by a method similar to that of Reference Example 12, and 1.22 g (8.83 mmol) of potassium carbonate were added, and the reaction mixture was stirred at 120° C. for 20.5 hours. After completion of the reaction, water was added to the reaction solution and the reaction solution was extracted with ethyl acetate twice. The obtained organic phases were combined and washed with saturated sodium chloride aqueous solution, and then the solvent was distilled off under reduced pressure. The obtained residue was subjected to silica gel column chromatography [n-hexane/ethyl acetate=95/5-78/22 (V/V)] and the fraction including the desired compound was concentrated under reduced pressure to provide 2.31 g of the title compound as a white solid (yield: 88%).

$^1$H-NMR spectrum (400 MHz, $CD_2Cl_2$) δ: 7.92 (2H, s), 7.66-7.61 (2H, m), 7.40-7.36 (2H, m), 7.28-7.24 (2H, m), 7.17 (1H, d, J=47.4 Hz), 6.88-6.84 (2H, m), 4.88-4.83 (1H, m), 4.80 (1H, d, J=10.8 Hz), 4.66-4.59 (1H, m), 4.39 (1H, d, J=10.9 Hz), 4.38-4.32 (1H, m), 3.77 (3H, s), 3.24-3.12 (1H, m), 2.89-2.60 (4H, m), 2.31-1.34 (14H, m), 1.18 (3H, s), 1.04 (3H, s), 0.97 (9H, s), 0.71-0.63 (1H, m), 0.16 (6H, s).

Mass spectrum (EI, m/z): 882 [M$^+$].

Reference Example 14

2-[4-((5S)-4-(4,4-Difluorocyclohexyl)-3-{(S)-fluoro[4-(trifluoromethyl)phenyl]methyl}-5-[(4-methoxybenzyl)oxy]-7,7-dimethyl-5,6,7,8-tetrahydroquinolin-2-yl)piperidin-1-yl]pyrimidin-5-ol

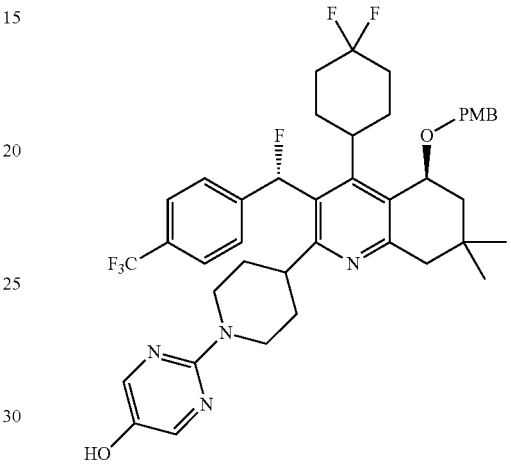

To a solution of 1.00 g (1.13 mmol) of (5S)-2-(1-{5-[(tert-Butyldimethylsilyl)oxy]pyrimidin-2-yl}piperidin-4-yl)-4-(4,4-difluorocyclohexyl)-3-{(S)-fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 13, in 2 ml of tetrahydrofuran, 1.5 ml of a solution of 1.0 M tetra-n-butylammonium fluoride in tetrahydrofuran was added, and the reaction mixture was stirred at room temperature for 2 hours. After completion of the reaction, toluene and water were added to the reaction solution to separate an organic phase. Further, the reaction mixture was extracted with toluene from the aqueous phase. The obtained organic phases were combined and washed with saturated sodium chloride aqueous solution, and then the solvent was distilled off under reduced pressure. The obtained residue was subjected to silica gel column chromatography [n-hexane/ethyl acetate=78/22-55/45 (V/V)] and the fraction including the desired compound was concentrated under reduced pressure to provide 861 mg of the title compound as a white solid (yield: 99%).

$^1$H-NMR spectrum (400 MHz, $CD_2Cl_2$) δ: 7.93 (2H, s), 7.66-7.61 (2H, m), 7.41-7.35 (2H, m), 7.28-7.11 (3H, m), 6.89-6.83 (2H, m), 5.55 (1H, s), 4.88-4.82 (1H, m), 4.80 (1H, d, J=10.8 Hz), 4.63-4.57 (1H, m), 4.39 (1H, d, J=10.8 Hz), 4.36-4.29 (1H, m), 3.77 (3H, s), 3.24-3.13 (1H, m), 2.84-2.58 (4H, m), 2.31-1.32 (14H, m), 1.15 (3H, s), 1.02 (3H, s), 0.67-0.60 (1H, m).

Mass spectrum (EI, m/z): 768 [M$^+$].

Reference Example 15

4-{[2-(4-{(S)-4-(4,4-Difluorocyclohexyl)-3-{(S)-fluoro[4-(trifluoromethyl)phenyl]methyl}-5-[(4-methoxybenzyl)oxy]-7,7-dimethyl-5,6,7,8-tetrahydroquinolin-2-yl)piperidin-1-yl]pyrimidine-5-oxy}-2-methylbutan-2-ol

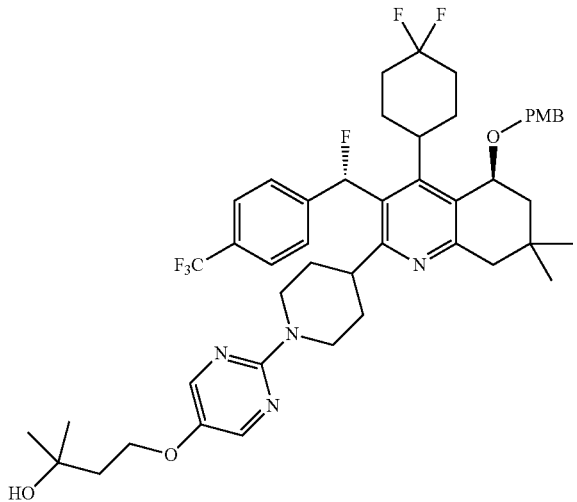

To 570 mg (0.741 mmol) of 2-[4-((5S)-4-(4,4-Difluorocyclohexyl)-3-{(S)-fluoro[4-(trifluoromethyl)phenyl]methyl}-5-[(4-methoxybenzyl)oxy]-7,7-dimethyl-5,6,7,8-tetrahydroquinolin-2-yl)piperidin-1-yl]pyrimidin-5-ol, which was prepared by a method similar to that of Reference Example 14, 288 mg (1.11 mmol) of 3-hydroxy-3-methylbutyl toluenesulfonate and 198 mg (1.43 mmol) of potassium carbonate, 2 ml of N,N-dimethylformamide was added, and the reaction mixture was stirred at 80° C. for 2.8 hours. After completion of the reaction, toluene and water were added to the reaction solution to separate an organic phase. Further, the reaction mixture was extracted with toluene from the aqueous phase. The obtained organic phases were combined and washed with saturated sodium chloride aqueous solution, and then the solvent was distilled off under reduced pressure. The obtained residue was subjected to silica gel column chromatography [n-hexane/ethyl acetate=78/22-50/50 (V/V)] and the fraction including the desired compound was concentrated under reduced pressure. The obtained residue was dissolved in ethyl acetate, then n-heptane was added thereto, and the precipitate was obtained by filtration to provide 455 mg of the title compound as a white solid (yield: 72%).

$^1$H-NMR spectrum (400 MHz, $CD_2Cl_2$) δ: 8.03 (2H, s), 7.66-7.61 (2H, m), 7.41-7.35 (2H, m), 7.29-7.24 (2H, m), 7.17 (1H, d, J=47.6 Hz), 6.89-6.83 (2H, m), 4.88-4.83 (1H, m), 4.80 (1H, d, J=10.8 Hz), 4.68-4.60 (1H, m), 4.39 (1H, d, J=10.8 Hz), 4.39-4.34 (1H, m), 4.10 (2H, t, J=6.5 Hz), 3.77 (3H, s), 3.25-3.12 (1H, m), 2.87-2.59 (4H, m), 2.32-1.35 (14H, m), 1.92 (2H, t, J=6.5 Hz), 1.89 (1H, s), 1.26 (6H, s), 1.18 (3H, s), 1.04 (3H, s), 0.70-0.63 (1H, m).

Mass spectrum (EI, m/z): 854 [M$^+$].

Reference Example 16

(5S)-4-(4,4-Difluorocyclohexyl)-3-{(S)-fluoro[4-(trifluoromethyl)phenyl]methyl}-2-{1-[5-(3-hydroxy-3-methylbutoxy)pyrimidin-2-yl]piperidin-4-yl}-7,7-dimethyl-5,6,7,8-tetrahydroquinolin-5-ol

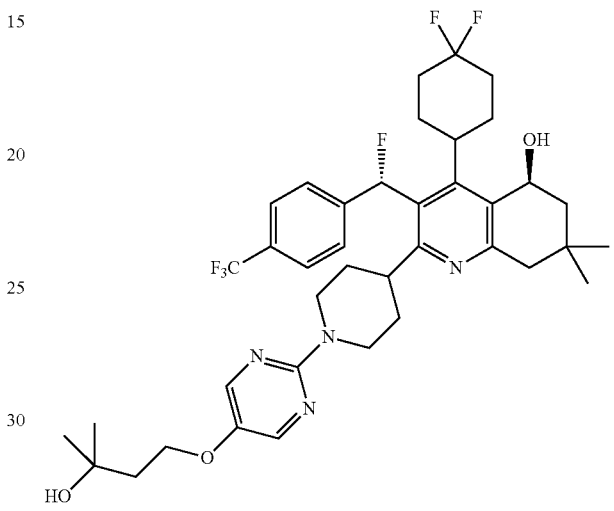

To a solution of 448 mg (0.524 mmol) of 4-{[2-(4-{(S)-4-(4,4-Difluorocyclohexyl)-3-{(S)-fluoro[4-(trifluoromethyl)phenyl]methyl}-5-[(4-methoxybenzyl)oxy]-7,7-dimethyl-5,6,7,8-tetrahydroquinolin-2-yl)piperidin-1-yl]pyrimidine-5-oxy}-2-methylbutan-2-ol, which was prepared by a method similar to that of Reference Example 15, in 5 ml of 1,4-dioxane, 5 ml of 2 N hydrochloric acid was added, and the reaction mixture was stirred at 80° C. for 5 hours. After completion of the reaction, the reaction solution was poured into saturated sodium hydrogencarbonate aqueous solution and extracted with ethyl acetate twice. The obtained organic phases were combined and washed with saturated sodium chloride aqueous solution, and then the solvent was distilled off under reduced pressure. The obtained residue was subjected to silica gel column chromatography [n-hexane/ethyl acetate=78/22-45/55 (V/V)] and the fraction including the desired compound was concentrated under reduced pressure. n-Heptane was added to the obtained residue, and the precipitate was obtained by filtration to provide 343 mg of the title compound as a white solid (yield: 89%).

$^1$H-NMR spectrum (400 MHz, $CD_2Cl_2$) δ: 8.04 (2H, s), 7.68-7.62 (2H, m), 7.42-7.36 (2H, m), 7.22 (1H, d, J=47.2 Hz), 5.17-5.09 (1H, m), 4.69-4.61 (1H, m), 4.41-4.32 (1H, m), 4.10 (2H, t, J=6.4 Hz), 3.69-3.58 (1H, m), 2.83-2.57 (4H, m), 2.34-1.56 (15H, m), 1.92 (2H, t, J=6.5 Hz), 1.90 (1H, s), 1.26 (6H, s), 1.13 (3H, s), 1.00 (3H, s), 0.66-0.57 (1H, m).

Mass spectrum (EI, m/z): 734 [M$^+$].

Reference Example 17

2-Chloro-5-[(2,2,5-trimethyl-1,3-dioxan-5-yl)methoxy]pyrimidine

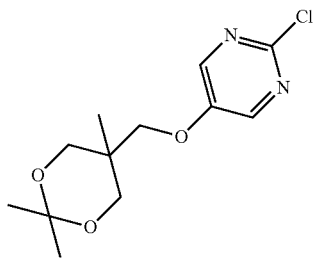 [SMILES: CC1(COc2cnc(Cl)nc2)COC(C)(C)OC1]

To a solution of 9.50 g (72.8 mmol) of 2-chloro-5-hydroxypyrimidine in 100 ml of N,N-dimethylformamide, 26.1 g (80.1 mmol) of cesium carbonate and 24.3 g (102 mmol) of 5-(methanesulfonyloxymethyl)-2,2,5-trimethyl-1,3-dioxane, which was synthesized by the method described in V. W. Gash, Journal of Organic Chemistry, 1972, Vol. 37, p. 2197-2201, were added, and the mixture was stirred at 90° C. for 24 hours. After completion of the reaction, the insoluble material was filtered off and washed with ethyl acetate, and then 0.5 N sodium hydroxide aqueous solution was added to the filtrate and separation was performed. The obtained aqueous layer was further extracted with ethyl acetate. The obtained organic layers were combined, washed with water and saturated sodium chloride aqueous solution in order and dried with anhydrous magnesium sulfate, and then the solvent was distilled off under reduced pressure. Toluene was added to the obtained residue, and the precipitate was obtained by filtration and washed with toluene and n-heptane to provide 6.00 g of the title compound as a white solid (yield: 30%).

$^1$H-NMR spectrum (300 MHz, CDCl$_3$) δppm: 8.34 (2H, s), 4.16 (2H, s), 3.73 (4H, s), 1.47 (3H, s), 1.41 (3H, s), 0.94 (3H, s).

Reference Example 18

(5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-(1-{5-[(2,2,5-trimethyl-1,3-dioxan-5-yl)methoxy]pyrimidin-2-yl}piperidin-4-yl)-5,6,7,8-tetrahydroquinoline

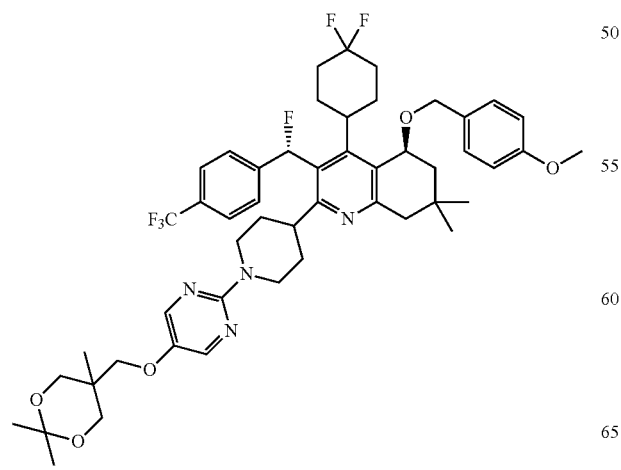

To 377 mg (0.559 mmol) of (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 127 mg (0.466 mmol) of 2-chloro-5-[(2,2,5-trimethyl-1,3-dioxan-5-yl)methoxy]pyrimidine, which was prepared by a method similar to that of Reference Example 17, and 154 mg (1.11 mmol) of potassium carbonate, 1 ml of 1,4-dioxane was added, and the reaction mixture was stirred at 120° C. for 26 hours. After completion of the reaction, water was added to the reaction solution and the reaction solution was extracted with ethyl acetate twice. The obtained organic phases were combined and washed with saturated sodium chloride aqueous solution, and then the solvent was distilled off under reduced pressure. The obtained residue was subjected to silica gel column chromatography [n-hexane/ethyl acetate=89/11-68/32 (V/V)] and the fraction including the desired compound was concentrated under reduced pressure to provide 391 mg of the title compound as a foam (yield: 92%).

$^1$H-NMR spectrum (400 MHz, CD$_2$Cl$_2$) δ: 8.05 (2H, s), 7.66-7.61 (2H, m), 7.41-7.35 (2H, m), 7.28-7.24 (2H, m), 7.17 (1H, d, J=47.4 Hz), 6.89-6.83 (2H, m), 4.88-4.82 (1H, m), 4.80 (1H, d, J=10.8 Hz), 4.67-4.61 (1H, m), 4.39 (1H, d, J=10.8 Hz), 4.39-4.33 (1H, m), 3.95 (2H, s), 3.77 (3H, s), 3.72 (2H, d, J=11.9 Hz), 3.64 (2H, d, J=11.9 Hz), 3.24-3.12 (1H, m), 2.86-2.60 (4H, m), 2.32-1.46 (14H, m), 1.42 (3H, s), 1.35 (3H, s), 1.18 (3H, s), 1.04 (3H, s), 0.91 (3H, s), 0.70-0.62 (1H, m).

Mass spectrum (EI, m/z): 910 [M$^+$].

Reference Example 19

(5S)-4-(4,4-Difluorocyclohexyl)-3-{(S)-fluoro[4-(trifluoromethyl)phenyl]methyl}-2-(1-{5-[3-hydroxy-2-(hydroxymethyl)-2-methylpropoxy]pyrimidin-2-yl}piperidin-4-yl)-7,7-dimethyl-5,6,7,8-tetrahydroquinolin-5-ol

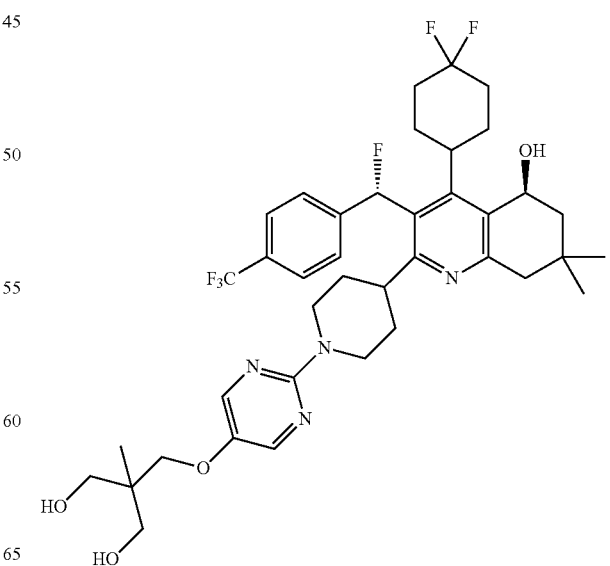

To a solution of 375 mg (0.411 mmol) of (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-(1-{5-[(2,2,5-trimethyl-1,3-dioxan-5-yl)methoxy]pyrimidin-2-yl}piperidin-4-yl)-5,6,7,8-tetrahydroquinoline, which was prepared by a method similar to that of Reference Example 18, in 5 ml of 1,4-dioxane, 1 ml of 6 N hydrochloric acid was added, and the reaction mixture was stirred at 80° C. for 3 hours. After completion of the reaction, the reaction solution was poured into saturated sodium hydrogencarbonate aqueous solution and extracted with ethyl acetate twice. The obtained organic phases were combined and washed with saturated sodium chloride aqueous solution, and then the solvent was distilled off under reduced pressure. The obtained residue was subjected to silica gel column chromatography [n-hexane/ethyl acetate=50/50-25/75 (V/V)] and the fraction including the desired compound was concentrated under reduced pressure. n-Heptane was added to the obtained residue, and the precipitate was obtained by filtration to provide 221 mg of the title compound as a white solid (yield: 72%).

$^1$H-NMR spectrum (400 MHz, CD$_2$Cl$_2$) δ: 8.04 (2H, s), 7.68-7.62 (2H, m), 7.41-7.36 (2H, m), 7.22 (1H, d, J=47.1 Hz), 5.16-5.09 (1H, m), 4.68-4.61 (1H, m), 4.40-4.32 (1H, m), 3.90 (2H, s), 3.70 (2H, dd, J=10.8, 5.6 Hz), 3.64-3.58 (1H, m), 3.64 (2H, dd, J=10.8, 5.3 Hz), 2.83-2.57 (4H, m), 2.34-1.57 (15H, m), 2.16 (2H, t, J=5.3 Hz), 1.13 (3H, s), 0.99 (3H, s), 0.92 (3H, s), 0.65-0.57 (1H, m).

Mass spectrum (EI, m/z): 750 [M$^+$].

Reference Example 20

2-Chloro-5-[(2,2-dimethyl-1,3-dioxan-5-yl)methoxy]pyrimidine

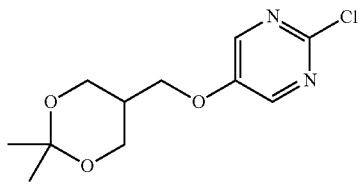 [SMILES: CC1(C)OCC(COc2cnc(Cl)nc2)CO1]

To 2.53 g (19.4 mmol) of 2-chloro-5-hydroxypyrimidine, a solution of 5.95 g (19.8 mmol) of 5-(toluenesulfonyloxymethyl)-2,2-dimethyl-1,3-dioxane in 11 ml of N-methylpyrrolidone and 6.50 g (19.9 mmol) of cesium carbonate were added, and the reaction mixture was stirred at 70° C. for 3.5 hours. After completion of the reaction, the reaction solution was poured into water and extracted with ethyl acetate twice. The obtained organic layers were combined, washed with water and saturated sodium chloride aqueous solution in order and dried with anhydrous sodium sulfate, and then the solvent was distilled off under reduced pressure. tert-Butyl methyl ether was added to the obtained residue, and the precipitate was obtained by filtration to provide 3.72 g of the title compound as a white solid (yield: 74%).

$^1$H-NMR spectrum (300 MHz, CD$_2$Cl$_2$) δ: 8.31 (2H, s), 4.22 (2H, d, J=7.1 Hz), 4.11 (2H, dd, J=12.5, 3.7 Hz), 3.82 (2H, dd, J=12.5, 4.2 Hz), 2.05 (1H, ttt, J=7.5, 3.8, 3.8 Hz), 1.44 (3H, s), 1.36 (3H, s).

Mass spectrum (CI, m/z): 259 [M$^+$1].

Reference Example 21

(5S)-4-(4,4-Difluorocyclohexyl)-2-(1-{5-[(2,2-dimethyl-1,3-dioxan-5-yl)methoxy]pyrimidin-2-yl}piperidin-4-yl)-3-{(S)-fluoro[4-(trifluoromethyl)phenyl]methyl}-5-[(4-methoxybenzyl)oxy]-7,7-dimethyl-5,6,7,8-tetrahydroquinoline

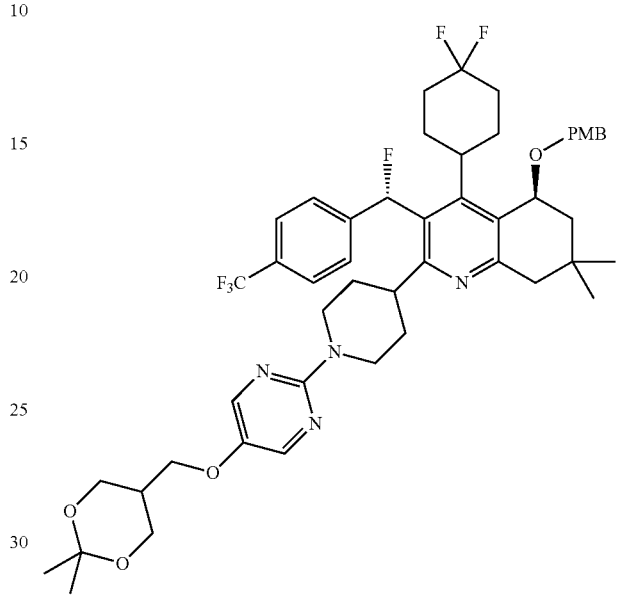

To 6.02 g (8.92 mmol) of (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, 2.16 g (8.35 mmol) of 2-chloro-5-[(2,2-dimethyl-1,3-dioxan-5-yl)methoxy]pyrimidine, which was prepared by a method similar to that of Reference Example 20, and 6.06 g (18.6 mmol) of cesium carbonate, 30 ml of 4-heptanol was added, and the reaction mixture was stirred at 150° C. for 8 hours. After completion of the reaction, the reaction solution was poured into water and extracted with ethyl acetate three times. The obtained organic phases were combined, washed with saturated sodium chloride aqueous solution and dried with anhydrous sodium sulfate, and then the solvent was distilled off under reduced pressure. Reaction and aftertreatment similar to those described above were further performed using 2.00 g (2.96 mmol) of (5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, 0.72 g (2.78 mmol) of 2-chloro-5-[(2,2-dimethyl-1,3-dioxan-5-yl)methoxy]pyrimidine and 2.02 g (5.73 mmol) of cesium carbonate. The obtained residues were combined and subjected to silica gel column chromatography [n-hexane/ethyl acetate=85/15-70/30 (V/V)] and the fraction including the desired compound was concentrated under reduced pressure. The obtained residue was dissolved in ethyl acetate, then n-heptane was added thereto, and the precipitate was obtained by filtration to provide 7.35 g of the title compound as a white solid (yield: 74%).

$^1$H-NMR spectrum (300 MHz, CD$_2$Cl$_2$) δ: 8.03 (2H, s), 7.67-7.60 (2H, m), 7.41-7.35 (2H, m), 7.29-7.08 (3H, m), 6.89-6.82 (2H, m), 4.88-4.81 (1H, m), 4.80 (1H, d, J=10.7 Hz), 4.68-4.59 (1H, m), 4.39-4.33 (1H, m), 4.39 (1H, d, J=10.7 Hz), 4.07-3.99 (4H, m), 3.83-3.76 (2H, m), 3.77 (3H, s), 3.27-3.09 (1H, m), 2.90-2.57 (4H, m), 2.33-1.55 (15H, m), 1.41 (3H, s), 1.36 (3H, s), 1.18 (3H, s), 1.04 (3H, s), 0.71-0.62 (1H, m).

Mass spectrum (EI, m/z): 896 [M+].

Reference Example 22

(5S)-4-(4,4-Difluorocyclohexyl)-3-{(S)-fluoro[4-(trifluoromethyl)phenyl]methyl}-2-(1-{5-[3-hydroxy-2-(hydroxymethyl)propoxy]pyrimidin-2-yl}piperidin-4-yl)-7,7-dimethyl-5,6,7,8-tetrahydroquinolin-5-ol

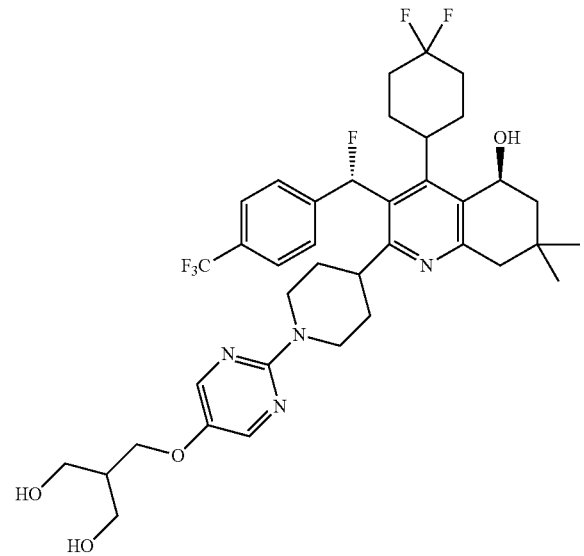 [SMILES: CC1(C)Cc2nc(C3CCN(c4ncc(OCC(CO)CO)cn4)CC3)c([C@@H](F)c3ccc(C(F)(F)F)cc3)c(C3CCC(F)(F)CC3)c2[C@@H](O)C1]

To a solution of 8.42 g (9.39 mmol) of (5S)-4-(4,4-Difluorocyclohexyl)-2-(1-{5-[(2,2-dimethyl-1,3-dioxan-5-yl)methoxy]pyrimidin-2-yl}piperidin-4-yl)-3-{(S)-fluoro[4-(trifluoromethyl)phenyl]methyl}-5-[(4-methoxybenzyl)oxy]-7,7-dimethyl-5,6,7,8-tetrahydroquinoline, which was prepared by a method similar to that of Reference Example 21, in 75 ml of 1,4-dioxane, 15 ml of 6 N hydrochloric acid was added, and the reaction mixture was stirred at 80° C. for 2 hours. After completion of the reaction, the reaction solution was poured into a mixed solution of saturated sodium hydrogencarbonate aqueous solution and 2 N sodium hydroxide aqueous solution and extracted with ethyl acetate three times. The obtained organic phases were combined, washed with saturated sodium chloride aqueous solution and dried with anhydrous magnesium sulfate, and then the solvent was distilled off under reduced pressure. The obtained residue was subjected to silica gel column chromatography [n-hexane/ethyl acetate=60/40-30/70 (V/V)] and the fraction including the desired compound was concentrated under reduced pressure. The obtained residue was dissolved in ethyl acetate, then n-heptane was added thereto, and the precipitate was obtained by filtration to provide 5.72 g of the title compound as a white solid (yield: 83%).

$^1$H-NMR spectrum (300 MHz, CD$_2$Cl$_2$) δ: 8.04 (2H, s), 7.68-7.62 (2H, m), 7.42-7.35 (2H, m), 7.22 (1H, d, J=47.1 Hz), 5.18-5.08 (1H, m), 4.70-4.60 (1H, m), 4.41-4.31 (1H, m), 4.03 (2H, d, J=5.9 Hz), 3.91-3.78 (4H, m), 3.71-3.57 (1H, m), 2.86-2.54 (4H, m), 2.36-1.57 (18H, m), 1.13 (3H, s), 0.99 (3H, s), 0.66-0.57 (1H, m).

Mass spectrum (EI, m/z): 736 [M+].

Reference Example 23

(5S)-4-(4,4-Difluorocyclohexyl)-3-{(S)-fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol

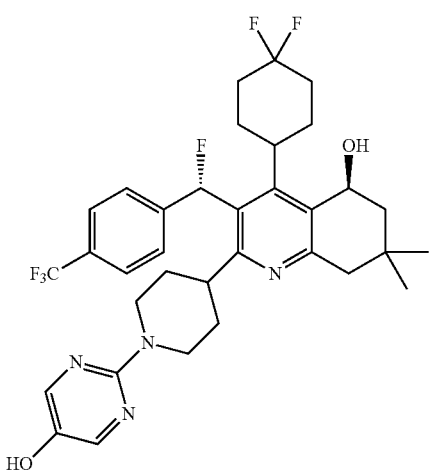 [SMILES: CC1(C)Cc2nc(C3CCN(c4ncc(O)cn4)CC3)c([C@@H](F)c3ccc(C(F)(F)F)cc3)c(C3CCC(F)(F)CC3)c2[C@@H](O)C1]

To a solution of 453 mg (0.589 mmol) of 2-[4-((5S)-4-(4,4-Difluorocyclohexyl)-3-{(S)-fluoro[4-(trifluoromethyl)phenyl]methyl}-5-[(4-methoxybenzyl)oxy]-7,7-dimethyl-5,6,7,8-tetrahydroquinolin-2-yl)piperidin-1-yl]pyrimidin-5-ol, which was prepared by a method similar to that of Reference Example 14, in 5 ml of 1,4-dioxane, 1 ml of 6 N hydrochloric acid was added, and the mixture was stirred at 80° C. for 4.5 hours. After completion of the reaction, the reaction solution was poured into saturated sodium hydrogencarbonate aqueous solution and extracted with ethyl acetate. The obtained organic phases were combined and washed with saturated sodium chloride aqueous solution, and then the solvent was distilled off under reduced pressure. The obtained residue was subjected to silica gel column chromatography [n-hexane/ethyl acetate=76/24-40/60 (V/V)] and the fraction including the desired compound was concentrated under reduced pressure to provide 360 mg of the title compound as a white solid (yield: 94%).

$^1$H-NMR spectrum (400 MHz, CD$_2$Cl$_2$) δ: 7.94 (2H, s), 7.68-7.63 (2H, m), 7.42-7.36 (2H, m), 7.23 (1H, d, J=47 Hz), 5.50 (1H, br s), 5.16-5.09 (1H, m), 4.65-4.57 (1H, m), 4.36-4.28 (1H, m), 3.70-3.58 (1H, m), 2.88-2.55 (4H, m), 2.34-1.58 (15H, m), 1.11 (3H, s), 0.98 (3H, s), 0.63-0.55 (1H, m).

Mass spectrum (EI, m/z): 648 [M+].

Reference Example 24

(5S)-4-(4,4-Difluorocyclohexyl)-2-[1-(5-{[(4R)-2,2-dimethyl-1,3-dioxolan-4-yl]methoxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol

Reference Example 25

(5S)-4-(4,4-Difluorocyclohexyl)-2-[1-(5-{[(2S)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol

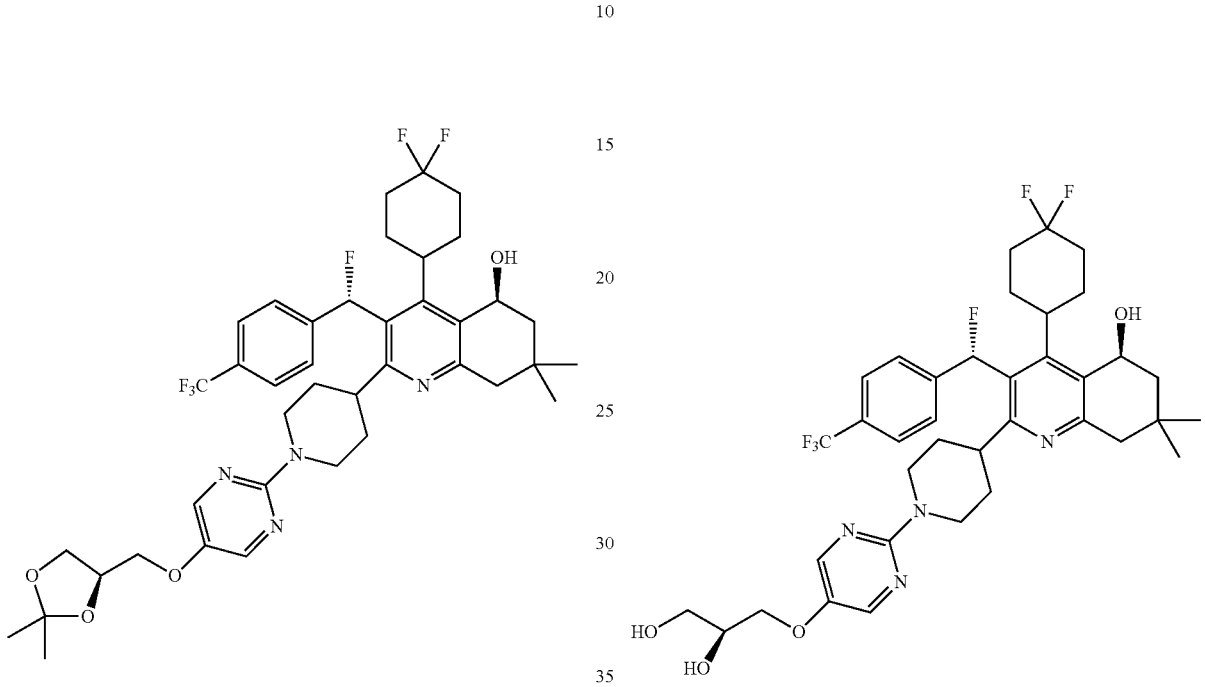

To a solution of 95.0 mg (0.146 mmol) of (5S)-4-(4,4-Difluorocyclohexyl)-3-{(S)-fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Reference Example 23, in 0.4 ml of N,N-dimethylformamide, 92.4 mg (0.322 mmol) of (S)-2,2-dimethyl-1,3-dioxolan-4-ylmethyl p-toluenesulfonate and 54.2 mg (0.392 mmol) of potassium carbonate were added, and the mixture was stirred at 90° C. for 5 hours. After completion of the reaction, the reaction solution was poured into water and extracted with toluene twice. The obtained organic phases were combined and washed with saturated sodium chloride aqueous solution, and then the solvent was distilled off under reduced pressure. The obtained residue was subjected to silica gel column chromatography [n-hexane/ethyl acetate=80/20-59/41 (V/V)] and the fraction including the desired compound was concentrated under reduced pressure to provide 91.3 mg of the title compound as a white solid (yield: 82%).

$^1$H-NMR spectrum (400 MHz, CD$_2$Cl$_2$) δ: 8.04 (2H, s), 7.68-7.62 (2H, m), 7.42-7.36 (2H, m), 7.22 (1H, d, J=47 Hz), 5.17-5.09 (1H, m), 4.69-4.61 (1H, m), 4.42-4.32 (2H, m), 4.10 (1H, dd, J=8, 6 Hz), 3.96 (1H, dd, J=10, 6 Hz), 3.89 (1H, dd, J=10, 5 Hz), 3.82 (1H, dd, J=8, 6 Hz), 3.70-3.58 (1H, m), 2.83-2.56 (4H, m), 2.36-1.56 (15H, m), 1.40 (3H, s), 1.35 (3H, s), 1.13 (3H, s), 1.00 (3H, s), 0.65-0.58 (1H, m).

Mass spectrum (EI, m/z): 762 [M$^+$].

To a solution of 86.7 mg (0.114 mmol) of (5S)-4-(4,4-Difluorocyclohexyl)-2-[1-(5-{[(4R)-2,2-dimethyl-1,3-dioxolan-4-yl]methoxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol, which was prepared by a method similar to that of Reference Example 24, in 2 ml of methanol, 0.5 ml of 2 N hydrochloric acid was added, and the mixture was stirred at 50° C. for 2.5 hours. After completion of the reaction, 0.5 ml of 2 N sodium hydroxide aqueous solution was added to the reaction solution, then saturated sodium chloride aqueous solution was poured thereinto, and the reaction solution was extracted with ethyl acetate. The obtained organic phases were combined, washed with saturated sodium chloride aqueous solution, dried with magnesium sulfate and then filtered, and the solvent was distilled off under reduced pressure to provide 77.1 mg of the title compound as a white solid (yield: 94%).

$^1$H-NMR spectrum (400 MHz, CD$_2$Cl$_2$) δ: 8.05 (2H, s), 7.68-7.63 (2H, m), 7.41-7.36 (2H, m), 7.22 (1H, d, J=47 Hz), 5.17-5.09 (1H, m), 4.69-4.62 (1H, m), 4.41-4.33 (1H, m), 4.05-3.91 (3H, m), 3.80-3.58 (3H, m), 2.83-2.57 (4H, m), 2.52 (1H, d, J=5 Hz), 2.34-1.56 (16H, m), 1.13 (3H, s), 1.00 (3H, s), 0.66-0.58 (1H, m).

Mass spectrum (EI, m/z): 722 [M$^+$].

Reference Example 26

(5S)-4-(4,4-Difluorocyclohexyl)-2-[1-(5-{[(4S)-2,2-dimethyl-1,3-dioxolan-4-yl]methoxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol

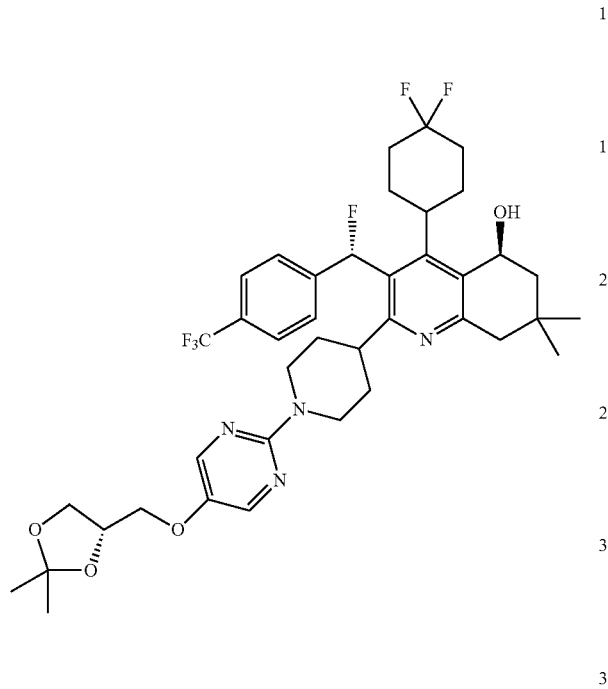

To a solution of 115 mg (0.177 mmol) of (5S)-4-(4,4-Difluorocyclohexyl)-3-{(S)-fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Reference Example 23, in 0.5 ml of N,N-dimethylformamide, 111 mg (0.388 mmol) of (R)-2,2-dimethyl-1,3-dioxolan-4-ylmethyl p-toluenesulfonate and 73.5 mg (0.532 mmol) of potassium carbonate were added, and the mixture was stirred at 90° C. for 4 hours. After completion of the reaction, the reaction solution was poured into water and extracted with toluene twice. The obtained organic phases were combined and washed with saturated sodium chloride aqueous solution, and then the solvent was distilled off under reduced pressure. The obtained residue was subjected to silica gel column chromatography [n-hexane/ethyl acetate=80/20-59/41 (V/V)] and the fraction including the desired compound was concentrated under reduced pressure to provide 113.3 mg of the title compound as a white solid (yield: 84%).

$^1$H-NMR spectrum (400 MHz, CD$_2$Cl$_2$) δ: 8.04 (2H, s), 7.68-7.62 (2H, m), 7.42-7.36 (2H, m), 7.22 (1H, d, J=47 Hz), 5.16-5.09 (1H, m), 4.69-4.61 (1H, m), 4.43-4.33 (2H, m), 4.10 (1H, dd, J=8, 6 Hz), 3.96 (1H, dd, J=10, 6 Hz), 3.90 (1H, dd, J=10, 5 Hz), 3.82 (1H, dd, J=8, 6 Hz), 3.70-3.58 (1H, m), 2.85-2.56 (4H, m), 2.34-1.56 (15H, m), 1.40 (3H, s), 1.35 (3H, s), 1.13 (3H, s), 1.00 (3H, s), 0.66-0.57 (1H, m).

Mass spectrum (EI, m/z): 762 [M$^+$].

Reference Example 27

(5S)-4-(4,4-Difluorocyclohexyl)-2-[1-(5-{[(2R)-2,3-dihydroxypropyl]oxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol

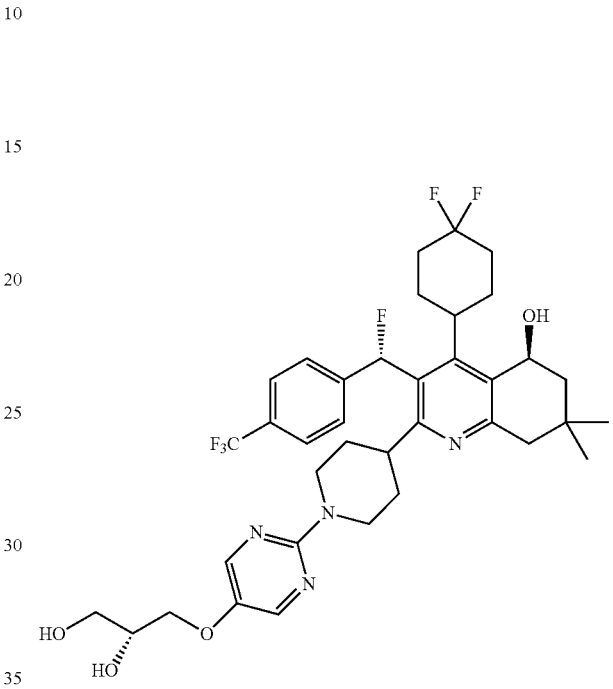

To a solution of 108.4 mg (0.142 mmol) of (5S)-4-(4,4-Difluorocyclohexyl)-2-[1-(5-{[(4S)-2,2-dimethyl-1,3-dioxolan-4-yl]methoxy}pyrimidin-2-yl)piperidin-4-yl]-3-{(S)-fluoro[4-(trifluoromethyl)phenyl]methyl}-7,7-dimethyl-5,6,7,8-tetrahydroquinolin-5-ol, which was prepared by a method similar to that of Reference Example 26, in 2 ml of methanol, 0.5 ml of 2 N hydrochloric acid was added, and the mixture was stirred at 50° C. for 3 hours. After completion of the reaction, 0.5 ml of 2 N sodium hydroxide aqueous solution was added to the reaction solution, then saturated sodium chloride aqueous solution was added, and the reaction solution was extracted with ethyl acetate. The obtained organic phases were combined, washed with saturated sodium chloride aqueous solution, dried with magnesium sulfate and then filtered, and the solvent was distilled off under reduced pressure to provide 101.2 mg of the title compound as a white solid (yield: 99%).

$^1$H-NMR spectrum (400 MHz, CD$_2$Cl$_2$) δ: 8.05 (2H, s), 7.68-7.63 (2H, m), 7.41-7.36 (2H, m), 7.22 (1H, d, J=47 Hz), 5.17-5.09 (1H, m), 4.70-4.62 (1H, m), 4.40-4.34 (1H, m), 4.05-3.91 (3H, m), 3.80-3.59 (3H, m), 2.84-2.57 (4H, m), 2.54 (1H, d, J=4 Hz), 2.35-1.58 (16H, m), 1.13 (3H, s), 1.00 (3H, s), 0.66-0.57 (1H, m).

Mass spectrum (EI, m/z): 722 [M$^+$].

Reference Example 28

(5S)-4-(4,4-Difluorocyclohexyl)-3-{(S)-fluoro[4-(trifluoromethyl)phenyl]methyl}-7,7-dimethyl-2-(1-{5-[3-(methylsulfonyl)propoxy]pyrimidin-2-yl}piperidin-4-yl)-5,6,7,8-tetrahydroquinolin-5-ol

Reference Example 29

Methyl 3-(2-chloropyrimidin-5-yl)benzoate

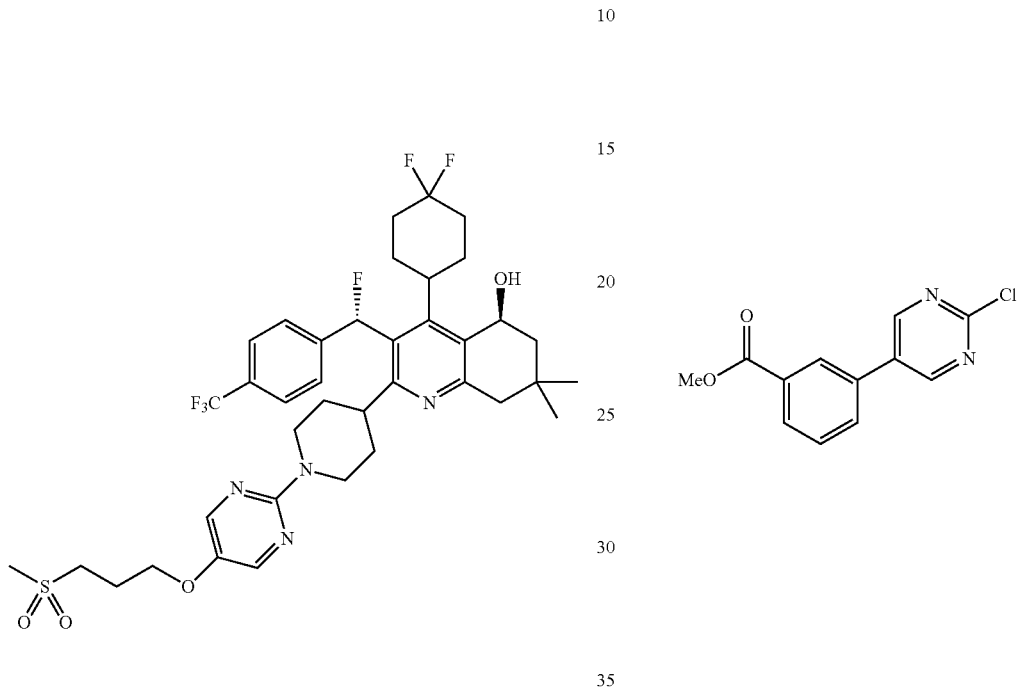

To a solution of 145 mg (0.224 mmol) of (5S)-4-(4,4-Difluorocyclohexyl)-3-{(S)-fluoro[4-(trifluoromethyl)phenyl]methyl}-2-[1-(5-hydroxypyrimidin-2-yl)piperidin-4-yl]-7,7-dimethyl-5,6,7,8-tetrahydroquinolin-5-ol, which was prepared by a method similar to that of Reference Example 23, in 0.7 ml of N,N-dimethylformamide, 130 mg (0.445 mmol) of 3-(methylsulfonyl)propyl p-toluenesulfonate and 135 mg (0.977 mmol) of potassium carbonate were added, and the mixture was stirred at 80° C. for 4 hours. 44 mg (0.337 mmol) of 2-chloro-5-hydroxypyrimidine was further added thereto, and the mixture was stirred at 80° C. for 3 hours. After completion of the reaction, the reaction solution was poured into water and extracted with toluene twice. The obtained organic phases were combined and washed with saturated sodium chloride aqueous solution, and then the solvent was distilled off under reduced pressure. The obtained residue was subjected to silica gel column chromatography [n-hexane/ethyl acetate=55/45-25/75 (V/V)] and the fraction including the desired compound was concentrated under reduced pressure to provide 137.0 mg of the title compound as a white solid (yield: 80%).

$^1$H-NMR spectrum (400 MHz, CD$_2$Cl$_2$) δ: 8.03 (2H, s), 7.68-7.63 (2H, m), 7.42-7.36 (2H, m), 7.22 (1H, d, J=47 Hz), 5.17-5.09 (1H, m), 4.69-4.62 (1H, m), 4.41-4.33 (1H, m), 4.04 (2H, t, J=6 Hz), 3.69-3.59 (1H, m), 3.20 (2H, t, J=8 Hz), 2.91 (3H, s), 2.83-2.56 (4H, m), 2.33-1.56 (17H, m), 1.13 (3H, s), 1.00 (3H, s), 0.65-0.58 (1H, m).

Mass spectrum (EI, m/z): 768 [M$^+$].

To 2 ml of N,N-dimethylformamide deaerated with argon for 10 minutes, 213 mg (1.10 mmol) of 5-bromo-2-chloropyrimidine, 181 mg (1.05 mmol) of 3-(methoxycarbonyl)phenylboronic acid, 315 mg (2.97 mmol) of sodium carbonate and 22.4 mg (0.100 mmol) of palladium acetate were added, and the mixture was stirred at 110° C. for 3 hours. After completion of the reaction, the reaction solution was poured into water and extracted with toluene three times. The obtained organic phases were combined, washed with saturated sodium chloride aqueous solution, dried with magnesium sulfate and then filtered, and the solvent was distilled off under reduced pressure. The obtained residue was subjected to silica gel column chromatography [n-hexane/ethyl acetate=92/8-76/24 (V/V)] and the fraction including the desired compound was concentrated under reduced pressure to provide 74 mg of the title compound as a white solid (yield: 28%).

$^1$H-NMR spectrum (400 MHz, CD$_2$Cl$_2$) δ: 8.87 (2H, s), 8.26 (1H, t, J=2 Hz), 8.14 (1H, dt, J=8, 1 Hz), 7.79 (1H, ddd, J=8, 2, 1 Hz), 7.63 (1H, t, J=8 Hz), 3.90 (3H, s).

Mass spectrum (EI, m/z): 248 [M$^+$].

Reference Example 30

(5S)-2-{1-[5-(3-Carboxyphenyl)pyrimidin-2-yl]piperidin-4-yl}-4-(4,4-difluorocyclohexyl)-3-{(S)-fluoro[4-(trifluoromethyl)phenyl]methyl}-7,7-dimethyl-5,6,7,8-tetrahydroquinolin-5-ol

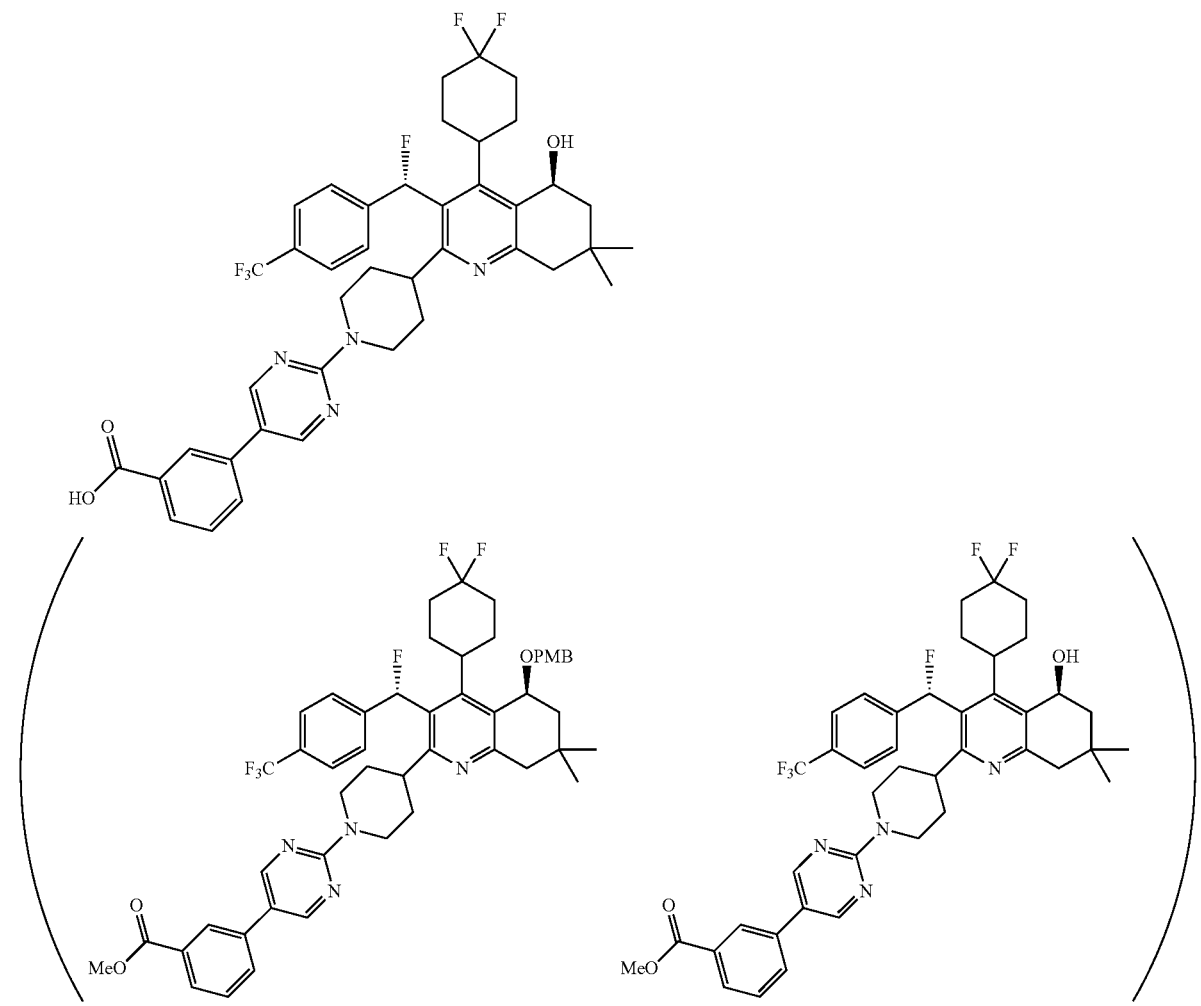

To a solution of 50.0 mg (0.0741 mmol) of (−)-(5S)-4-(4,4-Difluorocyclohexyl)-3-{(S)-fluoro[4-(trifluoromethyl)phenyl]methyl}-5-[(4-methoxybenzyl)oxy]-7,7-dimethyl-2-(piperidin-4-yl)-5,6,7,8-tetrahydroquinoline, which was prepared by a method similar to that of Reference Example 10, in 0.2 ml of 1,4-dioxane, 38.2 mg (0.154 mmol) of methyl 3-(2-chloropyrimidin-5-yl)benzoate, which was prepared by a method similar to that of Reference Example 29, and 20.0 mg (0.144 mmol) of potassium carbonate were added, and the mixture was stirred at 120° C. for 21 hours. After completion of the reaction, water was added to the reaction solution and the reaction solution was extracted with ethyl acetate. The obtained organic phases were combined and washed with saturated sodium chloride aqueous solution, and then the solvent was distilled off under reduced pressure. The obtained residue was subjected to silica gel column chromatography [n-hexane/ethyl acetate=96/4-76/24 (V/V)] and the fraction including the desired compound was concentrated under reduced pressure to provide 85.4 mg of (5S)-4-(4,4-Difluorocyclohexyl)-3-{fluoro[4-(trifluoromethyl)phenyl]methyl}-5-[(4-methoxybenzyl)oxy]-2-(1-{5-[3-(methoxycarbonyl)phenyl]pyrimidin-2-yl}piperidin-4-yl)-7,7-dimethyl-5,6,7,8-tetrahydroquinoline as a mixture with methyl 3-(2-chloropyrimidin-5-yl)benzoate. To a solution of 83.0 mg of this mixture in 1 ml of 1,4-dioxane, 1 ml of 2 N hydrochloric acid was added, and the mixture was stirred at 80° C. for 4.5 hours. After completion of the reaction, the reaction solution was poured into saturated sodium hydrogencarbonate aqueous solution and extracted with ethyl acetate. The obtained organic phases were combined and washed with saturated sodium chloride aqueous solution, and then the solvent was distilled off under reduced pressure. The obtained residue was subjected to silica gel column chromatography [n-hexane/ethyl acetate=78/22-40/60 (V/V)] and the fraction including the desired compound was concentrated under reduced pressure to provide 11.9 mg of the title compound (yield: 21%) and 28.5 mg of (5S)-4-(4,4-Difluorocyclohexyl)-3-{fluoro[4-(trifluoromethyl)phenyl]methyl}-2-(1-{5-[3-(methoxycarbonyl)phenyl]pyrimidin-2-yl}piperidin-4-yl)-7,7-dimethyl-5,6,7,8-tetrahydroquinolin-5-ol (yield: 50%) as a white solid.

A reaction similar to that described above was performed to provide 10.8 mg of the title compound (yield: 19%) and 32.2 mg of (5S)-4-(4,4-Difluorocyclohexyl)-3-{fluoro[4-(trifluoromethyl)phenyl]methyl}-2-(1-{5-[3-(methoxycarbonyl)phenyl]pyrimidin-2-yl}piperidin-4-yl)-7,7-dimethyl-5,6,7,8-tetrahydroquinolin-5-ol (yield: 57%) as a white solid.

58.1 mg (total: 0.0758 mmol) of (5S)-4-(4,4-Difluorocyclohexyl)-3-{fluoro[4-(trifluoromethyl)phenyl]methyl}-2-(1-{5-[3-(methoxycarbonyl)phenyl]pyrimidin-2-yl}piperidin-4-yl)-7,7-dimethyl-5,6,7,8-tetrahydroquinolin-5-ol obtained by the above-described two reactions was dissolved in 0.4 ml of 1,4-dioxane, then 0.1 ml of methanol and 0.1 ml of 5 N sodium hydroxide aqueous solution were added thereto, and the mixture was stirred for 6 hours and 20 minutes. After completion of the reaction, 0.25 ml of 2 N hydrochloric acid was added to the reaction solution and the reaction solution was extracted with ethyl acetate. The obtained organic phases were combined and washed with saturated sodium chloride aqueous solution, and then the solvent was distilled off under reduced pressure. The obtained residue was subjected to silica gel column chromatography [n-hexane/ethyl acetate=65/35-25/75 (V/V)] and the fraction including the desired compound was concentrated under reduced pressure to provide 54.2 mg of the title compound as a white solid (yield: 95%).

$^1$H-NMR spectrum (400 MHz, $CD_2Cl_2$) δ: 8.41 (2H, s), 8.03-7.99 (1H, m), 7.95-7.89 (1H, m), 7.72-7.65 (2H, m), 7.48-7.38 (4H, m), 7.27 (1H, d, J=47 Hz), 5.18-5.11 (1H, m), 4.91-4.83 (1H, m), 4.61-4.52 (1H, m), 3.72-3.62 (1H, m), 3.03-2.63 (4H, m), 2.36-1.68 (15H, m), 1.10 (3H, s), 0.97 (3H, s), 0.69-0.60 (1H, m).

Mass spectrum (EI, m/z): 752 [M$^+$].

Figure 2:
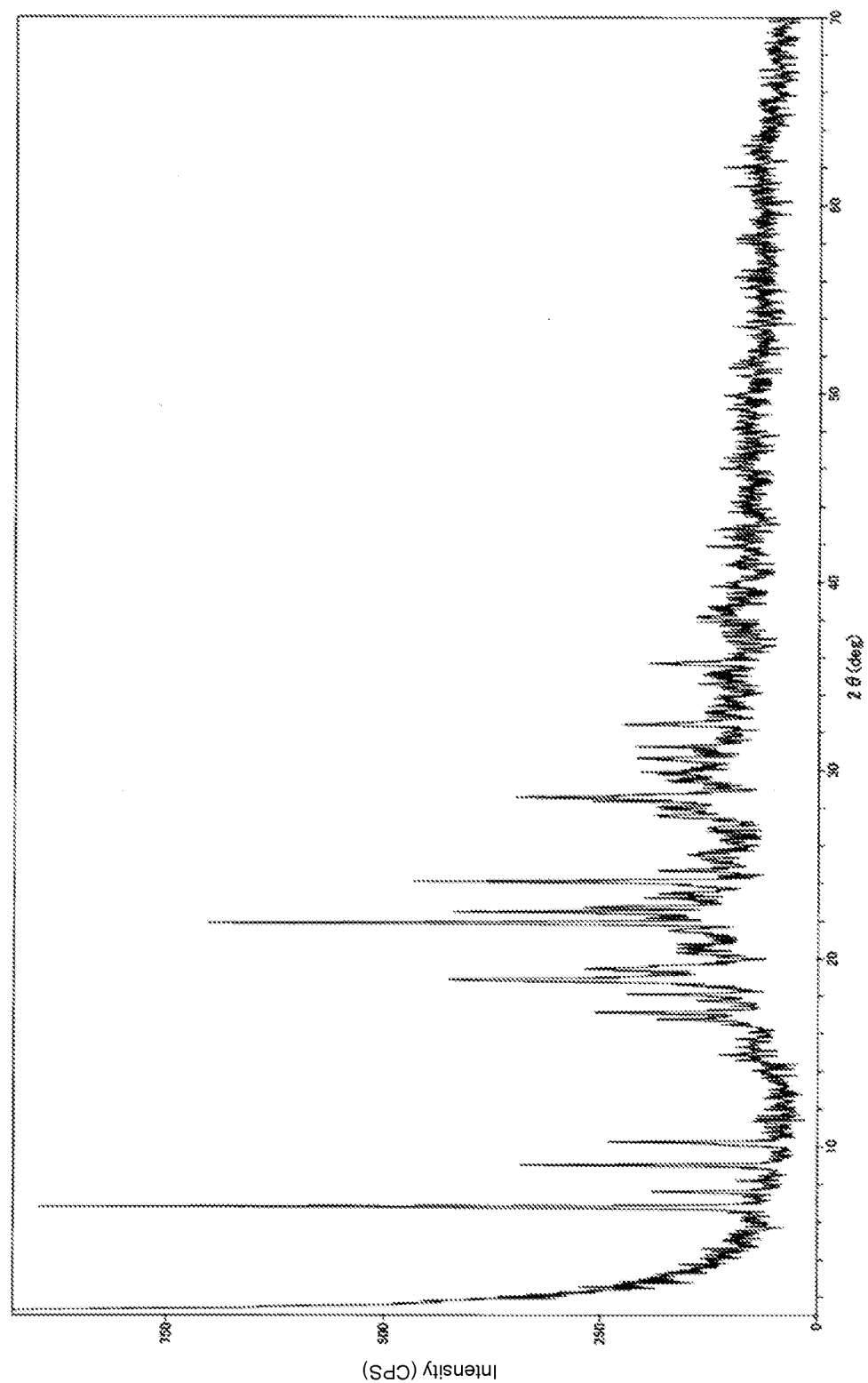
FIG. 2 shows an X-ray diffraction pattern exhibited by a crystal of a salt of a compound obtained in Example 2.
Figure 3:
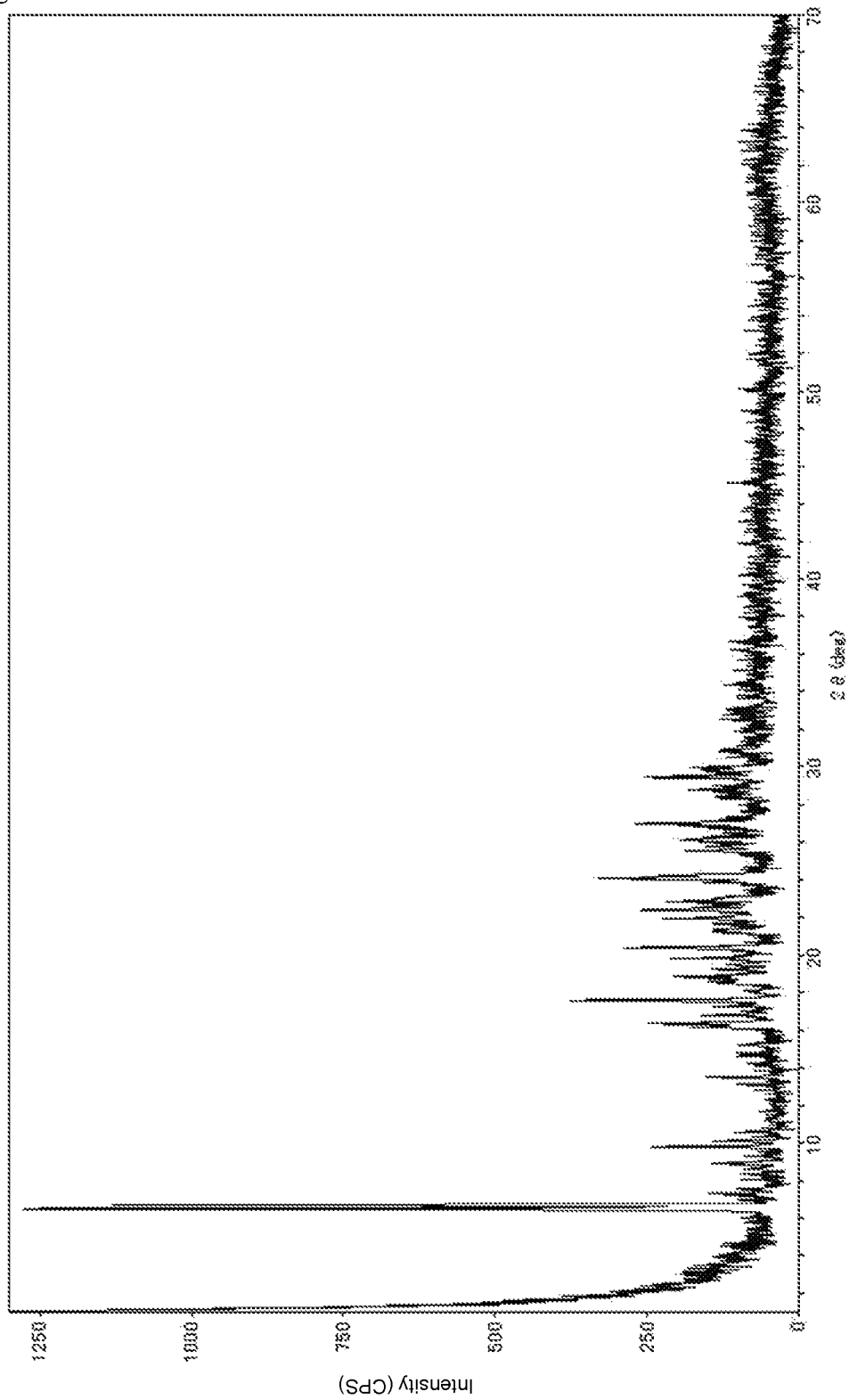
FIG. 3 shows an X-ray diffraction pattern exhibited by a crystal of a salt of a compound obtained in Example 3.
Figure 4:
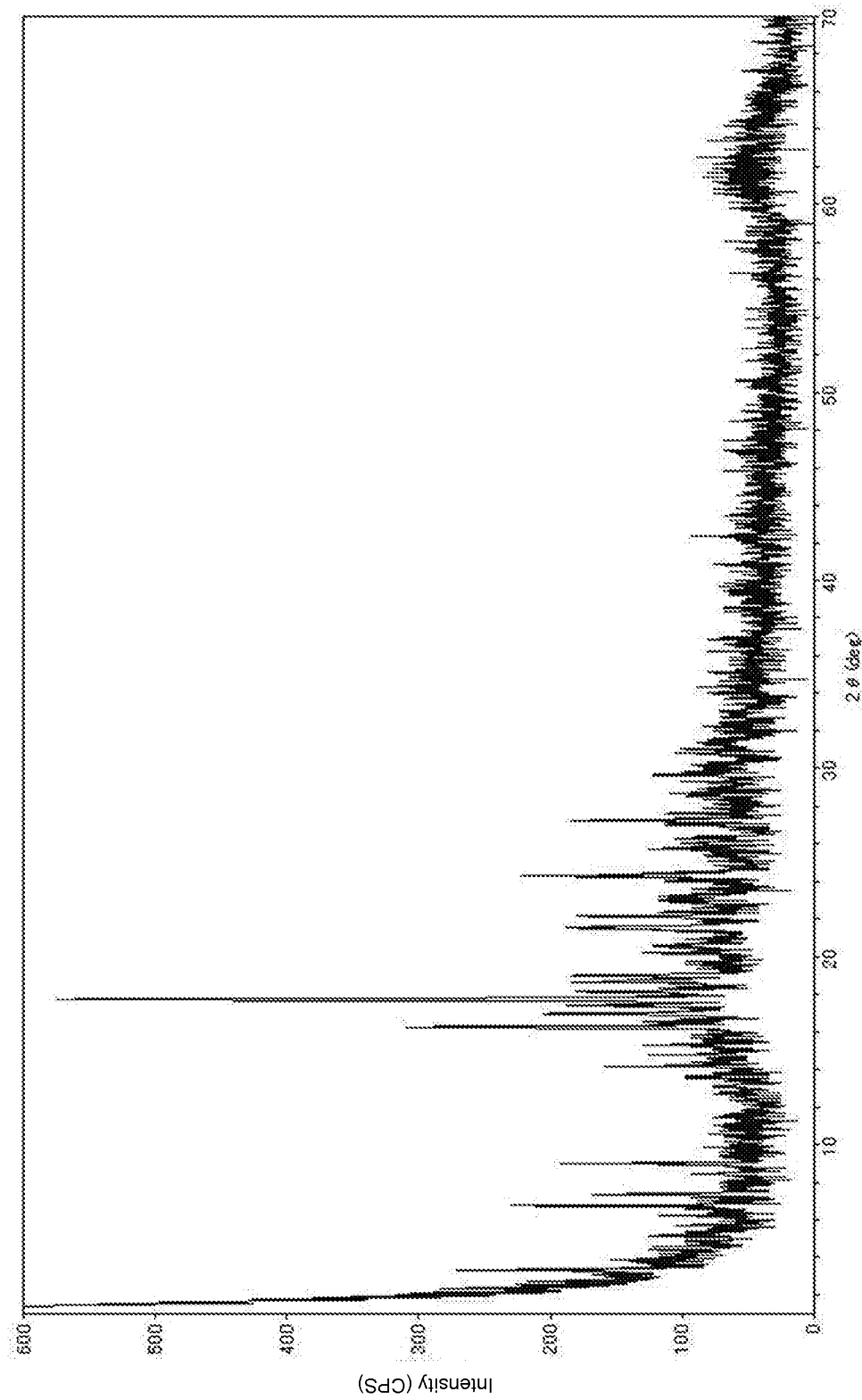
FIG. 4 shows an X-ray diffraction pattern exhibited by a crystal of a salt of a compound obtained in Example 4.
Figure 5:
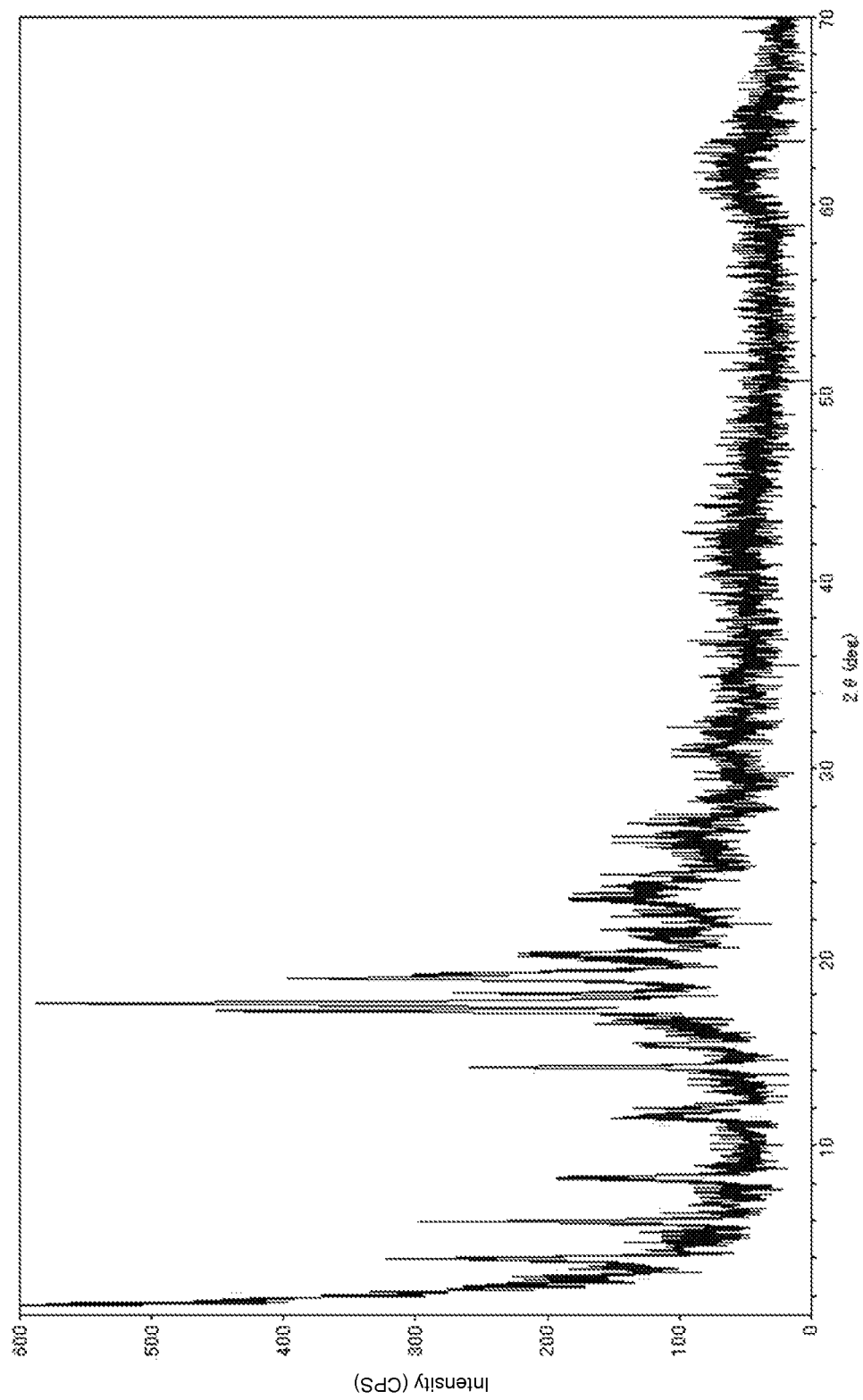
FIG. 5 shows an X-ray diffraction pattern exhibited by a crystal of a salt of a compound obtained in Example 5.
Figure 6:
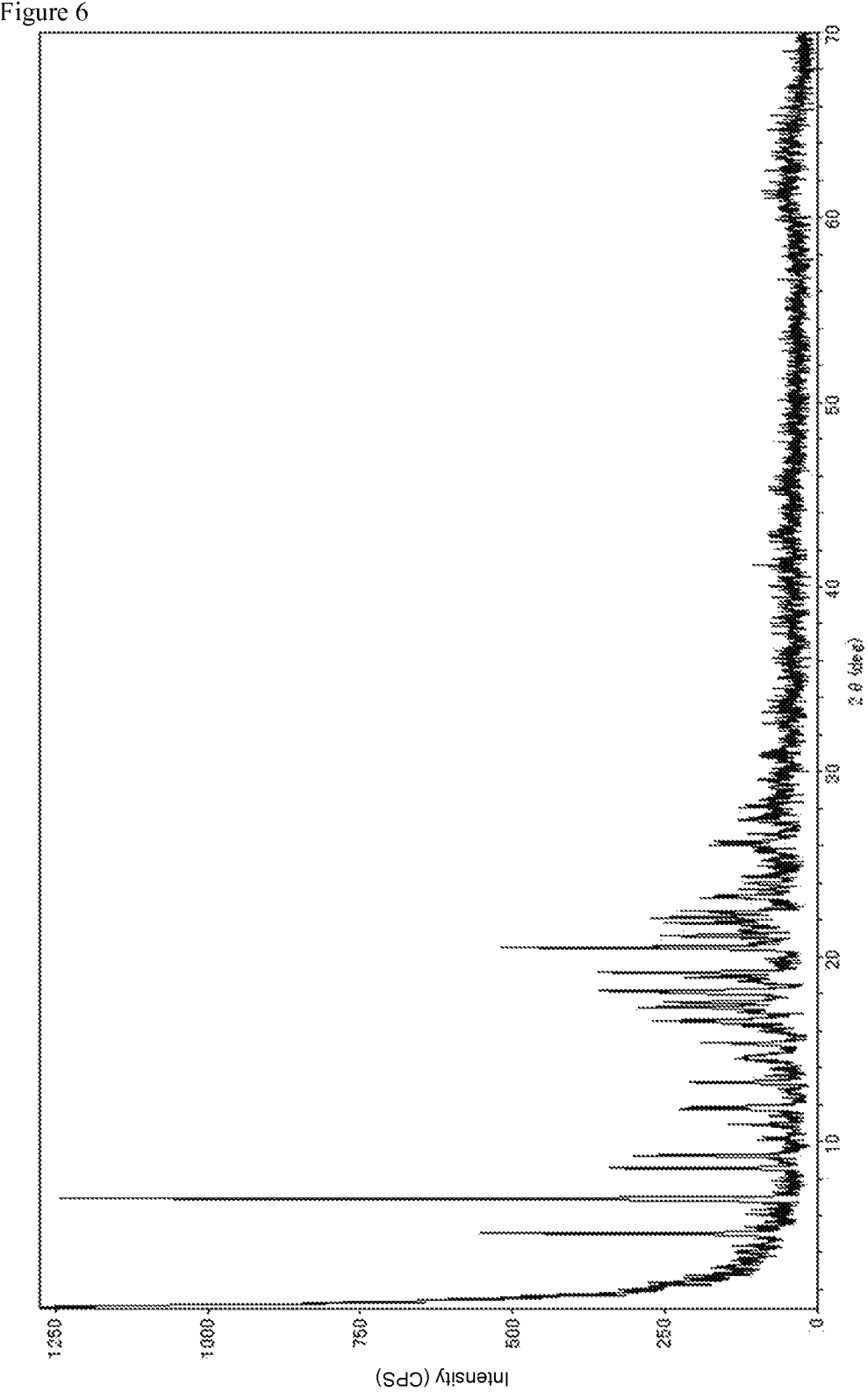
FIG. 6 shows an X-ray diffraction pattern exhibited by a crystal of a salt of a compound obtained in Example 6.
Figure 7:
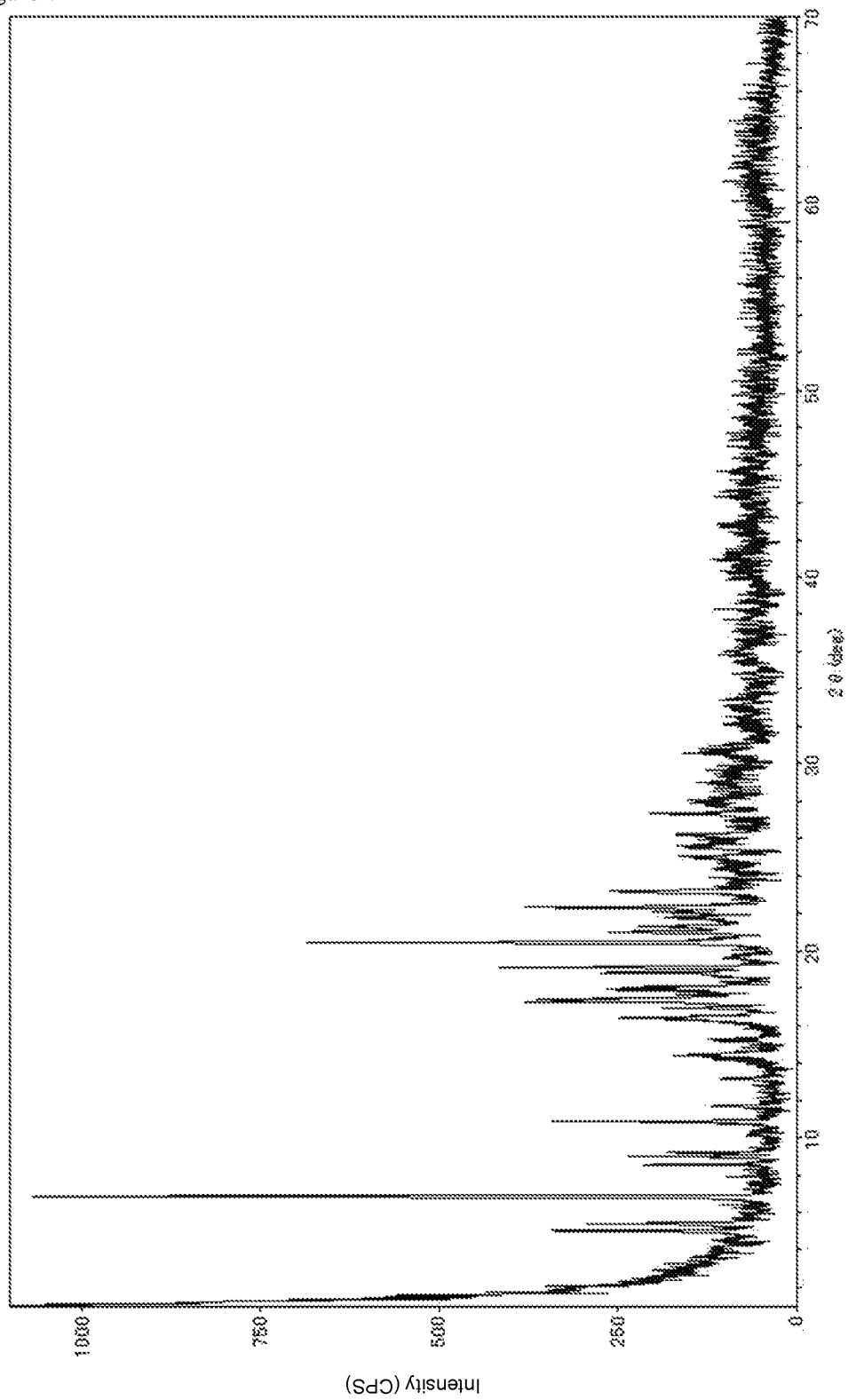
FIG. 7 shows an X-ray diffraction pattern exhibited by a crystal of a salt of a compound obtained in Example 7.
Figure 8:
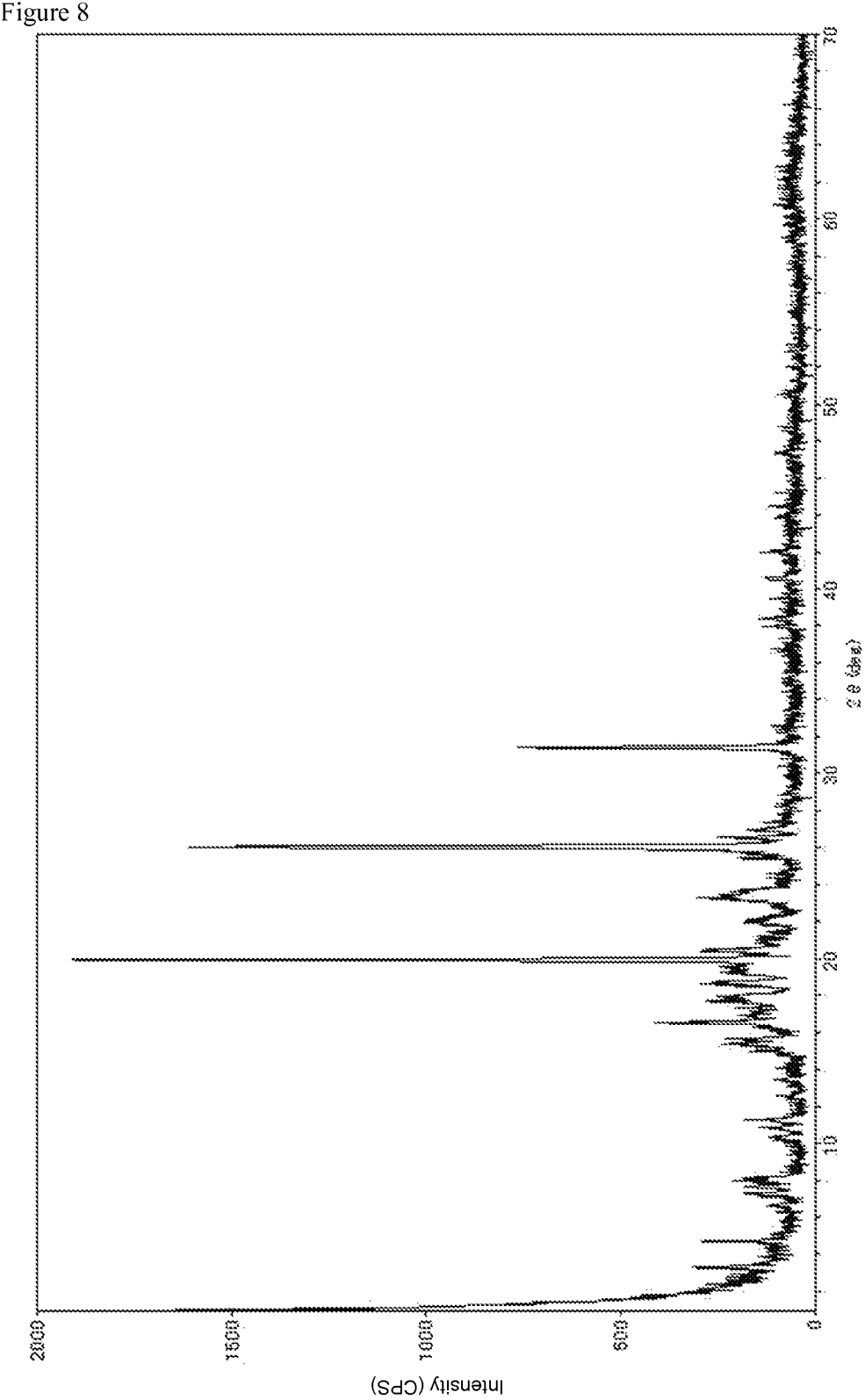
FIG. 8 shows an X-ray diffraction pattern exhibited by a crystal of a salt of a compound obtained in Example 8.
Figure 9:
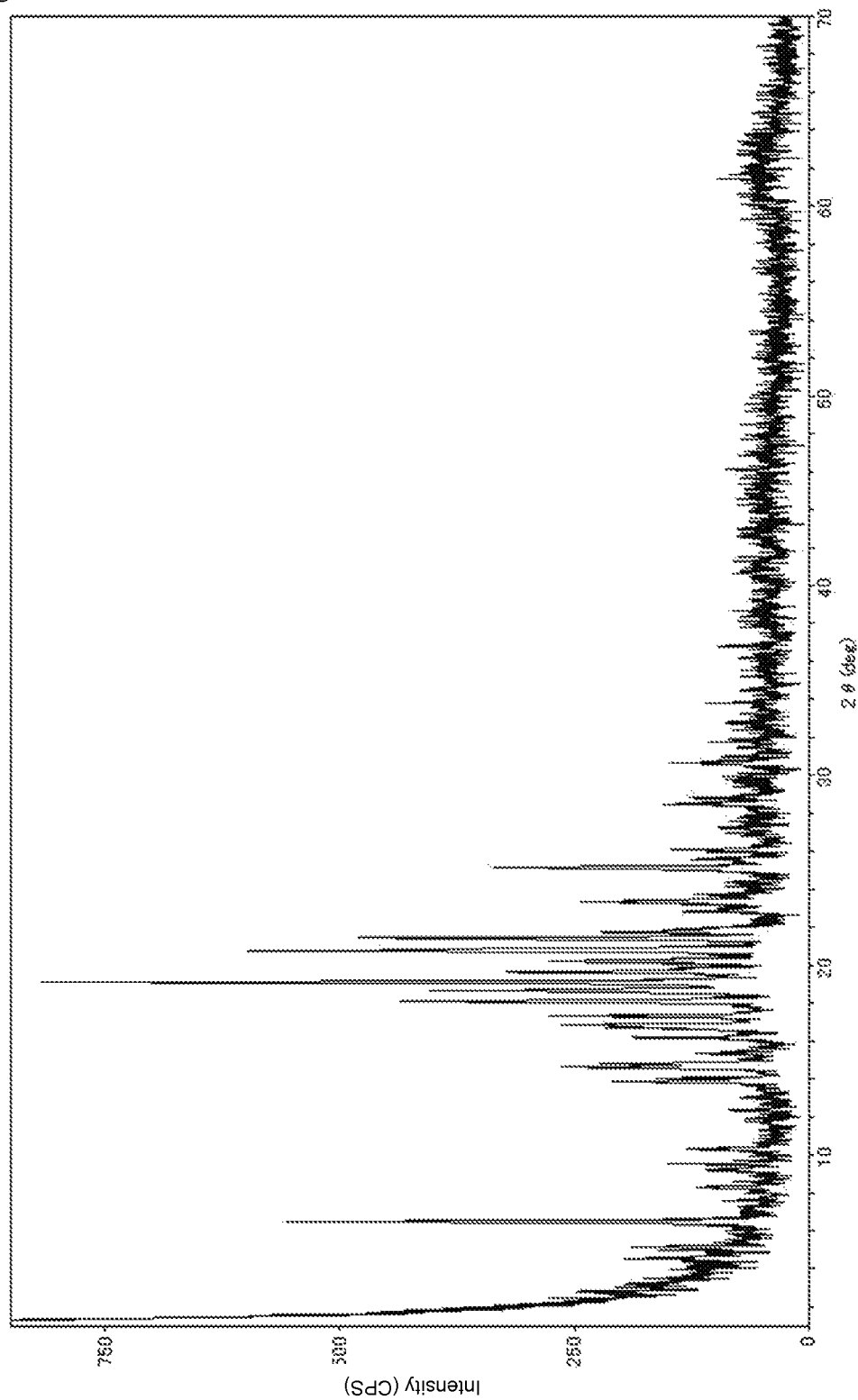
FIG. 9 shows an X-ray diffraction pattern exhibited by a crystal of a salt of a compound obtained in Example 9.
Figure 10:
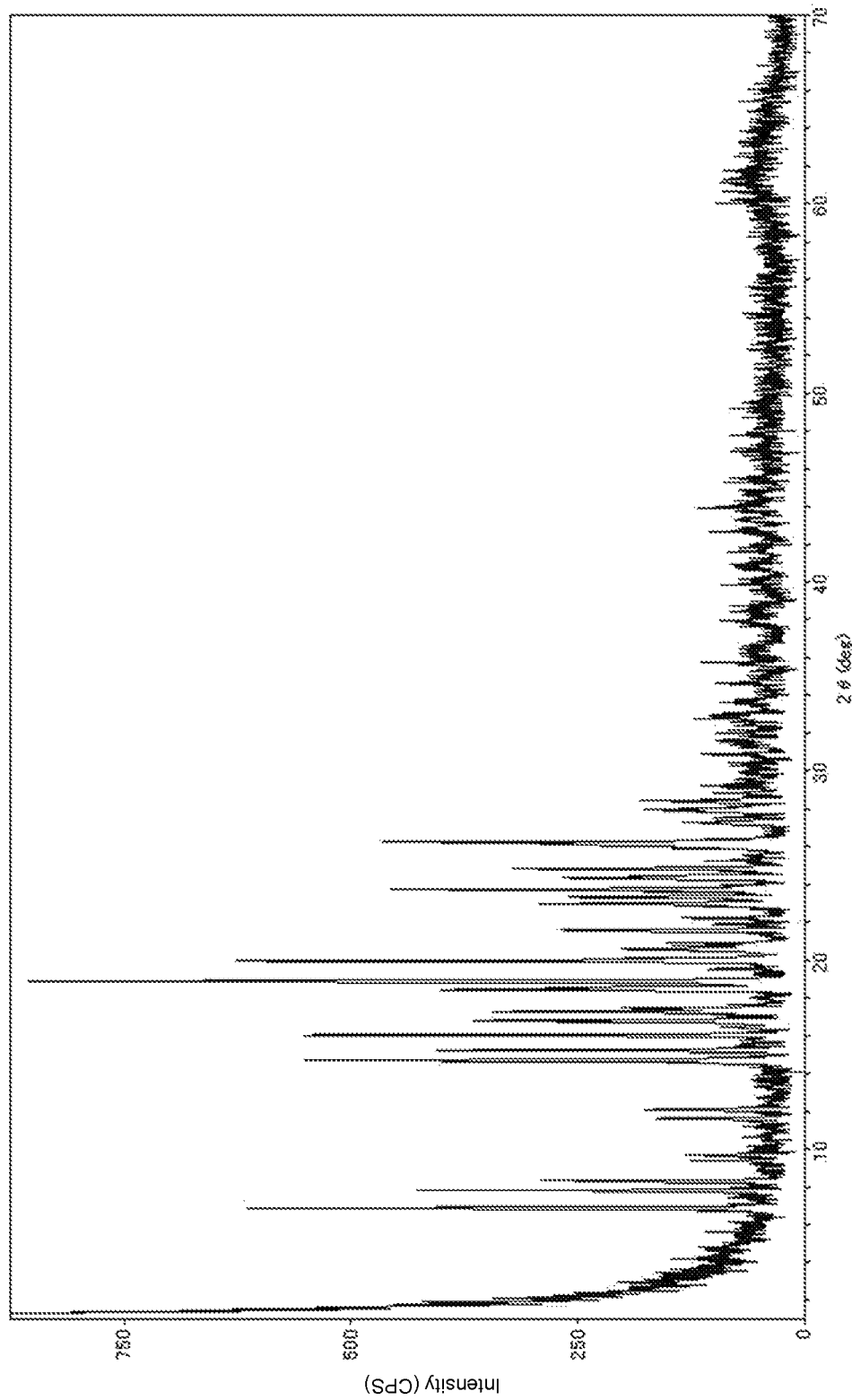
FIG. 10 shows an X-ray diffraction pattern exhibited by a crystal of a salt of a compound obtained in Example 10.
Figure 11:
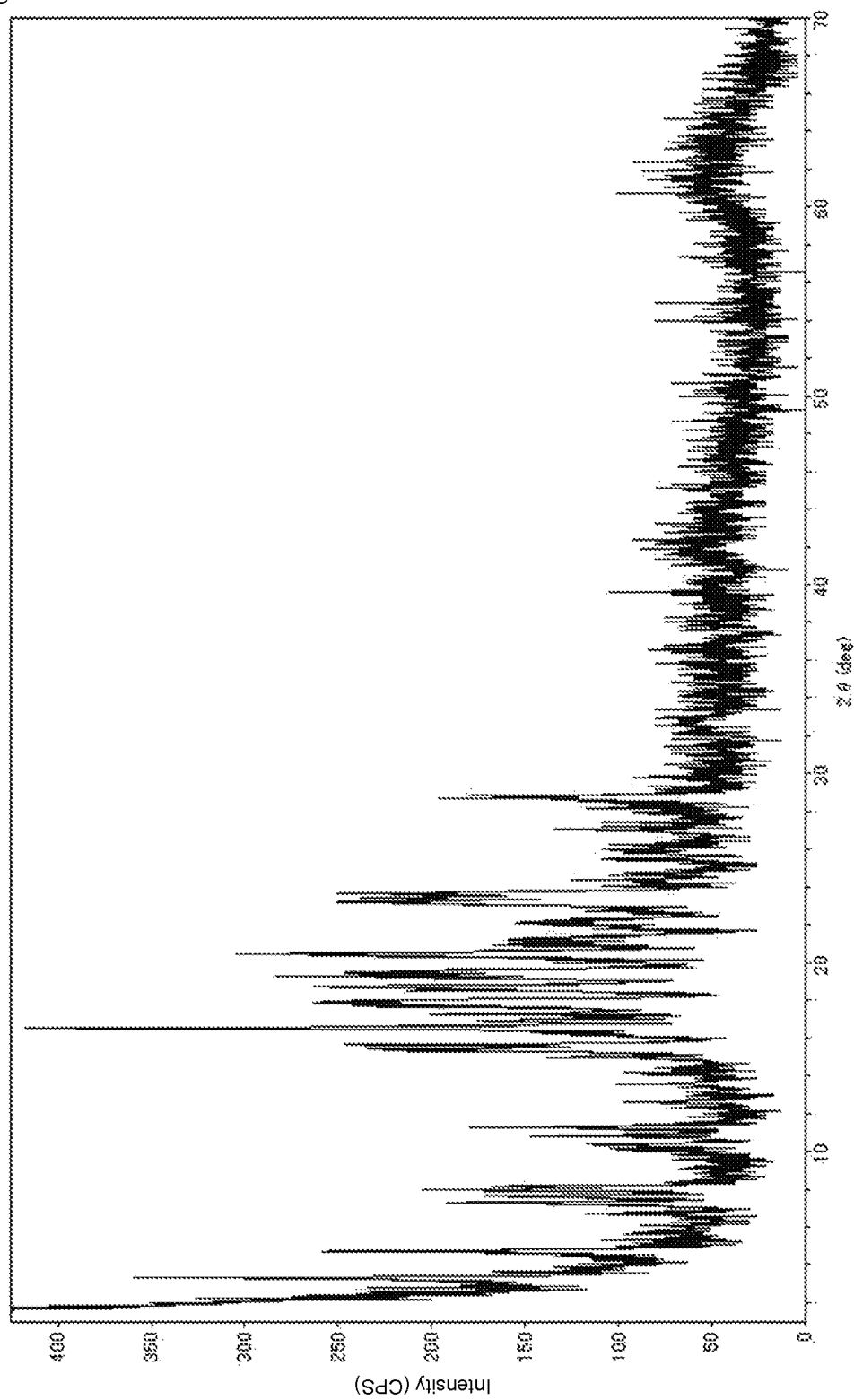
FIG. 11 shows an X-ray diffraction pattern exhibited by a crystal of a salt of a compound obtained in Example 11.
Figure 12:
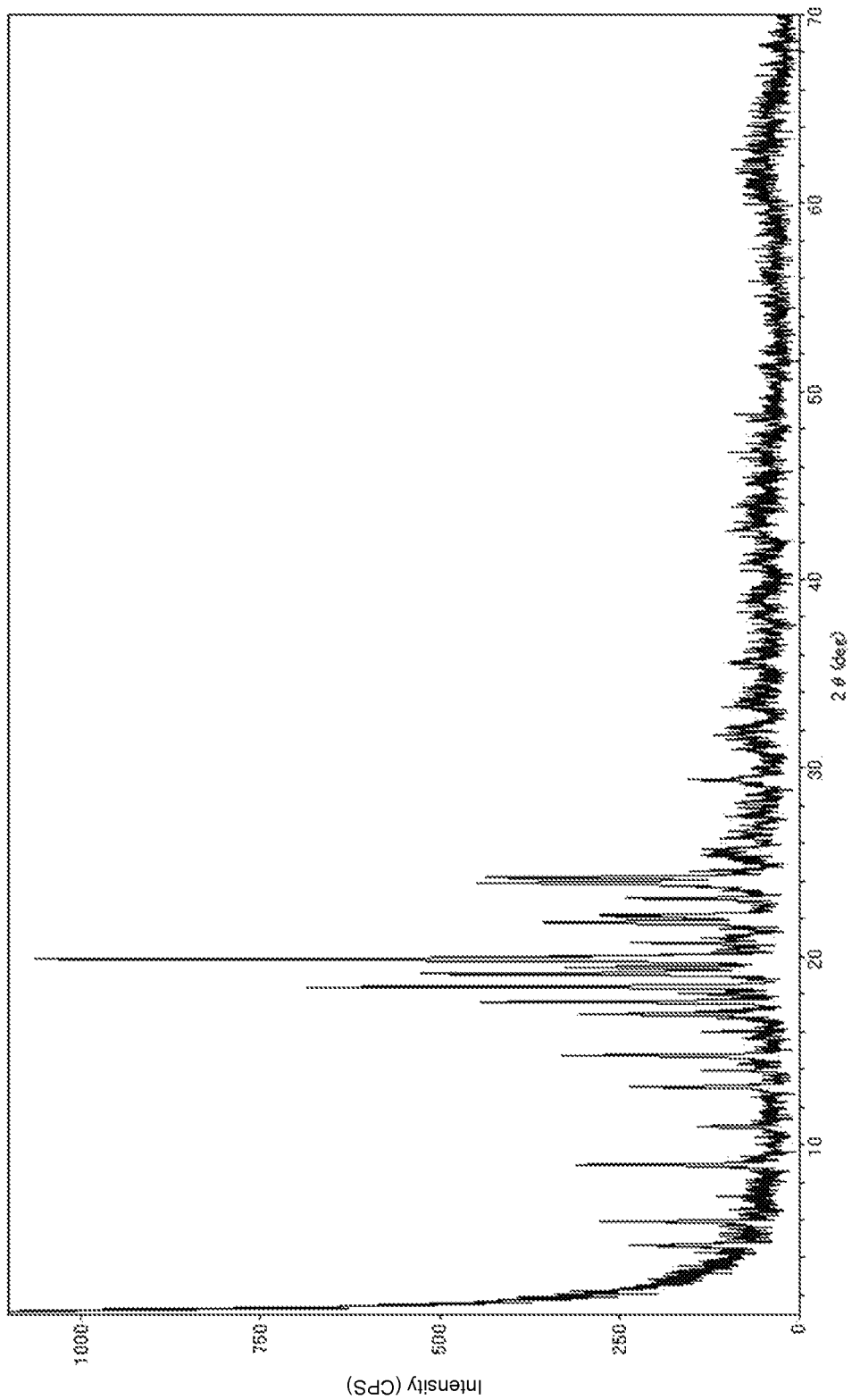
FIG. 12 shows an X-ray diffraction pattern exhibited by a crystal of a salt of a compound obtained in Example 12.
Figure 13:
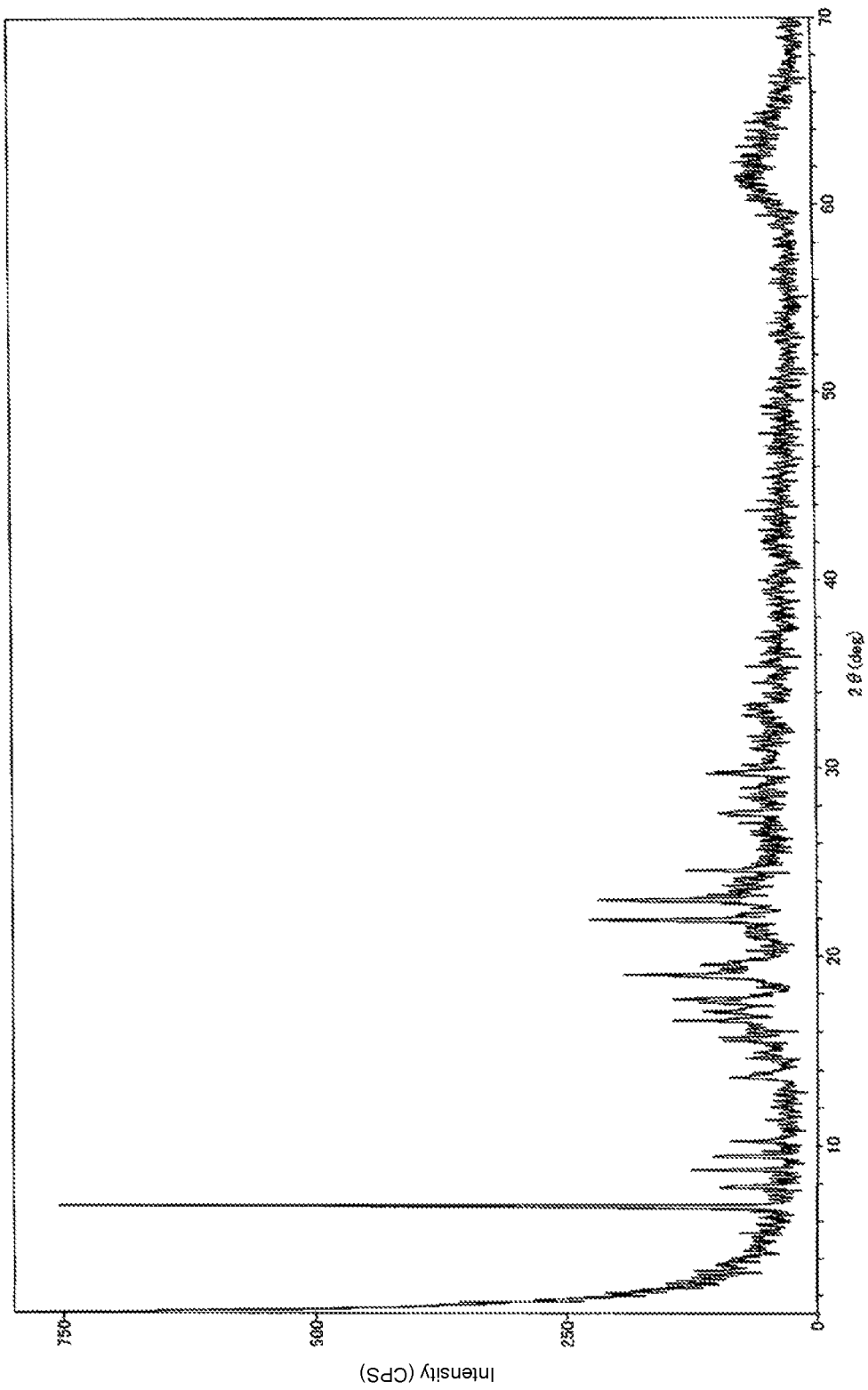
FIG. 13 shows an X-ray diffraction pattern exhibited by a crystal of a salt of a compound obtained in Example 13.
Figure 14:
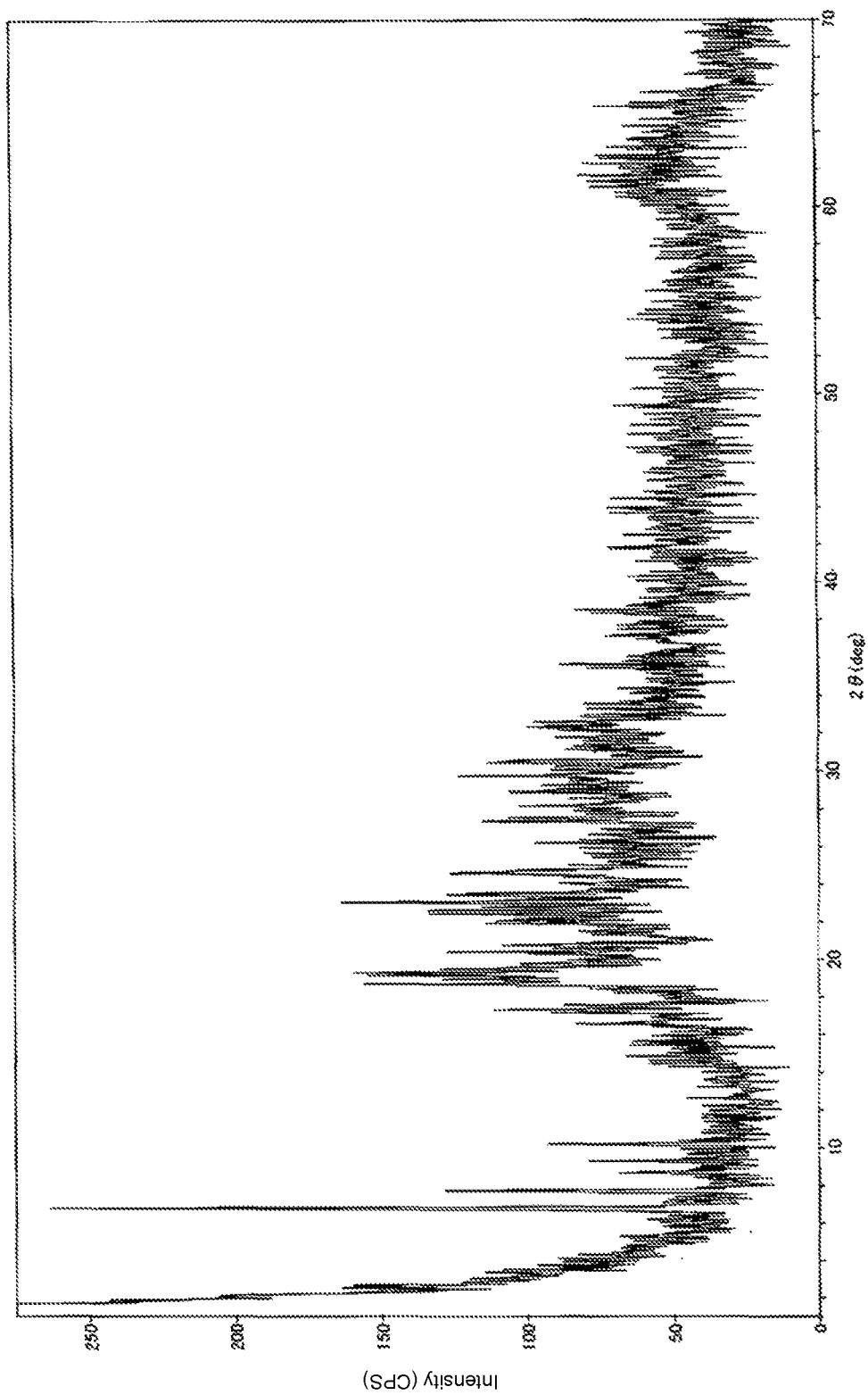
FIG. 14 shows an X-ray diffraction pattern exhibited by a crystal of a salt of a compound obtained in Example 14.
Figure 15:
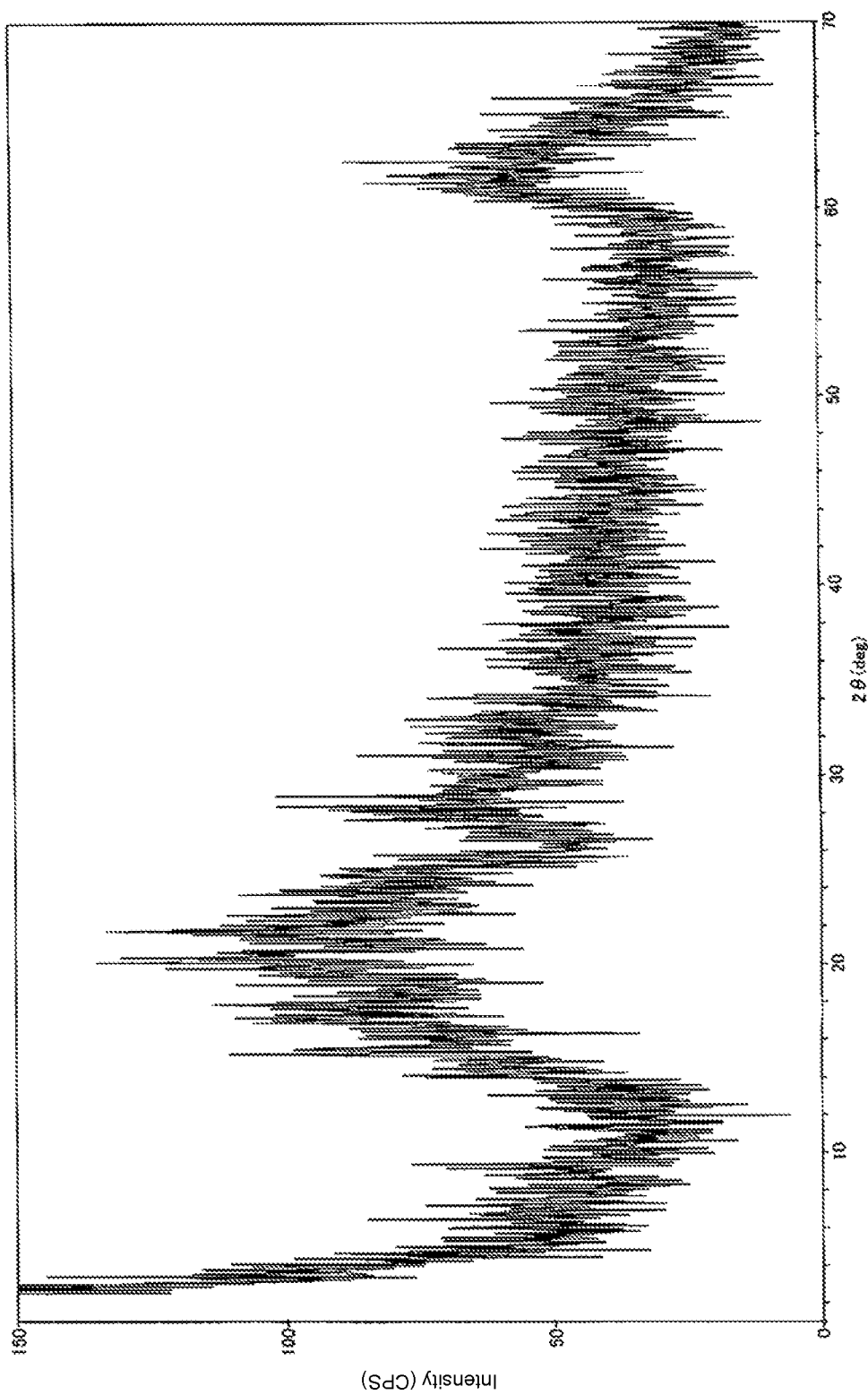
FIG. 15 shows an X-ray diffraction pattern exhibited by a crystal of a salt of a compound obtained in Example 15.
Figure 16:
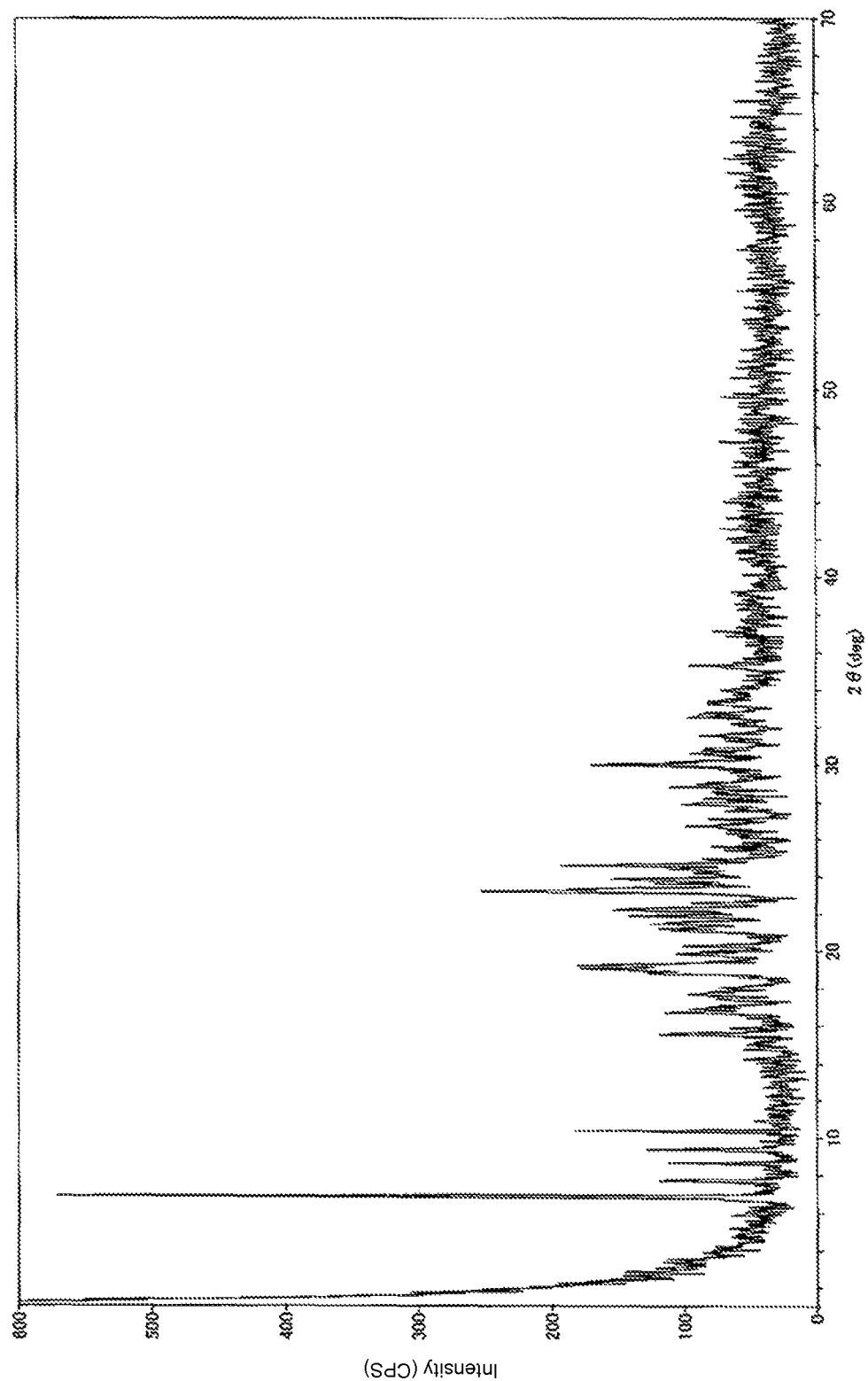
FIG. 16 shows an X-ray diffraction pattern exhibited by a crystal of a salt of a compound obtained in Example 16.
Figure 17:
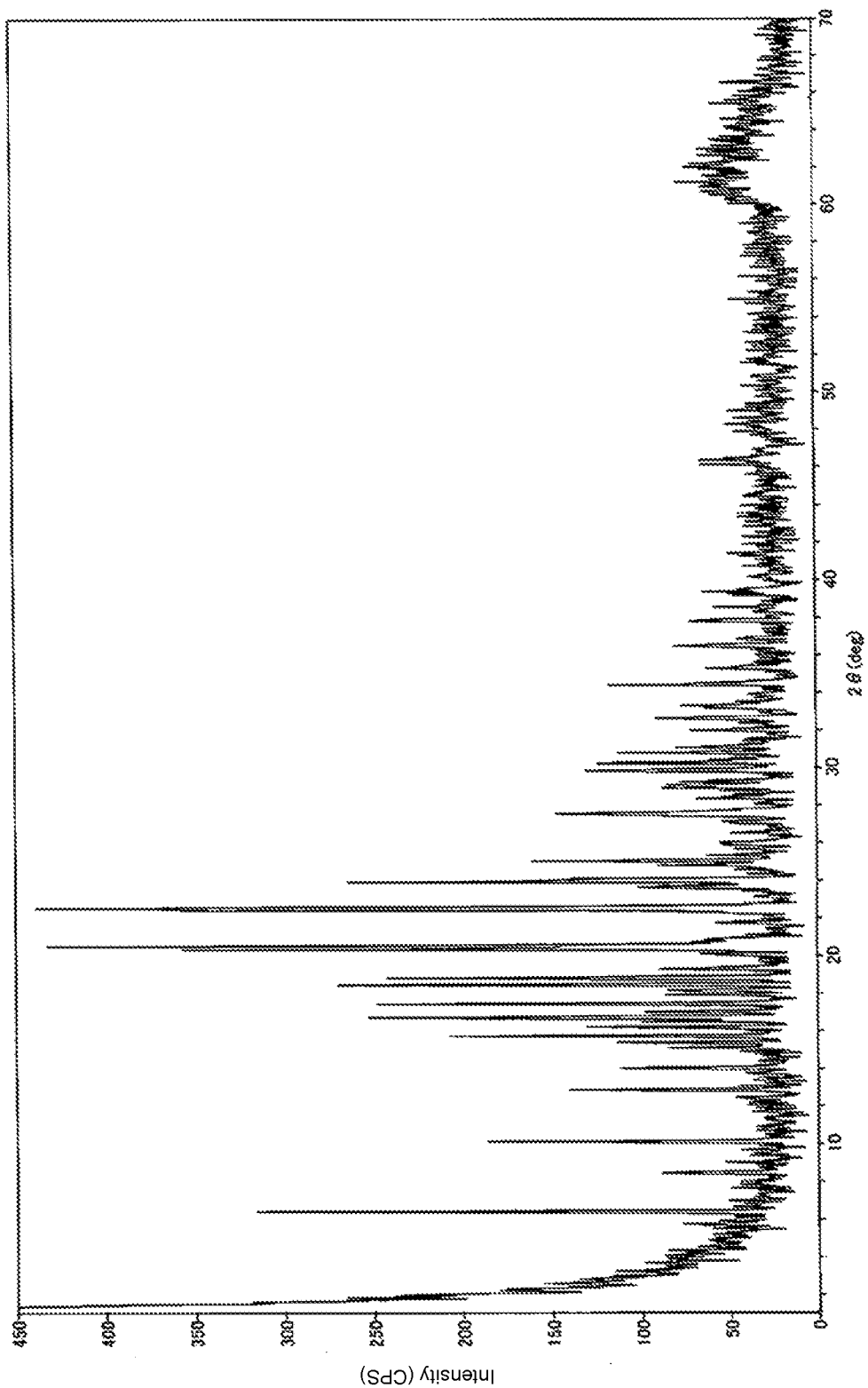
FIG. 17 shows an X-ray diffraction pattern exhibited by a crystal of a salt of a compound obtained in Example 17.
Figure 18:
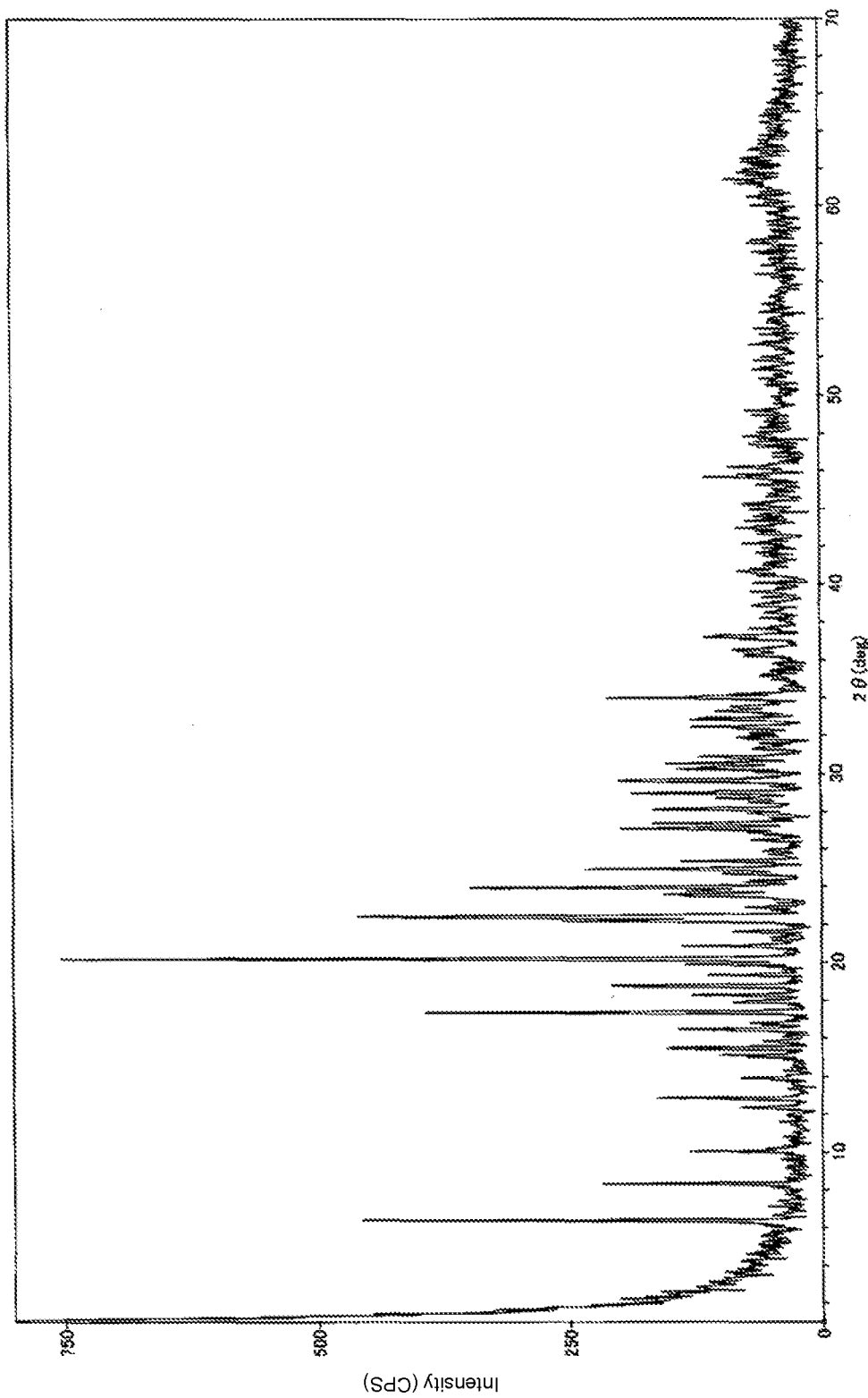
FIG. 18 shows an X-ray diffraction pattern exhibited by a crystal of a salt of a compound obtained in Example 18.
Figure 19:
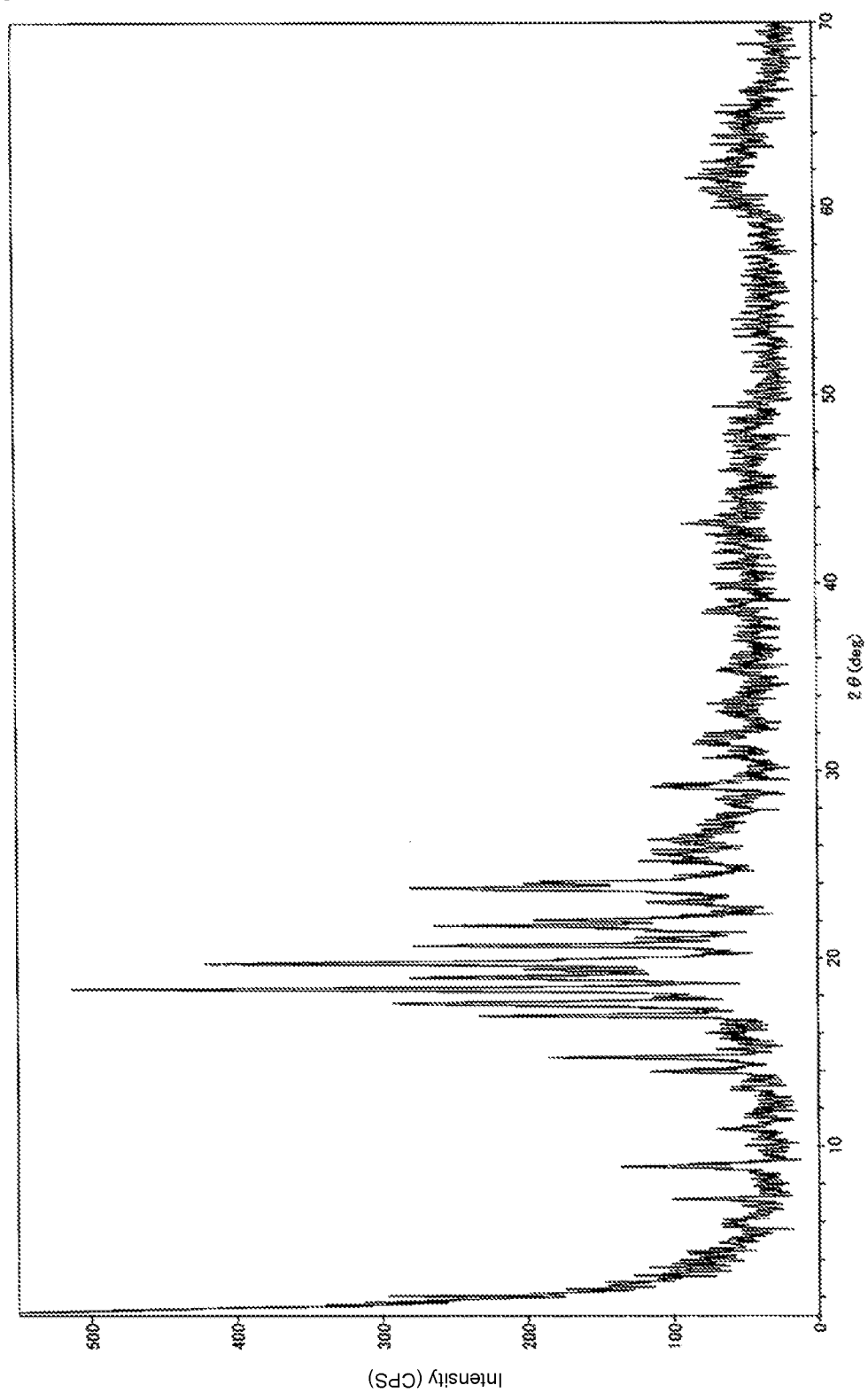
FIG. 19 shows an X-ray diffraction pattern exhibited by a crystal of a salt of a compound obtained in Example 19.
Figure 20:
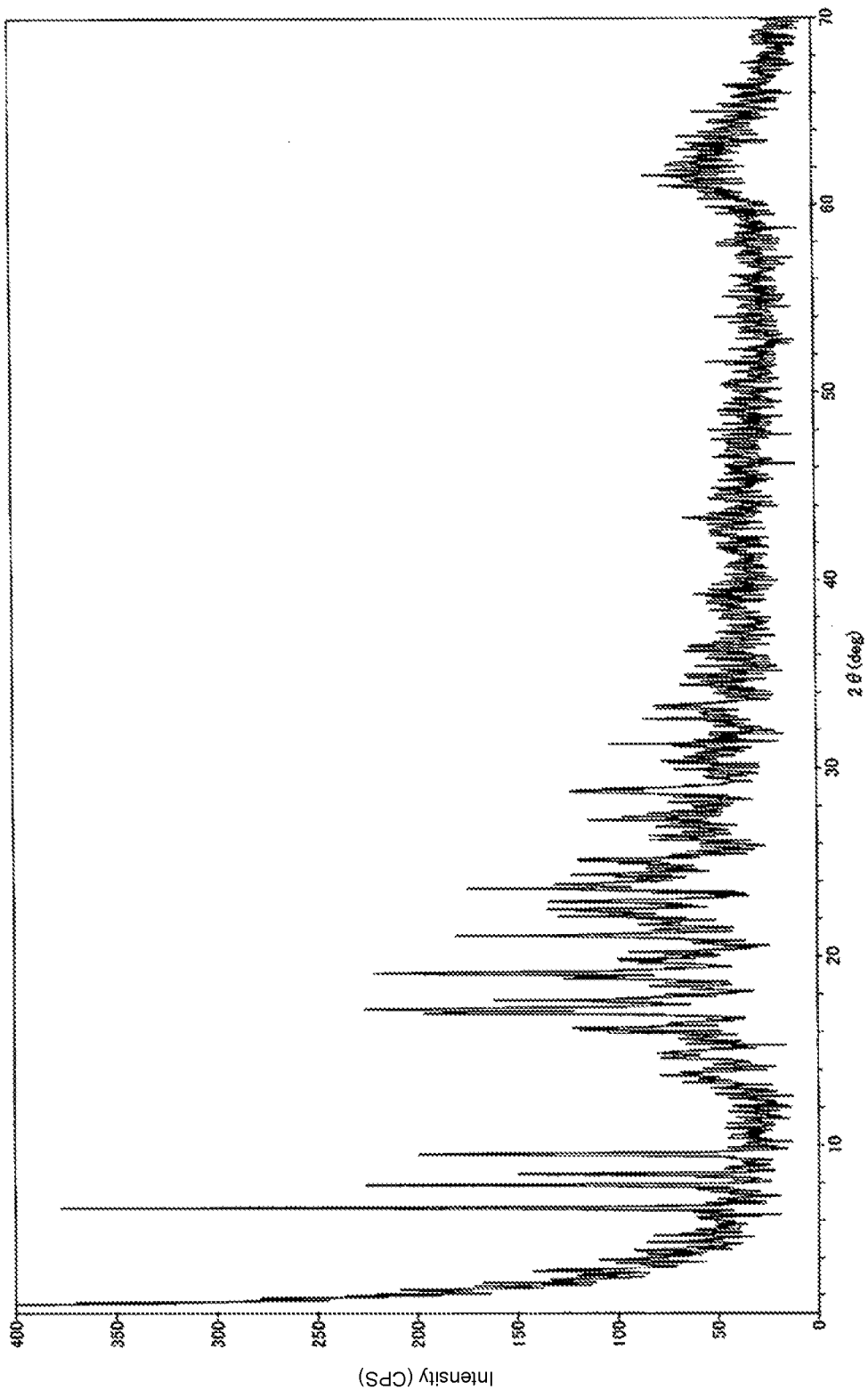
FIG. 20 shows an X-ray diffraction pattern exhibited by a crystal of a salt of a compound obtained in Example 20.
Figure 21:
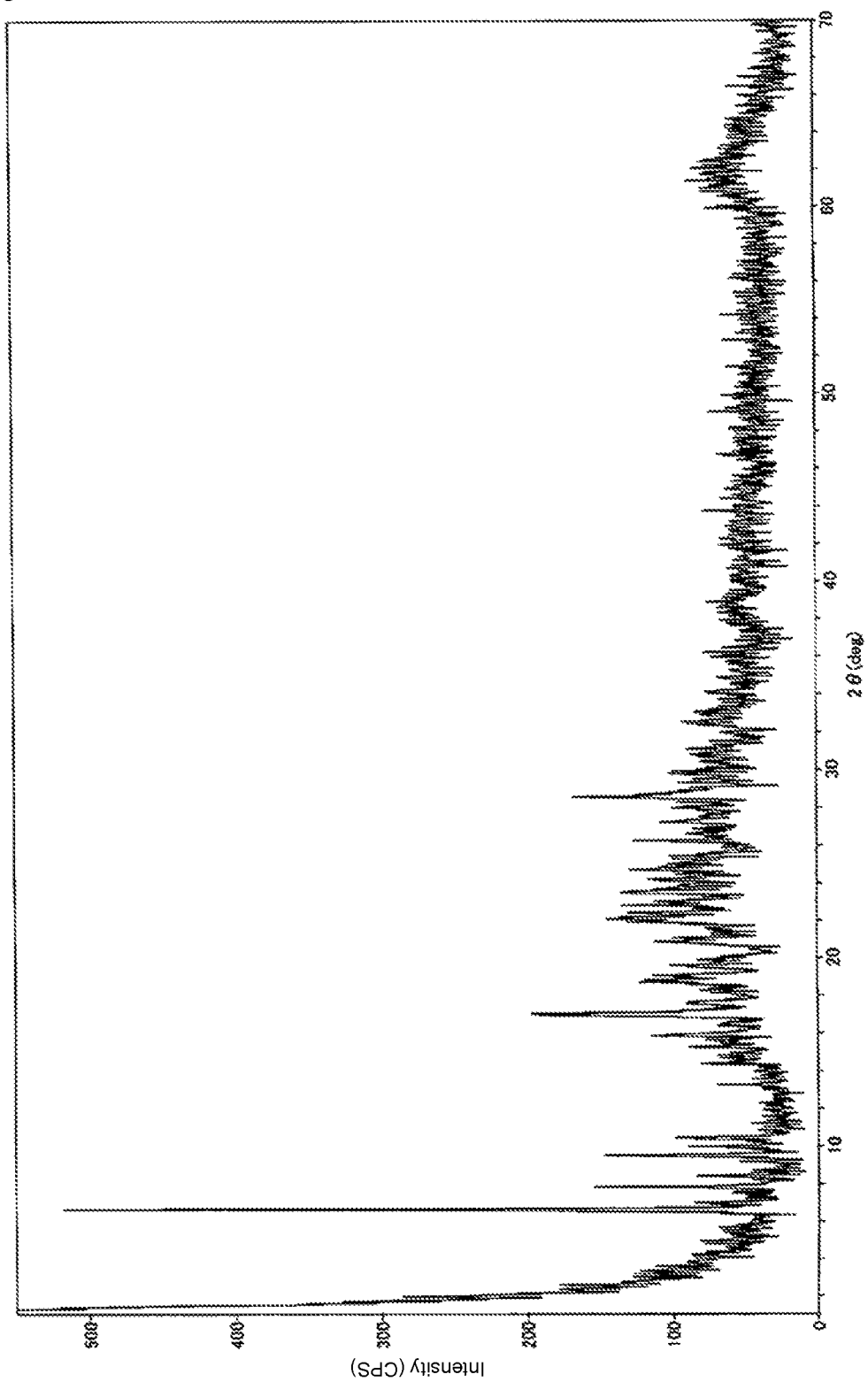
FIG. 21 shows an X-ray diffraction pattern exhibited by a crystal of a salt of a compound obtained in Example 21.

The salts of the compounds obtained in Examples 1 to 21 were obtained as crystals exhibiting the powder X-ray diffraction patterns shown in FIGS. 1 to 21, respectively. The spacing d corresponding to main peaks in each pattern are as shown in Table 1. The spacing d (A) are calculated from the diffraction angle 2θ (degrees) shown in the abscissa of each pattern according to the following expression:

2d sin θ=nλ, wherein n=1

λ, (Kα rays)=1.54 (Å)

λ, (Kα1 rays)=1.541 (Å)

The crystal of the salt of the compound of each Example is preferred which has main peaks corresponding to the spacing d shown in Table 1 in a powder X-ray diffraction pattern obtained by copper Kα radiation.

TABLE 1

| Example | FIG. | Spacing d (Å) corresponding to main peaks |
|---|---|---|
| 1 | 1 | 12.8, 9.7, 5.1, 4.9, 4.0, 3.7, 3.1 (±0.2) |
| 2 | 2 | 13.0, 9.8, 8.6, 4.7, 4.1, 3.7, 3.1 (±0.2) |
| 3 | 3 | 13.4, 13.0, 9.0, 5.0, 3.7, 3.3, 3.0 (±0.2) |
| 4 | 4 | 12.9, 9.8, 5.4, 5.0, 4.1, 4.0, 3.7, 3.3 (±0.2) |
| 5 | 5 | 14.8, 10.6, 6.2, 5.2, 5.0, 4.7, 4.4 (±0.2) |
| 6 | 6 | 17.3, 12.6, 10.2, 9.5, 5.1, 4.9, 4.6, 4.3 (±0.2) |
| 7 | 7 | 12.7, 8.1, 5.1, 4.6, 4.3, 4.0, 3.8 (±0.2) |
| 8 | 8 | 5.3, 4.4, 3.8, 3.4, 2.8 (±0.2) |
| 9 | 9 | 13.5, 5.2, 4.6, 4.3, 4.1, 3.5 (±0.2) |
| 10 | 10 | 12.7, 11.2, 6.0, 5.5, 4.7, 4.4, 3.7, 3.4 (±0.2) |
| 11 | 11 | 8.1, 7.8, 5.6, 5.3, 4.9, 4.7, 4.6, 4.3, 3.1 (±0.2) |
| 12 | 12 | 5.0, 4.8, 4.6, 4.5, 4.1, 3.7 (±0.2) |
| 13 | 13 | 13.0, 8.6, 6.5, 5.0, 4.7, 4.1, 3.9, 3.6, 3.2, 3.0 (±0.2) |

TABLE 1-continued

| Example | FIG. | Spacing d (Å) corresponding to main peaks |
|---|---|---|
| 14 | 14 | 13.0, 11.4, 8.6, 4.7, 4.6, 3.9, 3.6 (±0.2) |
| 15 | 15 | 5.8, 4.4, 4.1, 3.1 (±0.2) |
| 16 | 16 | 12.8, 9.4, 8.5, 5.7, 4.7, 4.6, 3.8, 3.6, 3.0 (±0.2) |
| 17 | 17 | 13.8, 8.7, 6.9, 4.8, 4.4, 4.3, 3.9, 3.7, 3.2 (±0.2) |
| 18 | 18 | 13.8, 10.6, 5.1, 4.4, 4.0, 3.7, 2.6 (±0.2) |
| 19 | 19 | 9.9, 6.0, 5.0, 4.8, 4.5, 4.3, 4.1, 3.7 (±0.2) |
| 20 | 20 | 13.2, 11.2, 9.3, 5.2, 5.0, 4.6, 4.2, 3.8, 3.1 (±0.2) |
| 21 | 21 | 13.3, 11.2, 9.3, 5.2, 4.7, 4.0, 3.1 (±0.2) |

Each of the salts of the compounds shown in the above-described (b-1) to (b-7), which are encompassed in the salt of the compound represented by general formula (I) or (I-1) of the present invention, may be prepared according to methods similar to those of the Examples and Reference Examples above.

Test Example 1

Test of CETP Inhibition Activity (In Vitro, Buffer-Based)

(1) Preparation of Reconstituted HDL

Cholesterol (1.125 μmol), phosphatidyl choline (4.5 μmol) and [$^{14}$C]-labeled cholesteryl ester (2.0 μCi; 40 μl) were taken in a glass test tube and well mixed with a vortex, and dried under a nitrogen gas current so that it formed a thin film. The obtained mixture was dissolved in ethanol (200 μl), which was designated as Solution A. A PBS solution [a mixed solution of $Na_2HPO_4$ (30 mM), $KH_2PO_4$ (8.8 mM), NaCl (60 mM) and EDTA (pH 7.4; 0.67 mM); 4 ml] was taken in a tube and the reaction solution was vigorously stirred with a vortex under a nitrogen current. The above-described Solution A was gently injected into this mixture with a syringe and the reaction solution was vigorously stirred with a vortex for 5 minutes under a nitrogen current. Sodium cholate (200 mM; 0.38 ml) was added to the obtained mixture and the reaction solution was stirred for 2 minutes. ApoA-I protein (3 mg) was added to the obtained mixture and the reaction solution was stirred for 2 minutes. The obtained mixture was adjusted to 5 ml with the PBS solution and then dialyzed with the PBS solution. The obtained mixture was designated as the reconstituted HDL.

(2) Preparation of Acceptor Lipoprotein

NaBr was added to the plasma of a healthy person and the density of the mixture was adjusted to 1.019, and the mixture was subjected to density gradient centrifugation (40000 rpm, for 16 hours) to remove the fraction having a density of less than 1.019. NaBr was added to the obtained mixture and the density of the solution was adjusted to 1.063, and the solution was subjected to density gradient centrifugation (40000 rpm, 18 hours) to provide the fraction consisting of IDL (intermediate density lipoprotein) and LDL (1.019<density<1.063). The obtained fraction was dialyzed with the PBS solution. The obtained mixture was designated as the acceptor lipoprotein.

(3) Measurement of CETP Inhibition Activity

A recombinant human CETP protein (manufactured by Roar Biomedical Inc.; 4.5 ng), the acceptor lipoprotein described in (2) above (32.5 μg) and 5,5'-dithio-bis-(2-nitrobenzoic acid) (7 mM, 15 μl) were taken in a 96 well plate and the total amount of the mixture was adjusted to 48.5 μl with the PBS solution. The test compound [DMSO solution (concentration: 0.15, 0.5, 1.5, 5, 15, 50, 150 and 500 μM); 1.5 μl] was added to each well and the mixture was incubated in a thermostatic bath at 37° C. for 60 minutes. The reconstituted HDL (50 μl) described in (1) above was added to each well and the mixture was reacted in a thermostatic bath at 37° C. for 60 minutes. The 96 well plate was moved onto ice and a precipitation reagent [a mixed solution of magnesium chloride (60 mM) and 0.1% dextran sulfate[1/1(v/v)]; 15 μl] was added to each well, and then the mixture was allowed to stand on ice for 15 minutes. The reaction solution (80 μl) in each well was moved to a filter plate and centrifuged at 1500 rpm for 1 minute, and the filtrate which passed through the filter was designated as the HDL fraction and the radioactivity thereof was measured with a scintillation counter. The percentage decrease in radioactivity in the case where the test compound was added in comparison with that in case where the test compound was not added was designated as the percentage CETP inhibition. The $IC_{50}$ value was calculated from the percentage CETP inhibition.

(4) Results

The test results of the salt of the compound of the present invention are shown in Table 2.

TABLE 2

| Example No. | $IC_{50}$ (nM) |
|---|---|
| 1 | 35.2 |
| 2 | 30.8 |
| 3 | 39.3 |
| 4 | 22.3 |
| 5 | 28.5 |
| 6 | 17.8 |
| 7 | 21.3 |
| 8 | 22.7 |
| 9 | 11.6 |
| 10 | 13.0 |
| 11 | 28.9 |
| 12 | 27.8 |
| 13 | 58.4 |
| 14 | 38.2 |
| 15 | 38.0 |
| 16 | 28.5 |
| 17 | 10.0 |
| 18 | 18.9 |
| 19 | 22.9 |
| 20 | 289.3 |
| 21 | 279.1 |

The salt of the compound of the present invention has excellent CETP inhibition activity in the present test and is useful as a medicament for treatment or prophylaxis of dyslipidemia, hypercholesterolemia, low HDL cholesterolemia, high LDL cholesterolemia, arteriosclerosis, arteriosclerotic heart disease, coronary heart disease or the like.

Test Example 2

Test of CETP Inhibition Activity (in vitro, Plasma-Based)

(1) Preparation of Donor Lipoprotein

NaBr was added to the human plasma and the density of the mixture was adjusted to 1.125, and the mixture was subjected to density gradient centrifugation (40000 rpm, 40 hours) to remove the fraction having a density of less than 1.125. NaBr was added to the obtained mixture and the density of the mixture was adjusted to 1.21, and the mixture was subjected to density gradient centrifugation (40000 rpm, 40 hours) to provide the fraction having the following density: 1.125<density<1.21. The obtained fraction was dialyzed with the PBS solution. The obtained mixture was designated as the $HDL_3$ fraction. Phosphatidyl choline (5 mg) and [$^3$H]-labeled cholesteryl ester (0.5 mCi; 0.5 ml) were taken in a glass test tube and dried under a nitrogen current. PBS solution (500 μl) was added to the obtained mixture and the mixture was mixed for 30 minutes under ultrasonic wave irradiation. The $HDL_3$ fraction (1.75 mg) and the lipoprotein-depleted human serum (LPDS; 12 mg) were added to the obtained mixture and the total amount of the mixture was adjusted to 3.5 ml with the PBS solution. The obtained mixture was incubated at 37° C. for 48 hours. NaBr was added to the obtained mixture and the density of the mixture was adjusted to 1.063, and the mixture was subjected to density gradient centrifugation (40000 rpm, 18 hours) to remove the fraction having a density of less than 1.063. NaBr was added to the obtained fraction and the density of the mixture was adjusted to 1.21, and the mixture was subjected to density gradient centrifugation (40000 rpm, 40 hours) to provide the fraction having the following density: 1.063<density<1.21. The obtained fraction was dialyzed with the PBS solution and the mixture was designated as the donor lipoprotein.

(2) Measurement of CETP Inhibition Activity

The donor lipoprotein described in (1) above (2 μL) and the test compound [DMSO solution (concentration: 0.15, 0.5, 1.5, 5, 15, 50, 150 and 500 μM); 1 μL] were mixed with the human plasma or the plasma (37 μL) collected from double-transgenic mice into which human Apo B and human CETP gene were introduced (hereinafter, CETP/apoB Tg mice; J. Lipid Res., 1995, Vol. 36, pp. 1082-1091) and the mixture was added to a 96-well V bottom plate (total 40 μL). The mixture was lightly mixed and then reacted at 37° C. for 2 hours. The 96-well V bottom plate was moved onto ice and a precipitation reagent [a mixed solution of magnesium chloride (200 mM) and 0.2% dextran sulfate[1/1(v/v)]; 10 μl] was added to each well, and then the mixture was allowed to stand on ice for 15 minutes. The reaction solution (40 μl) in each well was moved to a filter plate and centrifuged at 1500 rpm for 1 minute. The filtrate which passed through the filter was designated as the HDL fraction and the fraction which remained on the filter was designated as the LDL fraction, and the radioactivity of each fraction was measured with a scintillation counter, respectively. The percentage transfer of cholesteryl ester was calculated from the radioactivities of the HDL fraction and the LDL fraction before and after the reaction at 37° C. according to the formula described below.

Percentage transfer of cholesteryl ester (%) =[[Radioactivity of LDL fraction (after reaction)−Radioactivity of LDL fraction (before reaction)]/[Radioactivity of LDL fraction (after reaction)+ Radioactivity of HDL fraction (after reaction)]]× 100

The percentage decrease in the percentage transfer of cholesteryl ester in the case where the test compound was added in comparison with that in the case where the test compound was not added was designated as the percentage CETP inhibition. The $IC_{50}$ value was calculated from the percentage CETP inhibition.

The salt of the compound of the present invention has excellent CETP inhibition activity in the present test and is useful as a medicament for treatment or prophylaxis of dyslipidemia, hypercholesterolemia, low HDL cholesterolemia, high LDL cholesterolemia, arteriosclerosis, arteriosclerotic heart disease, coronary heart disease or the like.

Test Example 3

Test of CETP Inhibition Activity (in vitro, Fluorescence, Plasma-Based)

Reagent A (73 μl) of Ex vivo CETP Activity Assay (RB-EVAK) manufactured by Roar Biomedical Inc. was mixed with Reagent B (311 µl) of the same to prepare Reagent C. 2.5 µl of Reagent C was mixed with the human plasma or the plasma collected from CETP/ApoB Tg mice (46.5 µl) and the mixture was added to a 96 well black plate (Half Area, No. 3694 manufactured by Corning). The test compound [DMSO solution (concentration: 0.15, 0.5, 1.5, 5, 15, 50, 150 and 500 µM); 1 µl] was added to each well and the mixture was lightly mixed. The mixture was reacted for 90 minutes in a thermostatic bath at 37° C. and the fluorescence intensity of the sample in each well was measured (excitation wavelength: 485 nm; fluorescence wavelength: 530 nm) with a fluorescence plate reader (manufactured by LJL Biosystems; Analyst HT). The fluorescence intensity in the reaction using the plasma of the wild-type mice was deducted as a blank and the percentage decrease in the fluorescence intensity in the case where the test compound was added in comparison with that in the case where the test compound was not added was designated as the percentage CETP inhibition. The $IC_{50}$ value was calculated from the percentage CETP inhibition.

The salt of the compound of the present invention has excellent CETP inhibition activity in the present test and is useful as a medicament for treatment or prophylaxis of dyslipidemia, hypercholesterolemia, low HDL cholesterolemia, high LDL cholesterolemia, arteriosclerosis, arteriosclerotic heart disease, coronary heart disease or the like.

Test Example 4

Test of Pharmacological Effect in Mice (Mice in vivo and Mice ex vivo)

(1) Administration of Compound

The test compound was dissolved in a mixed solvent of propylene glycol-Tween 80 (trade name) [4/1(v/v)] and orally administered to CETP/apoB Tg mice for 2 or 7 days. The blood was collected before the administration and 14 or 24 hours after the administration on the 2nd or 7th day.

(2) Measurement of Cholesterol Content in Plasma

The cholesterol content in plasma was measured using a commercially available measurement kit (cholesterol-E Wako, manufactured by Wako Junyaku Inc.).

(3) Measurement of the Contents of HDL Cholesterol and Non-HDL Cholesterol

The lipoprotein profile was analyzed by HPLC (column: Lipopropack XL, manufactured by Tosoh Corp.). The contents of HDL cholesterol and non-HDL cholesterol were calculated according to the calculation formula described below.

HDL cholesterol content=Cholesterol content in plasma×(peak area of HDL cholesterol/sum of each peak area)

Non-HDL cholesterol content=Cholesterol content in plasma×(peak area of non-HDL cholesterol/sum of each peak area)

(4) Preparation of Donor Lipoprotein

NaBr was added to the human plasma and the density of the mixture was adjusted to 1.125, and the mixture was subjected to density gradient centrifugation (40000 rpm, 40 hours) to remove the fraction having a density of less than 1.125. NaBr was added to the obtained mixture and the density of the mixture was adjusted to 1.21, and the mixture was subjected to density gradient centrifugation (40000 rpm, 40 hours) to provide the fraction having the following density: 1.125<density<1.21. The obtained fraction was dialyzed with the PBS solution. The obtained mixture was designated as the $HDL_3$ fraction. Phosphatidyl choline (5 mg) and tritium-labeled cholesteryl ester (0.5 mCi; 0.5 ml) were taken in a glass test tube and dried under a nitrogen current. The PBS solution (500 µl) was added to the obtained mixture and the mixture was mixed under ultrasonic wave irradiation for 30 minutes. The $HDL_3$ fraction (1.75 mg) and the lipoprotein-depleted human serum (12 mg) was added to the obtained mixture and the total amount of the mixture was adjusted to 3.5 ml with the PBS solution. The obtained mixture was incubated at 37° C. for 48 hours. NaBr was added to the obtained mixture and the density of the mixture was adjusted to 1.063, and the mixture was subjected to density gradient centrifugation (40000 rpm, 18 hours) to remove the fraction having a density of less than 1.063. NaBr was added to the obtained fraction and the density of the mixture was adjusted to 1.21, and the mixture was subjected to density gradient centrifugation (40000 rpm, 40 hours) to provide the fraction having the following density: 1.063<density<1.21. The obtained fraction was dialyzed with the PBS solution. The obtained mixture was designated as the donor lipoprotein.

(5) Measurement of CETP Inhibition Activity (Fluorescence, ex vivo)

Reagent A (73 µl) and Reagent B (311 µl) of Ex vivo CETP Activity Assay (RB-EVAK) of Roar Biomedical Inc. were mixed to prepare Reagent C. 1 µl of Reagent C and the plasma (19 µl) collected from the test animal were added to a black 384 well round-bottom plate (No. 3676 manufactured by Corning). The mixture was reacted in a thermostatic bath at 37° C. for 90 minutes and the fluorescence intensity of the sample in each well was measured (excitation wavelength: 485 nm, fluorescence wavelength: 530 nm) with a fluorescence plate reader (manufactured by LJL Biosystems: Analyst HT). The fluorescence intensity in the reaction using the plasma of the wild-type mice was deducted as a blank and the percentage decrease in the fluorescence intensity in the case where the test compound was added in comparison with that in case where the test compound was not added was designated as the percentage CETP inhibition.

The salt of the compound of the present invention has excellent CETP inhibition activity, increasing action on the concentration of HDL cholesterol or decreasing action on the concentration of LDL cholesterol in the present test and is useful as a medicament for treatment or prophylaxis of dyslipidemia, hypercholesterolemia, low HDL cholesterolemia, high LDL cholesterolemia, arteriosclerosis, arteriosclerotic heart disease, coronary heart disease or the like.

Formulation Example 1

Hard Capsule

Powdered salt of the compound of Example (100 mg), lactose (150 mg), cellulose (50 mg) and magnesium stearate (6 mg) are filled into a standard two-split hard gelatin capsule to prepare a hard capsule and the hard capsule is washed and then dried.

Formulation Example 2

Soft Capsule

A mixture of a digestible oil material such as soybean oil and olive oil and the salt of the compound of Example are injected into gelatin so as to contain 100 mg of active ingredient to prepare a soft capsule and the soft capsule is washed and then dried.

Formulation Example 3

Tablet

A tablet is prepared according to a method which is well known in the field of formulation science using the salt of the compound of Example (100 mg), colloidal silicon dioxide (0.2 mg), magnesium stearate (0.2 mg), microcrystalline cellulose (0.2 mg), starch (0.2 mg) and lactose (98.8 mg). The obtained tablet may be coated as necessary.

INDUSTRIAL APPLICABILITY

The salt of the compound represented by general formula (I) or (I-1) of the present invention has excellent properties in terms of CETP inhibition activity, increasing action on the concentration of HDL cholesterol, decreasing action on the concentration of LDL cholesterol, rapid onset of pharmacological effect, prolonged pharmacological effect, physical stability, solubility, oral absorbability, blood concentration, cell membrane permeability, metabolic stability, tissue migration, bioavailability (BA), drug-drug interaction, toxicity or the like, and is useful as a medicament for a warm-blooded animal (particularly, for a human). The above-described medicament is a medicament for treatment or prophylaxis of, preferably dyslipidemia, hypercholesterolemia, low HDL cholesterolemia, high LDL cholesterolemia, hypertriglyceridemia, arteriosclerosis, arteriosclerotic heart disease, coronary heart disease (including heart failure, myocardial infarction, angina pectoris, cardiac ischemia, cardiovascular disorder and angioplasty-related restenosis), cerebrovascular disease (including stroke and cerebral infarction), peripheral vascular disease (including diabetic vascular complications) or obesity, more preferably dyslipidemia, low HDL cholesterolemia, high LDL cholesterolemia, arteriosclerosis, arteriosclerotic heart disease or coronary heart disease, further preferably dyslipidemia, low HDL cholesterolemia, arteriosclerosis or coronary heart disease, and even more preferably low HDL cholesterolemia or arteriosclerosis.

The invention claimed is:

1. A salt formed from a compound of formula (I):

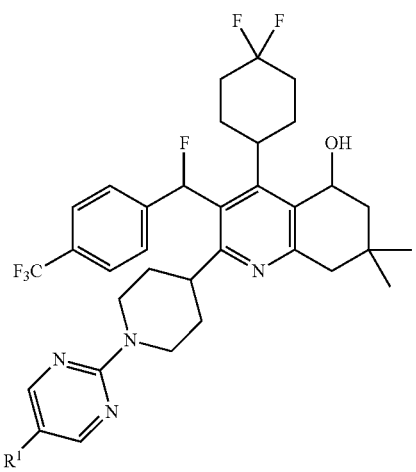

(I)

wherein $R^1$ is a (2S)-2,3-dihydroxypropyloxy group, a (2R)-2,3-dihydroxypropyloxy group, a 3-hydroxy-3-methylbutoxy group, a 3-(methylsulfonyl)propoxy group, a 3-hydroxy-2-(hydroxymethyl)propoxy group, a 3-hydroxy-2-(hydroxymethyl)-2-methylpropoxy group or a 3-carboxyphenyl group, and an acid selected from hydrochloric acid, hydrobromic acid, methanesulfonic acid, benzenesulfonic acid, succinic acid, fumaric acid and maleic acid.

2. The salt of the compound of claim 1, which is formed from a compound of formula (I-1):

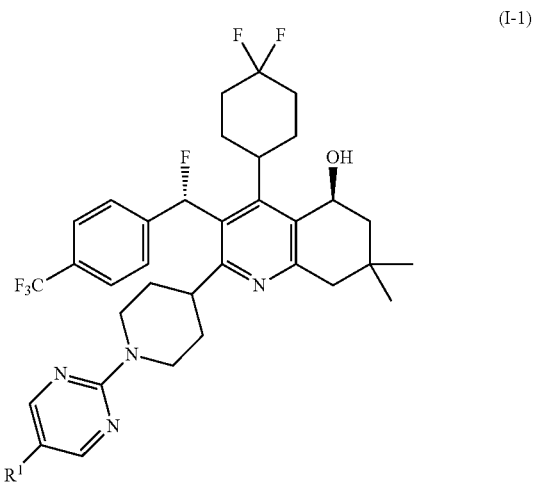

(I-1)

wherein $R^1$ is a (2S)-2,3-dihydroxypropyloxy group, a (2R)-2,3-dihydroxypropyloxy group, a 3-hydroxy-3-methylbutoxy group, a 3-(methylsulfonyl)propoxy group, a 3-hydroxy-2-(hydroxymethyl)propoxy group, a 3-hydroxy-2-(hydroxymethyl)-2-methylpropoxy group or a 3-carboxyphenyl group, and an acid selected from hydrochloric acid, hydrobromic acid, methanesulfonic acid, benzenesulfonic acid, succinic acid, fumaric acid and maleic acid.

3. The salt of the compound of claim 2, wherein $R^1$ is a (2S)-2,3-dihydroxypropyloxy group.

4. The salt of the compound of claim 2, wherein $R^1$ is a (2R)-2,3-dihydroxypropyloxy group.

5. The salt of the compound of claim 2, wherein $R^1$ is a 3-hydroxy-3-methylbutoxy group.

6. The salt of the compound of claim 2, wherein $R^1$ is a 3-(methylsulfonyl)propoxy group.

7. The salt of the compound of claim 2, wherein $R^1$ is a 3-hydroxy-2-(hydroxymethyl)propoxy group.

8. The salt of the compound of claim 2, wherein $R^1$ is a 3-hydroxy-2-(hydroxymethyl)-2-methylpropoxy group.

9. The salt of the compound of claim 2, wherein $R^1$ is a 3-carboxyphenyl group.

10. A pharmaceutical composition comprising the salt of the compound of claim 2 and a pharmaceutically acceptable excipient.

11. A method of treatment of a disease comprising administering to a warm-blooded animal a pharmacologically effective amount of the salt of the compound of claim 2, wherein the disease is dyslipidemia, hypercholesterolemia, low HDL cholesterolemia, high LDL cholesterolemia, hypertriglyceridemia, arteriosclerosis, arteriosclerotic heart disease, coronary heart disease, cerebrovascular disease, peripheral vascular disease or obesity.

12. The method of claim 11, wherein the disease is dyslipidemia, low HDL cholesterolemia, arteriosclerosis or coronary heart disease.

13. The method of claim 11, wherein the disease is low HDL cholesterolemia.

14. The method of claim 11, wherein the disease is arteriosclerosis.

15. The method of claim 11, wherein the warm-blooded animal is a human.

16. A method of treatment of a disease comprising administering to a warm-blooded animal a pharmacologically effective amount of the salt of the compound of claim 2, wherein the disease is a disease caused by a decrease in the blood concentration of HDL cholesterol.

17. A method of treatment of a disease comprising administering to a warm-blooded animal a pharmacologically effective amount of the salt of the compound of claim 2, wherein the disease is a disease caused by an increase in the blood concentration of LDL cholesterol.

18. The method of claim 11, wherein the disease is dyslipidemia.

* * * * *